(12) United States Patent
Kabanov et al.

(10) Patent No.: US 9,402,908 B2
(45) Date of Patent: Aug. 2, 2016

(54) POLYMERIC DELIVERY SYSTEMS FOR ACTIVE AGENTS

(71) Applicants: Alexander V. Kabanov, Chapel Hill, NC (US); Rainer Jordan, Dresden (DE); Robert Luxenhofer, Dresden (DE)

(72) Inventors: Alexander V. Kabanov, Chapel Hill, NC (US); Rainer Jordan, Dresden (DE); Robert Luxenhofer, Dresden (DE)

( * ) Notice: Subject to any disclaimer, the term of this patent is extended or adjusted under 35 U.S.C. 154(b) by 68 days.

(21) Appl. No.: 14/144,831

(22) Filed: Dec. 31, 2013

(65) Prior Publication Data

US 2014/0170197 A1   Jun. 19, 2014

Related U.S. Application Data

(63) Continuation of application No. 12/976,162, filed on Dec. 22, 2010, now abandoned, which is a continuation-in-part of application No. 12/492,660, filed on Jun. 26, 2009, now abandoned, and a continuation-in-part of application No. PCT/EP2009/004655, filed on Jun. 26, 2009.

(60) Provisional application No. 61/166,154, filed on Apr. 2, 2009, provisional application No. 61/134,209, filed on Jul. 8, 2008, provisional application No. 61/133,154, filed on Jun. 26, 2008.

(51) Int. Cl.
| | |
|---|---|
| A61K 47/32 | (2006.01) |
| G01N 33/50 | (2006.01) |
| A61K 38/13 | (2006.01) |
| A01N 43/90 | (2006.01) |
| A61K 31/337 | (2006.01) |
| A01N 25/10 | (2006.01) |
| A61K 9/00 | (2006.01) |
| A61K 9/107 | (2006.01) |
| A61K 9/19 | (2006.01) |
| A61K 47/34 | (2006.01) |
| A01N 25/04 | (2006.01) |
| A01N 25/30 | (2006.01) |

(52) U.S. Cl.
CPC .............. *A61K 47/32* (2013.01); *A01N 25/04* (2013.01); *A01N 25/10* (2013.01); *A01N 25/30* (2013.01); *A01N 43/90* (2013.01); *A61K 9/0019* (2013.01); *A61K 9/1075* (2013.01); *A61K 9/19* (2013.01); *A61K 31/337* (2013.01); *A61K 38/13* (2013.01); *A61K 47/34* (2013.01); *G01N 33/5005* (2013.01)

(58) Field of Classification Search
CPC ...... A61K 9/0019; A61K 9/1075; A61K 9/19; A61K 31/337; A61K 38/13; A61K 47/32; A61K 47/34; A01N 25/30; A01N 25/10; A01N 43/90; A01N 25/04; G01N 33/005
See application file for complete search history.

(56) References Cited

FOREIGN PATENT DOCUMENTS

JP   H04-128207 A   4/1992

OTHER PUBLICATIONS

Hoogenboom, R. et al. Microwave-Assisted Cationic Ring-Opening Polymerization of 2-Oxazolines: A Powerful Method for the Synthesis of Amphiphilic Triblock Copolymers, Macromolecules, 2006, 39, 4719-4725.*

Lee, S. C. et al. Polymeric Miscelles of Poly(2-ethyl-2-oxazoline)-block-poly(epsilon-caprolactone) copolymer as a carrier for paclitaxel, J. Contr. Rel. 2003, 89, 437-446.*

* cited by examiner

*Primary Examiner* — Ali Soroush
*Assistant Examiner* — Genevieve S Alley
(74) *Attorney, Agent, or Firm* — Stolmar & Partner; Robert Lelkes

(57) ABSTRACT

The present invention provides polymer aggregates as delivery vehicles for therapeutics and diagnostics. The present invention additionally provides methods of synthesis and uses for such aggregates.

33 Claims, 27 Drawing Sheets

FIG. 14
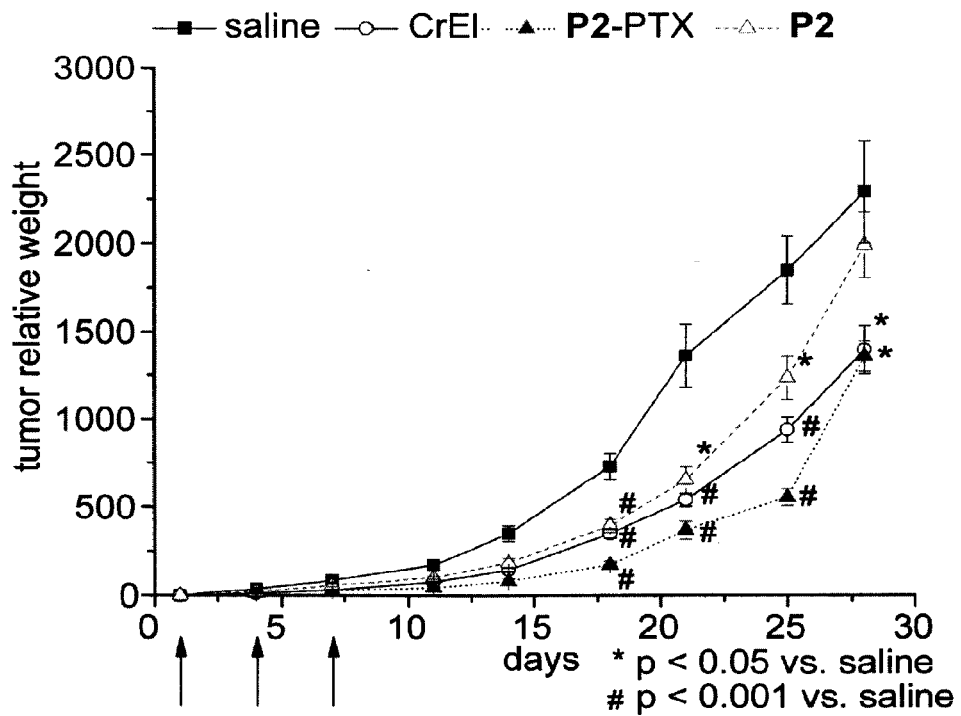
FIG. 14A
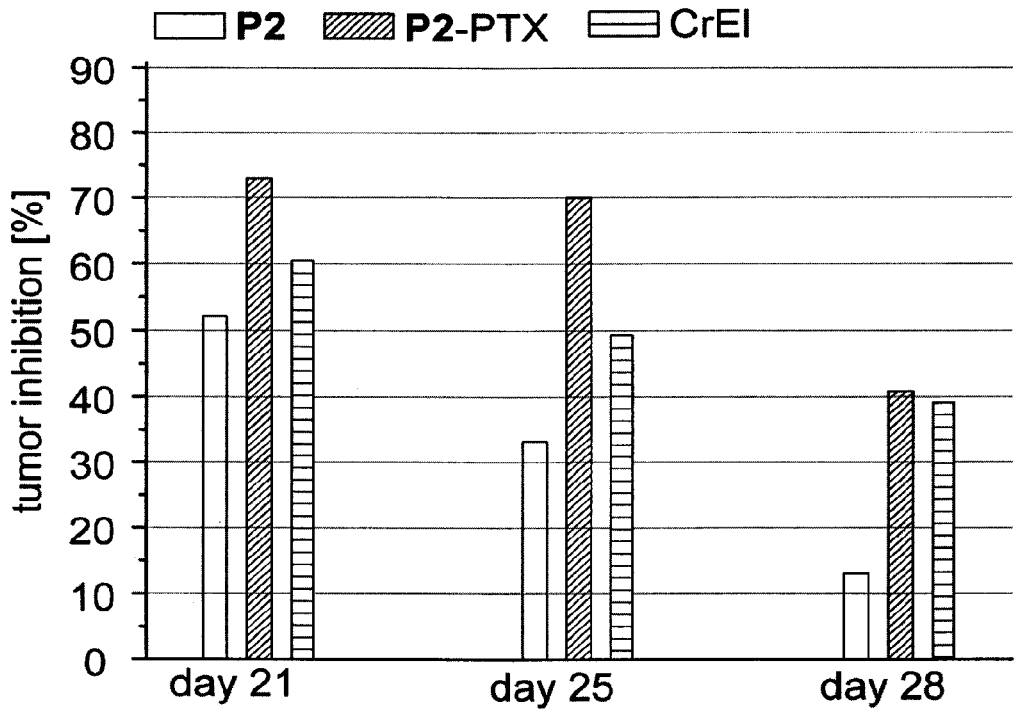
FIG. 14B

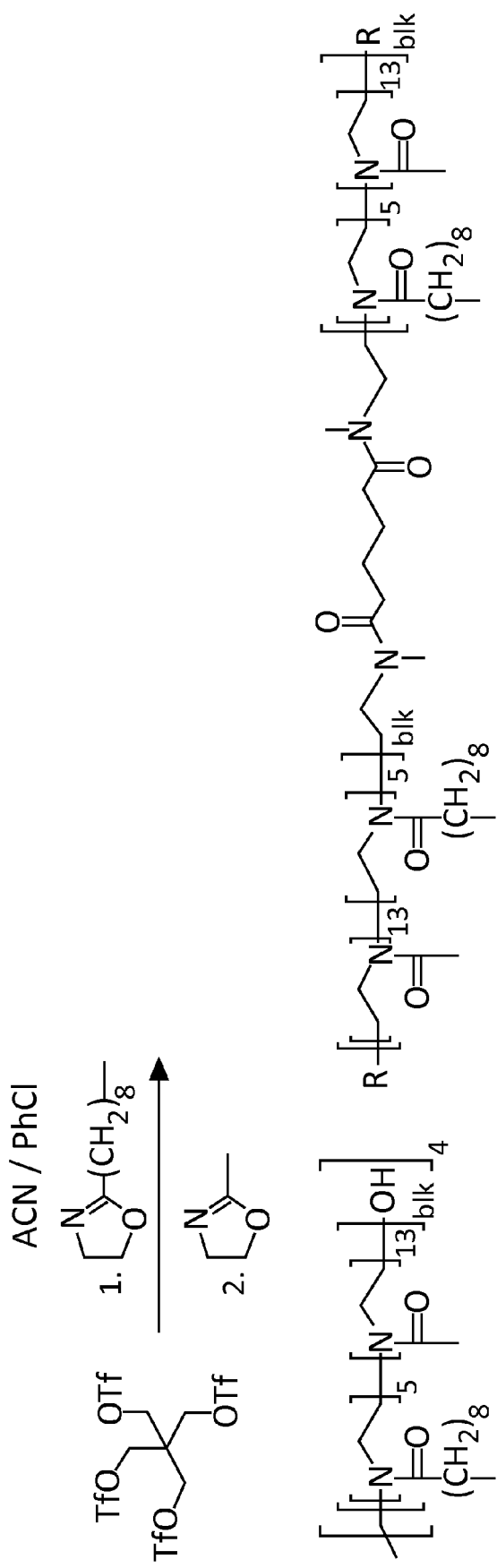
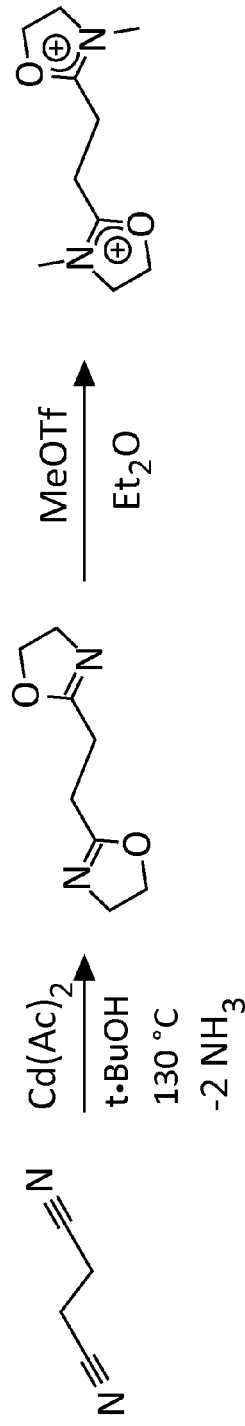
FIG. 15A
FIG. 15B

POLYMERIC DELIVERY SYSTEMS FOR ACTIVE AGENTS

RELATED APPLICATIONS

This application claims priority under 35 U.S.C. §120 based on U.S. Nonprovisional patent application Ser. No. 12/976,162 filed on Dec. 22, 2010, which is a continuation-in-part under 35 U.S.C. §120 of U.S. Nonprovisional patent application Ser. No. 12/492,660, filed on Jun. 26, 2009, and International PCT Application No. PCT/EP2009/004655 filed on Jun. 26, 2009, each of which claims priority under 35 U.S.C. §119(e) based on U.S. Provisional Patent Application No. 61/133,154, filed on Jun. 26, 2008 and U.S. Provisional Patent Application No. 61/134,209, filed on Jul. 8, 2008. Each of the foregoing applications is fully incorporated herein by reference.

GOVERNMENT SUPPORT

This invention was made with government support under Grant No. 2R01CA89225 awarded by the National Institutes of Health. The government has certain rights in the invention.

FIELD OF THE INVENTION

The present invention relates to compositions and formulations which contain an active compound, especially a hydrophobic active compounds, together with a delivery system which assists in the solubilisation of these compounds. In particular, the present invention relates generally to the solubilization of biologically active compounds with polymeric excipients of amphiphilic nature. The present invention relates to compositions and methods for the delivery of therapeutic and diagnostic agents, particularly hydrophobic compounds, to a patient.

BACKGROUND OF THE INVENTION

A great number of potent drugs and potential drug candidates have a low solubility in water or aqueous solutions, thus limiting their scope of use. Formulation of poorly soluble drugs, such as paclitaxel (PTX) with a water solubility of approx. 1 µg/mL, remains a major challenge in drug delivery (Huh, K. M., et al., J. Controlled Release 126, 122-129 (2008); Dabholkar, R. D., et al. Int. J. Pharm. 315, 148-157 (2006); Yang, T., et al., Int. J. Pharm. 338, 317-326 (2007); Torchilin, V. P., Cell. Mol. Life. Sci 61, 2549-2559 (2004); Haag, R., Angew. Chem. Int. Ed. 43, 278-282 (2004)). The current clinical formulation of PTX, Taxol®, contains less than 1% w/w of active drug, but 99% w/w of excipients know to cause considerable side effects for the patients. Similar problems are encountered with active agents in other technical areas, such as plant protection, etc. Various methods to solubilize or disperse active agents have been developed. Traditional methods are typically based on the use of solvents, surfactants or chelating agents. These methods have one or more disadvantages related to toxicity of the excipients, limited stability of the formulations in aqueous media, in particular upon dilution, or difficult formulation procedures.

It is therefore necessary or beneficial to be able to solubilize or formulate hydrophobic drugs in aqueous media. The solubilized drugs may have improved dispersion in the aqueous media and/or increased stability in the aqueous dispersions.

Various methods to solubilize or disperse drugs have been developed. These methods are typically based on the use of solvents, surfactants, chelating agents or other drug delivery systems such as liposomes. These methods have one or more disadvantages related to the toxicity of the excipients, difficult formulation procedures, and/or limited stability of the formulations in aqueous media. Stability is a particularly problematic upon the dilution encountered when administered to a patient.

Copolymers comprising at least one hydrophilic and one hydrophobic block (amphiphilic block copolymers) have been shown to be effective for the solubilization of drugs of limited solubility in aqueous media.

More recently, liposomes (Wu, J., et al., Int. J. Pharm. 316, 148-153 (2006)), micro- and nanoparticles (Desai, N. P. et al., Anti-Cancer Drugs 19, 899-909 (2008)) and polymer micelles (Huh, K. M., et al., J. Controlled Release 126, 122-129 (2008); Konno, T., et al., J. Biomed. Mat. Res., Part A, 65A, 210-215 (2002); Kim, S. C., et al., J. Controlled Release 72, 191-202 (2001)) have been studied intensively as solubilisation/drug delivery systems, each approach having advantages and disadvantages. One major limitation of polymer micelles is the loading capacity and the total amount of drug that can be solubilized.

U.S. Patent Application Publication No. 2004/0185101 discloses polymeric compositions with the capability to solubilize hydrophobic drugs in aqueous media. The biodegradable ABA-type or BAB-type block copolymers used in this approach can markedly increase the solubility of hydrophobic drugs, such as paclitaxel, in aqueous solution. However, one disadvantage of this approach is that the amount of polymer excipient is very high, typically between 10 and 30%. Moreover, the loading capacity of these compositions is very limited with a loading capacity of <10% (w/w) for paclitaxel and less than 1% (w/w) for cyclosporin A.

Poly(2-oxazoline)s have recently attracted considerable attention for biomedical applications. Of particular interest are hydrophilic poly(2-methyl-2-oxazoline) (PMeOx) and poly(2-ethyl-2-oxazoline) (PEtOx) as they exhibit stealth (Zalipsky, S., et al., J. Pharm. Sci. 85, 133-137 (1996); Woodle, M. C., et al., Bioconjugate Chem. 5, 494-496 (1994)) and protein repellent effects (Konradi, R., et al., Langmuir 24, 613-616 (2008)) and undergo rapid renal clearance (Gaertner, F. C., et al., J. Controlled Release 119, 219-300 (2007)) similar to poly(ethylene glycol), a commonly used polymer for injectable drug delivery systems.

To date, few nontoxic biocompatible formulations are known for the solubilization of paclitaxel. The only formulation commercially available utilizes a 1/1 mixture of Cremophor EL® and dehydrated ethanol (v/v). While this formulation is able to solubilize relatively large amounts of paclitaxel (6 mg/ml) in the pure formulation which must then be diluted to obtain in administrable aqueous solution), it can also cause severe side effects in patients. It is therefore highly desirable to find new ways to formulate paclitaxel and other drugs in aqueous media suitable for intravenous injection to patients.

It is the aim of the present invention to provide compositions containing a delivery system which allows active agents, in particular hydrophobic active agents, to be efficiently solubilised and/or formulated. In particular, the compositions should be simple to prepare and provide a high loading capacity for the subject active agent.

SUMMARY OF THE INVENTION

In accordance with the instant invention, compositions and methods are provided for the solubilization of compounds, particularly hydrophobic compounds and/or active agents. In accordance with one aspect of the invention, compositions are provided comprising 1) at least one copolymer, which is preferably a block copolymer, more preferably an amphiphilic block copolymer, comprising at least one hydrophilic segment and at least one hydrophobic segment, and 2) at least one hydrophobic compound and/or active agent, particularly a therapeutic agent. The composition may further comprise at least one pharmaceutically acceptable carrier. In a preferred embodiment, the hydrophilic segment is a hydrophilic poly(2-oxazoline) and the hydrophobic segment is a hydrophobic poly(2-oxazoline).

In one embodiment, the present invention provides compositions, comprising
(a) at least one copolymer comprising repeating units of formula (I)

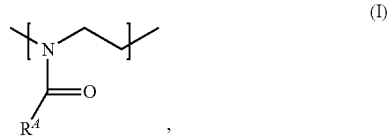
(I)

wherein $R^A$ is a hydrocarbon group, optionally substituted with —OH, —SH, —COOH, —NR'$_2$, —COOR', —CONR', —CHO, with R' representing H or $C_{1-3}$ alkyl, and with $R^A$ being selected such that the repeating unit of formula (I) is hydrophilic,
and repeating units of the formula (II),

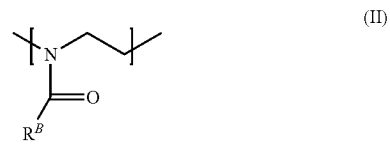
(II)

wherein $R^B$ is a hydrocarbon group optionally substituted with halogen, —OH, —SH, —COOH, —NR''$_2$, —COOR'', —CONR'', —CHO, with R'' representing H, alkyl or alkenyl, and with $R^B$ being selected such that the repeating unit of formula (II) is more hydrophobic than the repeating unit of formula (I); and
(b) one or more active agent(s).

In a particular embodiment, the hydrophilic segment is poly(2-methyl-2-oxazoline) or poly(2-ethyl-2-oxazoline) and the hydrophobic segment is poly(2-alkyl-2-oxazoline), wherein the alkyl comprises three to six carbons (e.g., butyl).

Furthermore, the invention provides selected copolymers as defined above. The compositions according to the invention can be used in various technical fields, including pharmaceutical applications, diagnostic applications (including veterinary applications) and plant protection.

In accordance with another aspect of the instant invention, methods for delivering at least one compound to a subject are provided. The methods comprise administering at least one composition of the instant invention to a subject. In a particularly embodiment, the compound is a hydrophobic compound and/or active agent, particularly a therapeutic agent.

In accordance with yet another aspect of the instant invention, methods of treating a disorder or disease in a patient in need thereof are provided. The methods comprise administering at least one composition of the instant invention to the patient. In a particular embodiment, the disease is cancer and the administered compound is a chemotherapeutic agent such as a taxane.

BRIEF DESCRIPTIONS OF THE DRAWING

FIG. 1A is a graph demonstrating the loading of paclitaxel in compositions comprising LXRB20 and increasing amounts of paclitaxel. FIG. 1B is a graph demonstrating the loading of paclitaxel in compositions comprising LXRB10, LXRB15, or LXRB20. The columns show the paclitaxel concentration in aqueous micelle solution as determined by HPLC. The line graph represents the loading efficiency ([paclitaxel]det/[paclitaxel]o×100%).

FIGS. 5A-5D provide graphs showing the fluorescence intensity and I1/I3 ratios of pyrene solutions ($5\times10^{-7}$ M in PBS) at various concentrations of P1-P4, respectively, at 25° C.

Figure 6A:
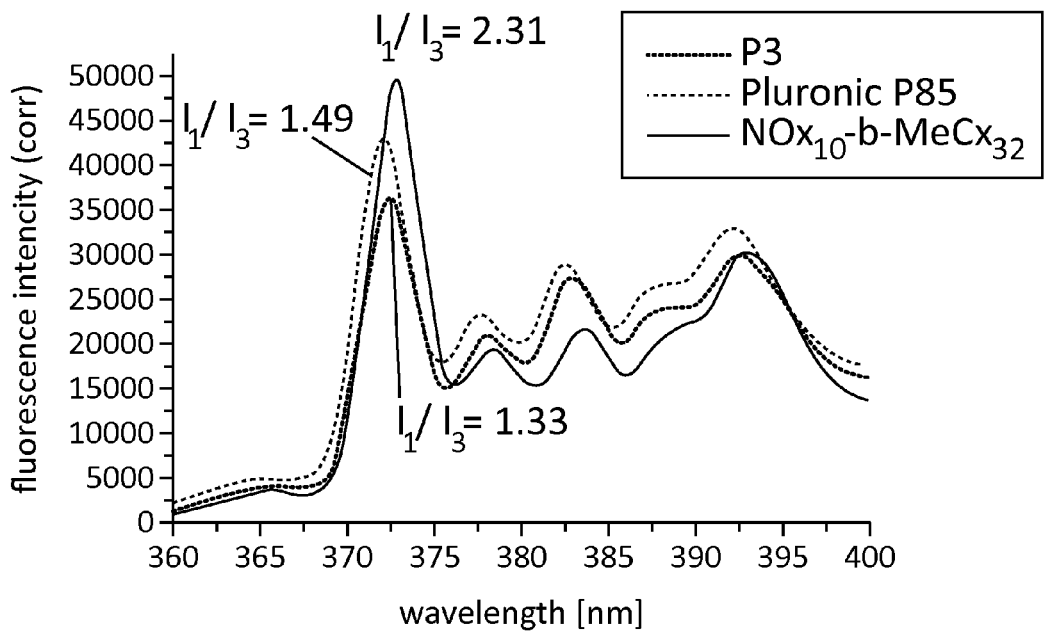
Figure 6B:
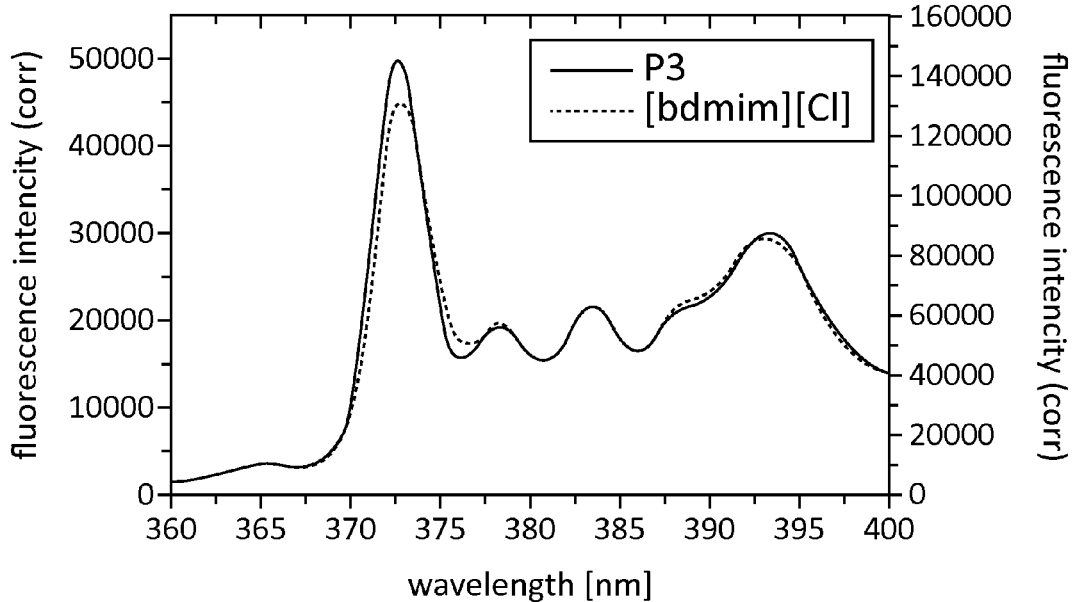

FIG. 6A is a graph of the pyrene fluorescence spectra recorded at room temperature in aqueous solutions of 2-nonyl-2-oxazoline based block copolymer NOx$_{10}$-b-MeOx$_{32}$ ($2.1\times10^{-4}$ M), Pluronic® P85 ($2.2\times10^{-3}$ M), and the 2-butyl-2-oxazoline based MeOx$_{36}$-b-BuOx$_{30}$-b-MeOx$_{36}$ (P3, $7.1\times10^{-4}$ M). FIG. 6B provides a comparison between pyrene fluorescence spectra in P3 ($7.1\times10^{-4}$ M) and an ionic liquid (1-butyl-2,3-dimethylimidazolium chloride) ([pyrene]=$5\times10^{-7}$ M, $\lambda_{exc}$=333 nm, pH 7.2).

Figures 7A, 7B:
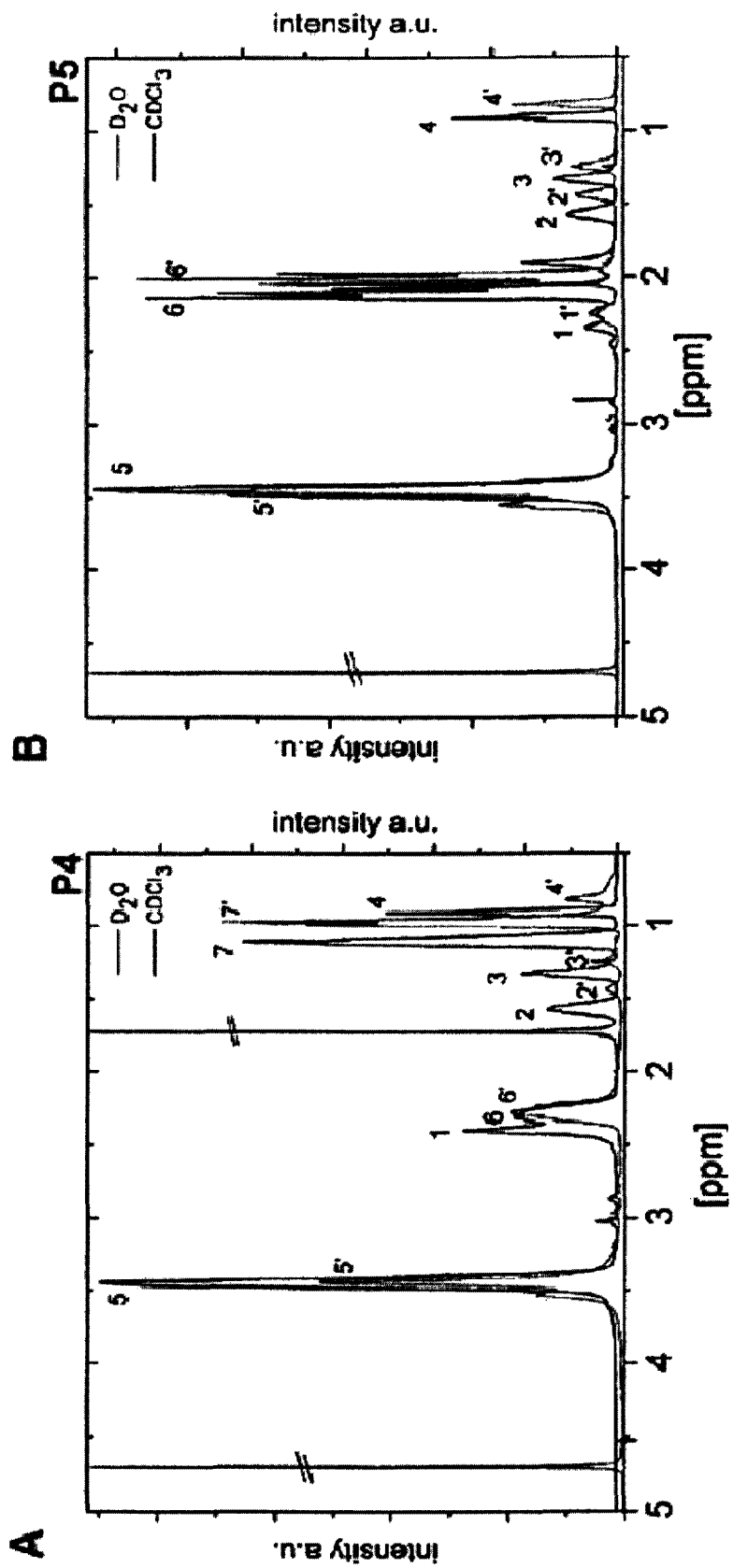

FIGS. 7A and 7B provide a comparison of $^1$H-NMR spectra of P4 (FIG. 7A) and P5 (FIG. 7B) (300K, 400 MHz, normalized for methyl or ethyl side chain, respectively) in deuterated chloroform (no aggregates present) and D$_2$O (formation of polymeric micelles). Signals 1-4 (CDCl$_3$) and 1'-4' (D$_2$O) originated from butyl side chains in the hydrophobic block of P4 and P5, signals 5/5' originated from polymer main chain, and signals 6/6' and 7/7' originated from side chains in the hydrophilic block.

Figure 8A:
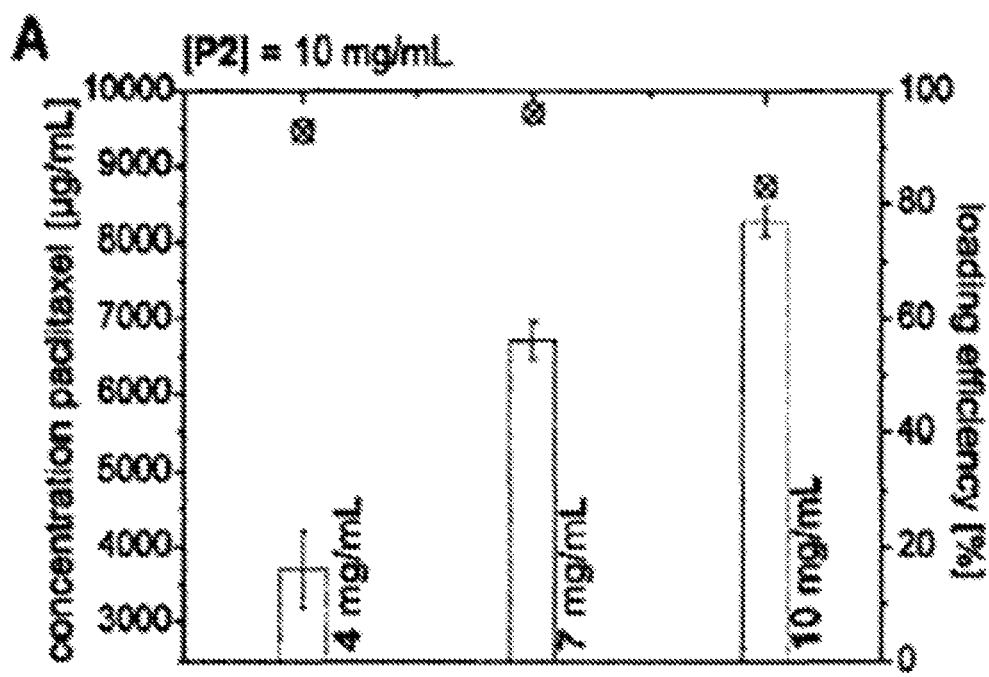
Figure 8B:
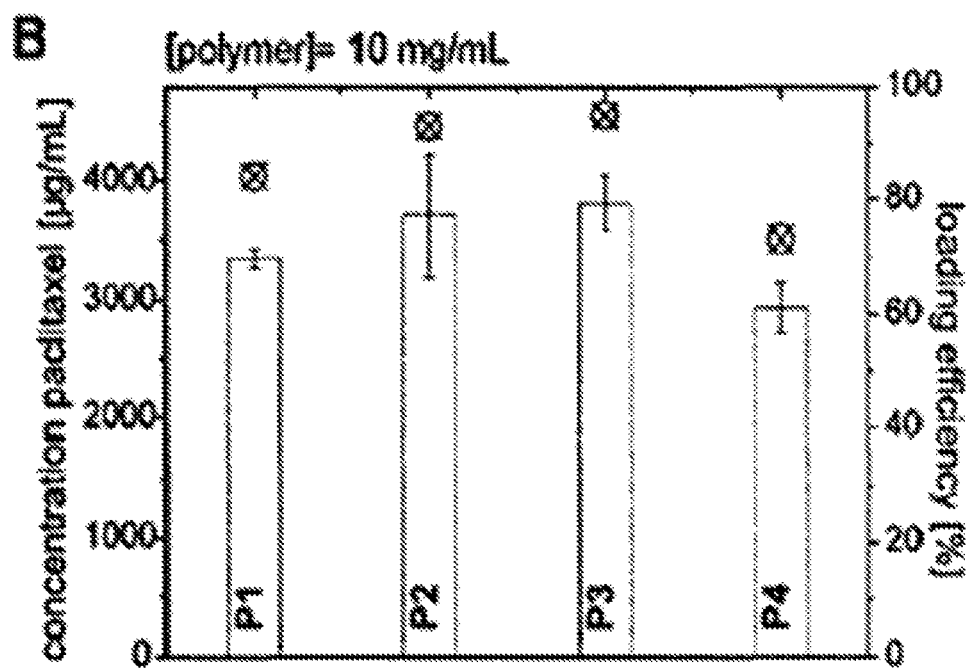
Figure 8C:
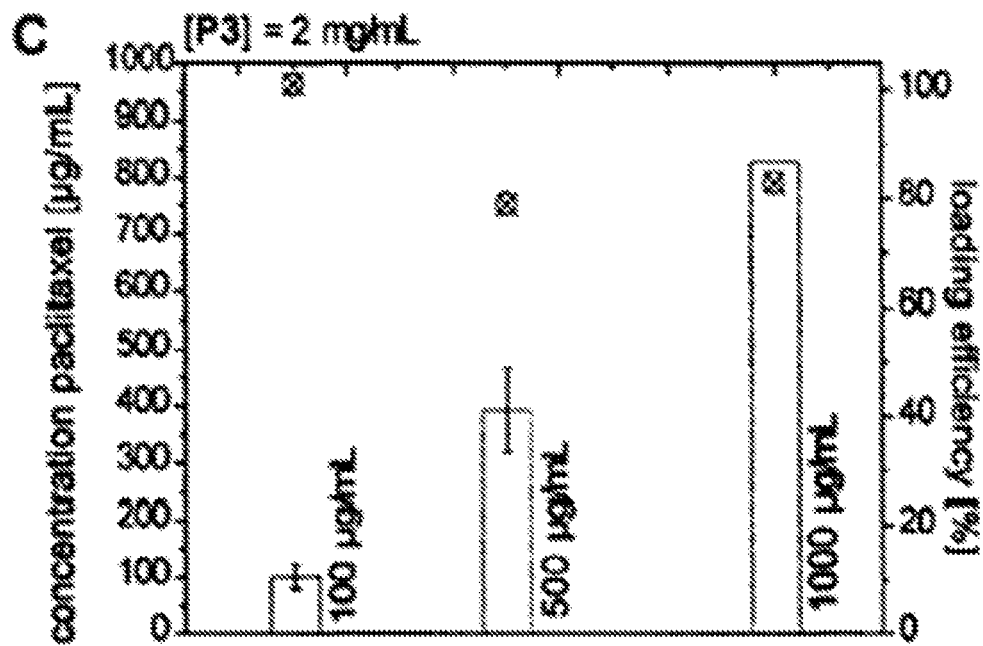
Figure 8D:
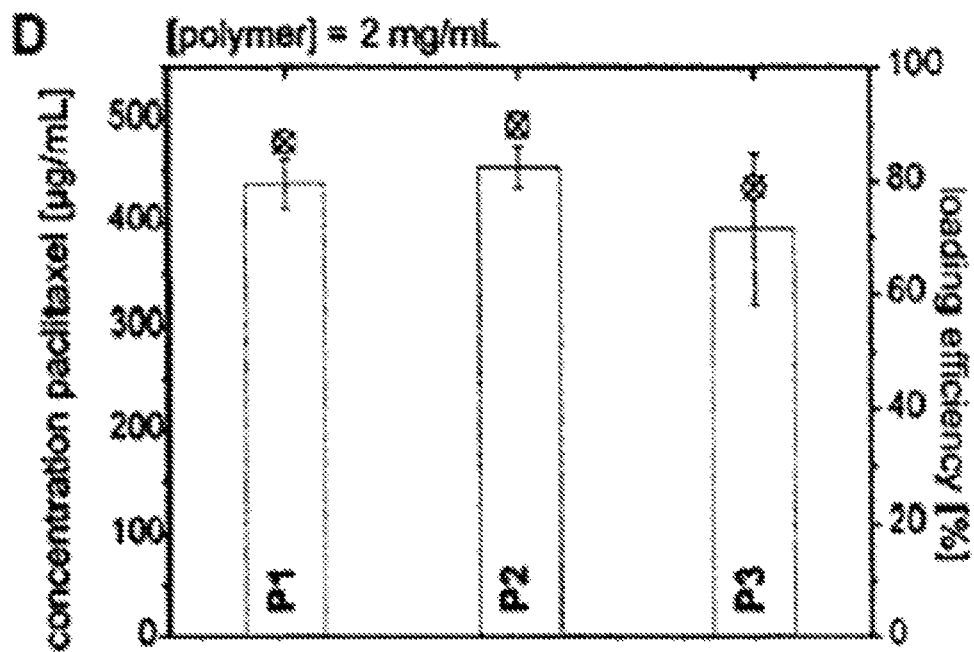
Figure 9A:
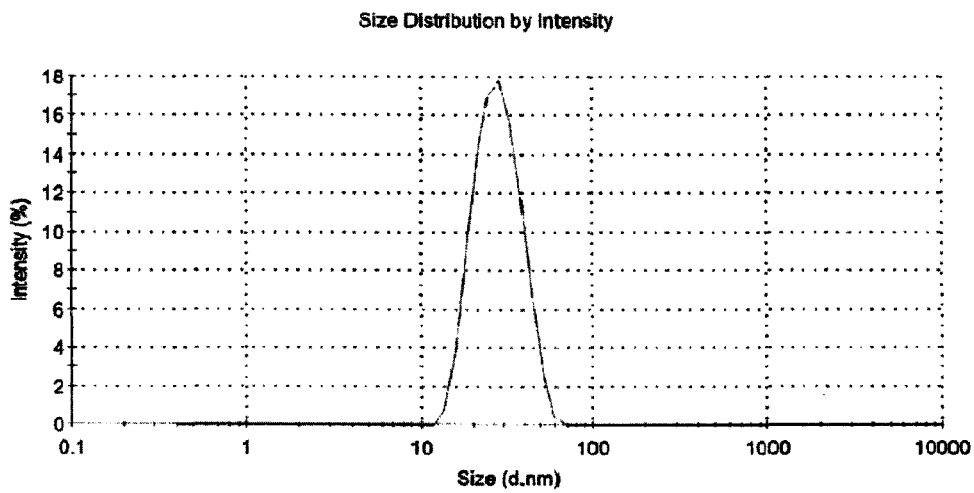
Figure 9B:
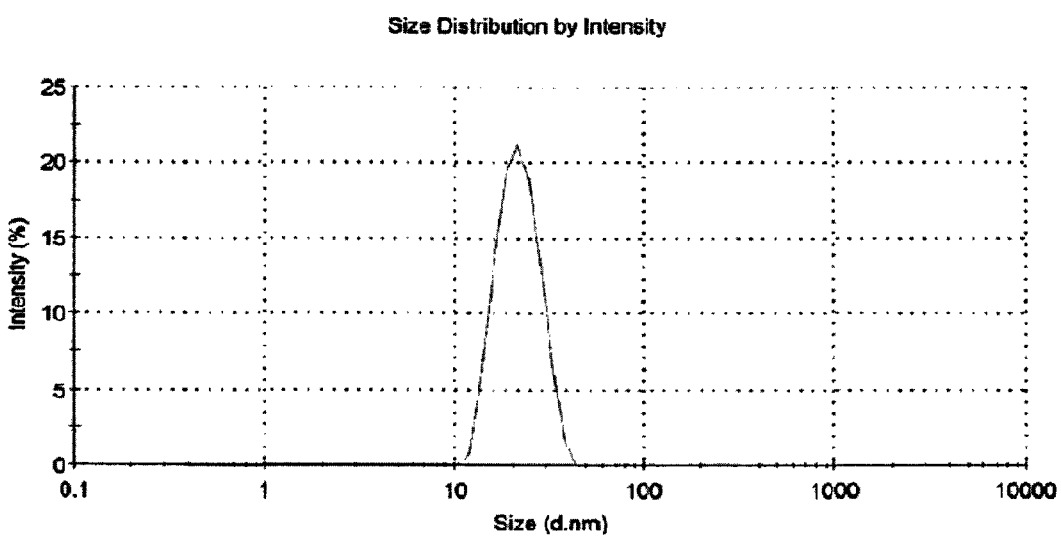
Figure 9C:
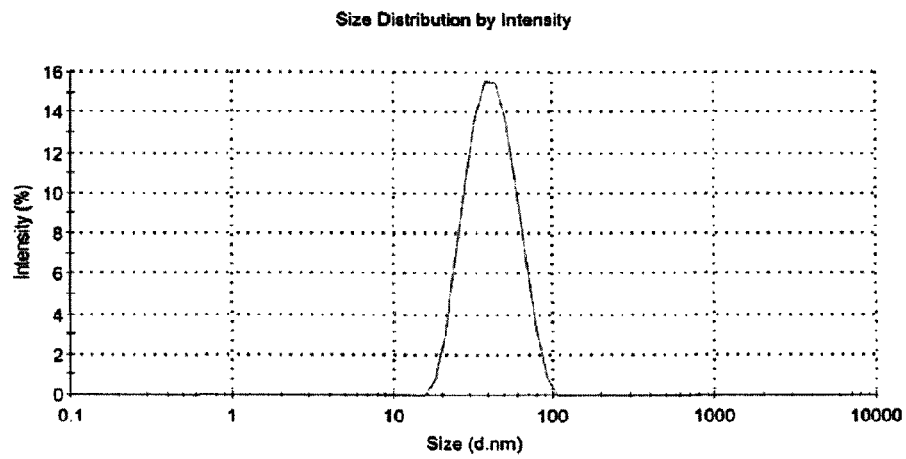
Figure 9D:
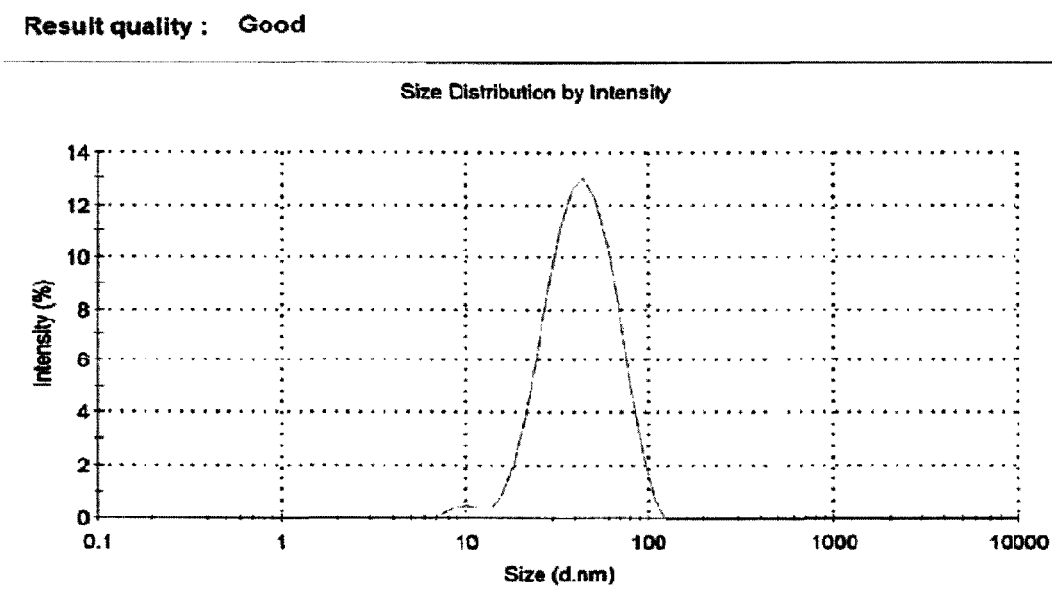

FIGS. 8A-8D show the solubilization of paclitaxel (PTX) with amphiphilic poly(2-oxazoline) block copolymers using the film method. In FIGS. A-D), solution concentration of PTX are shown as bars and loading efficiency is shown as crossed circles for different polymers and targeted PTX concentrations. FIG. 8A shows the solubilization of paclitaxel with P2 (10 mg/mL) and the loading efficiency for paclitaxel concentrations of 4 mg/mL, 7 mg/mL, and 10 mg/mL. FIG. 8B shows the solubilization of paclitaxel using P1-P4 (10 mg/mL) and the loading efficiencies at a paclitaxel concentration of 4 mg/mL. FIG. 8C shows the solubilization of paclitaxel with P3 (2 mg/mL) and the loading efficiency for paclitaxel concentrations of 100 μg/mL, 500 μg/mL and 1 mg/mL. FIG. 8D shows the solubilization of paclitaxel using P1-P3 (2 mg/mL) and the loading efficiencies at a paclitaxel concentration of 500 μg/mL. Data is presented as means±SEM (n=3 except for FIG. 8C for 1 mg/mL paclitaxel where n=1 and for FIG. 8B for P4 where n=2).

FIGS. 9A-9D provide dynamic light scattering plots of drug loaded micelles of P1 (FIG. 9A) and P2 (FIG. 9B) (10 mg/mL) with 4 mg/mL paclitaxel and unloaded micelles of P3 (5 mg/mL) in the presence (FIG. 9D) and absence (FIG. 9C) of 5 mg/mL BSA.

Figure 10A:
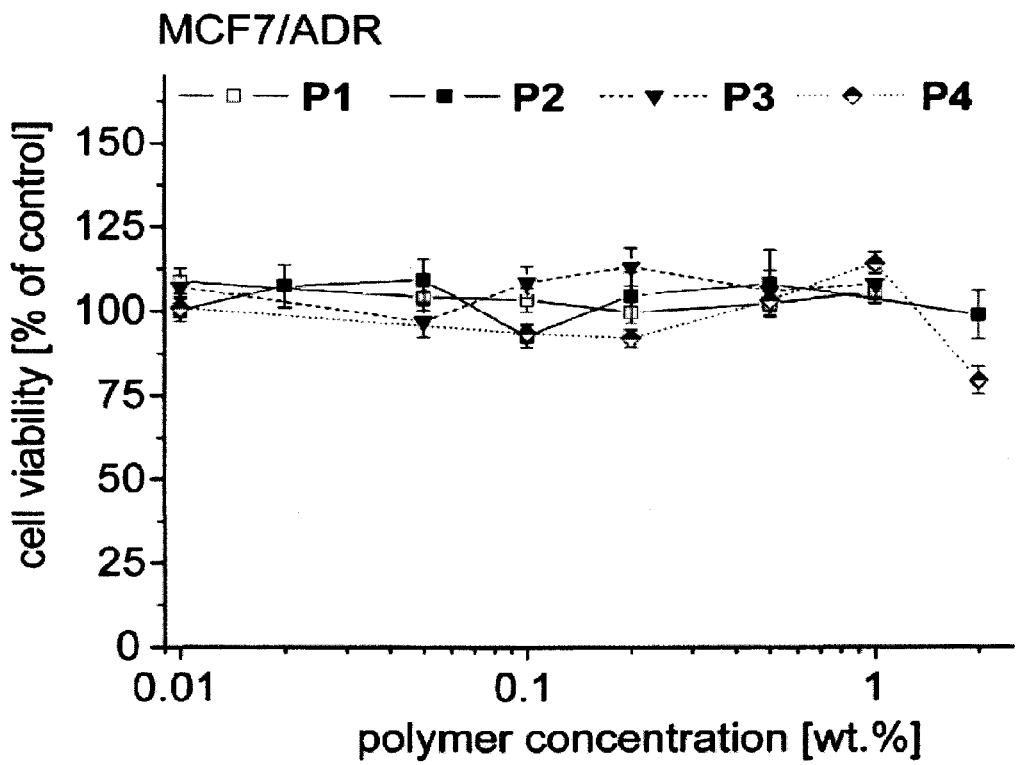
Figure 10B:
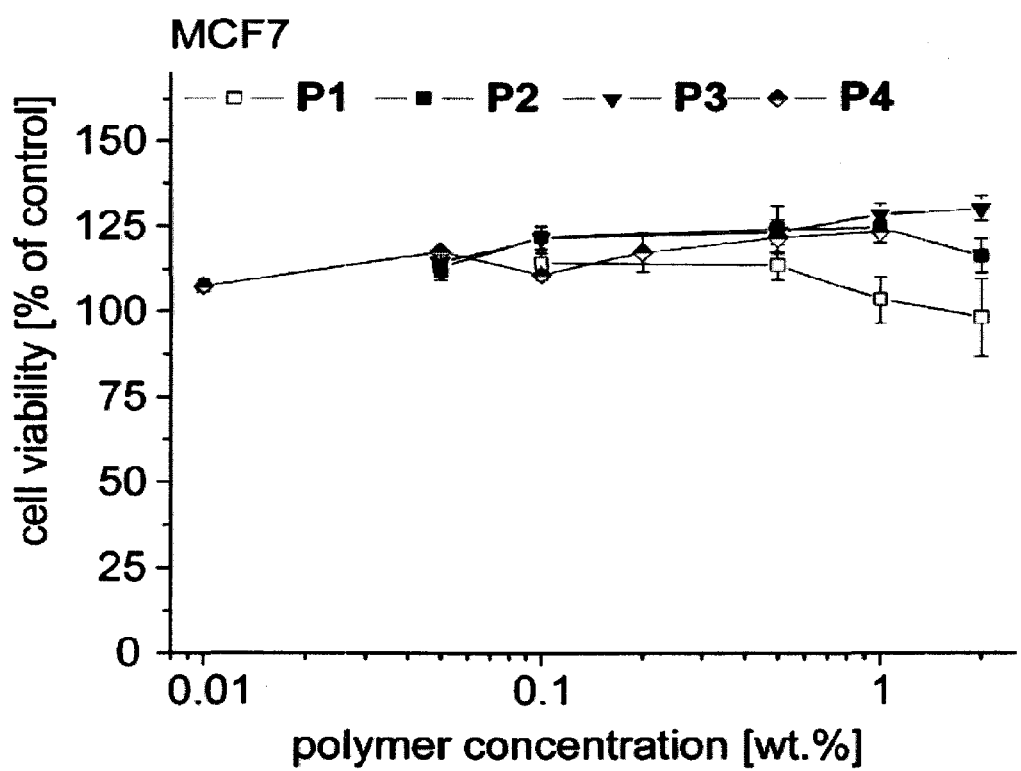
Figure 10C:
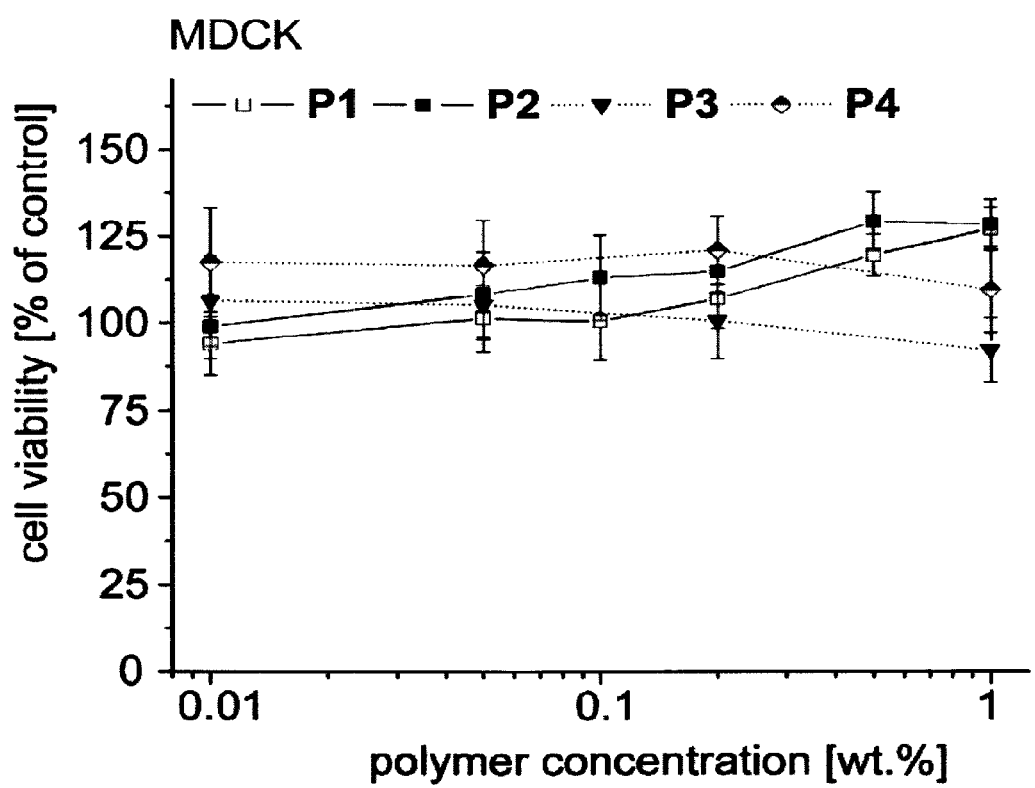

FIG. 10A is a graph of MCF7/ADR cell viability after 24 hour incubation with P1-P4 at concentrations of up to 20 mg/mL. FIGS. 10B and 10C are graphs of MCF7 and MDCK cell viability, respectively, after 2 hour incubation with P1-P4 at concentrations of up to 20 mg/mL. The data is presented as mean±SEM (n=4).

Figure 11A:
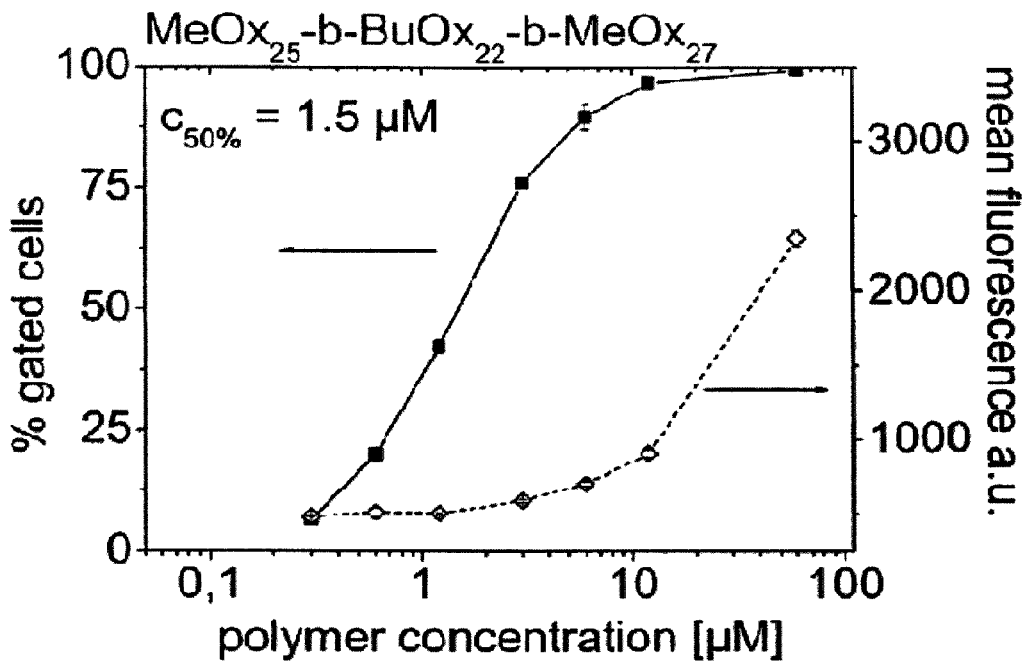
Figure 11B:
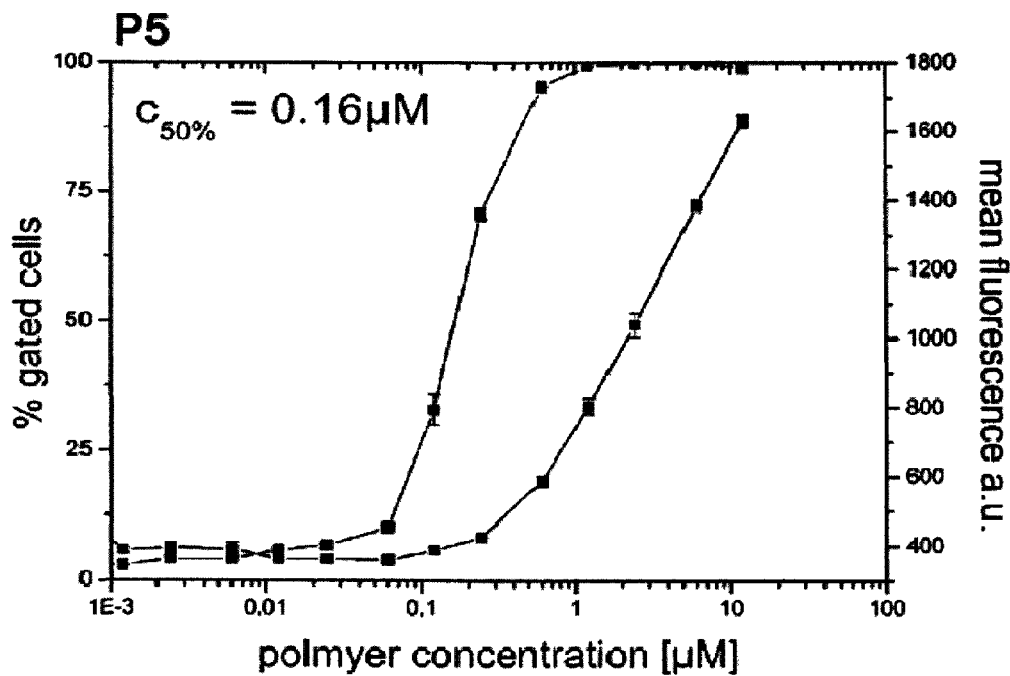
Figure 11C:
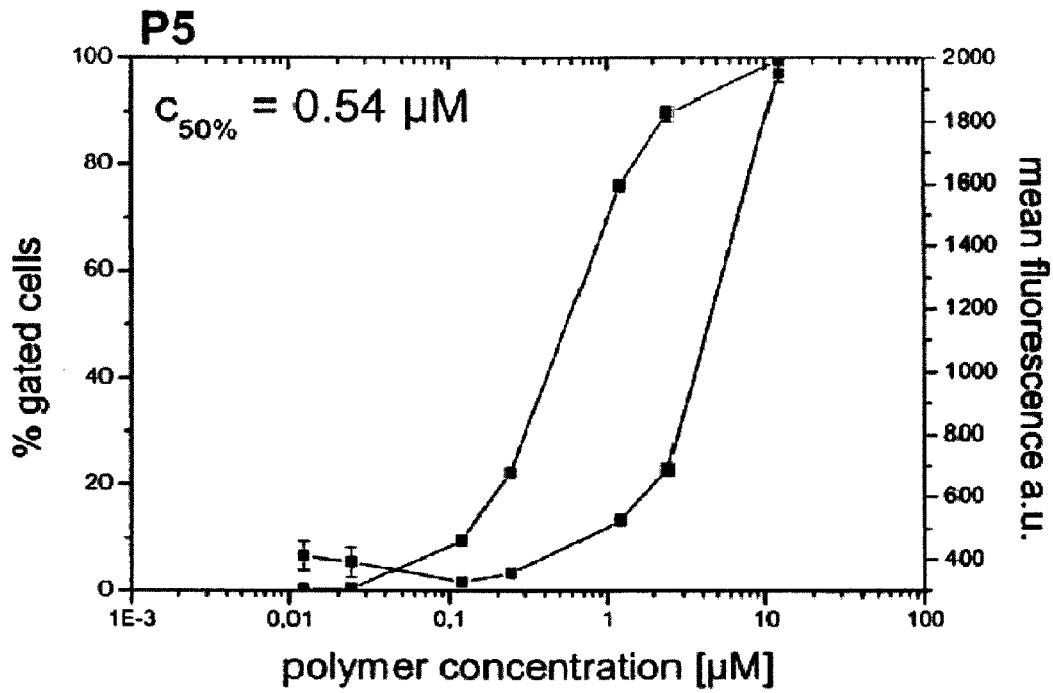
Figure 11D:
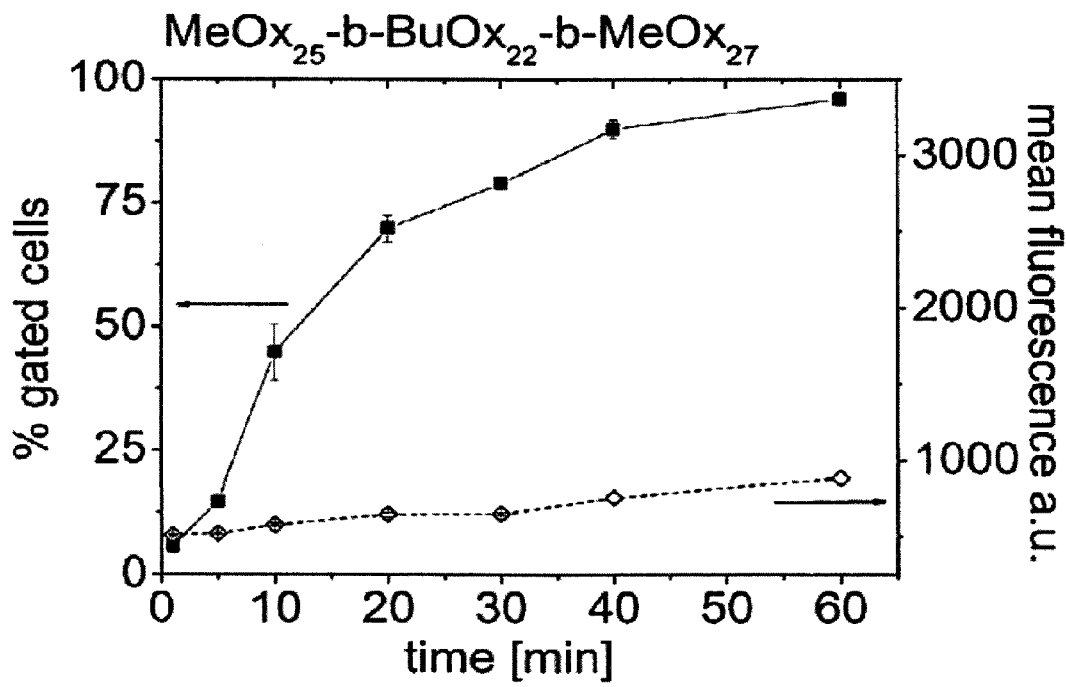
Figure 11E:
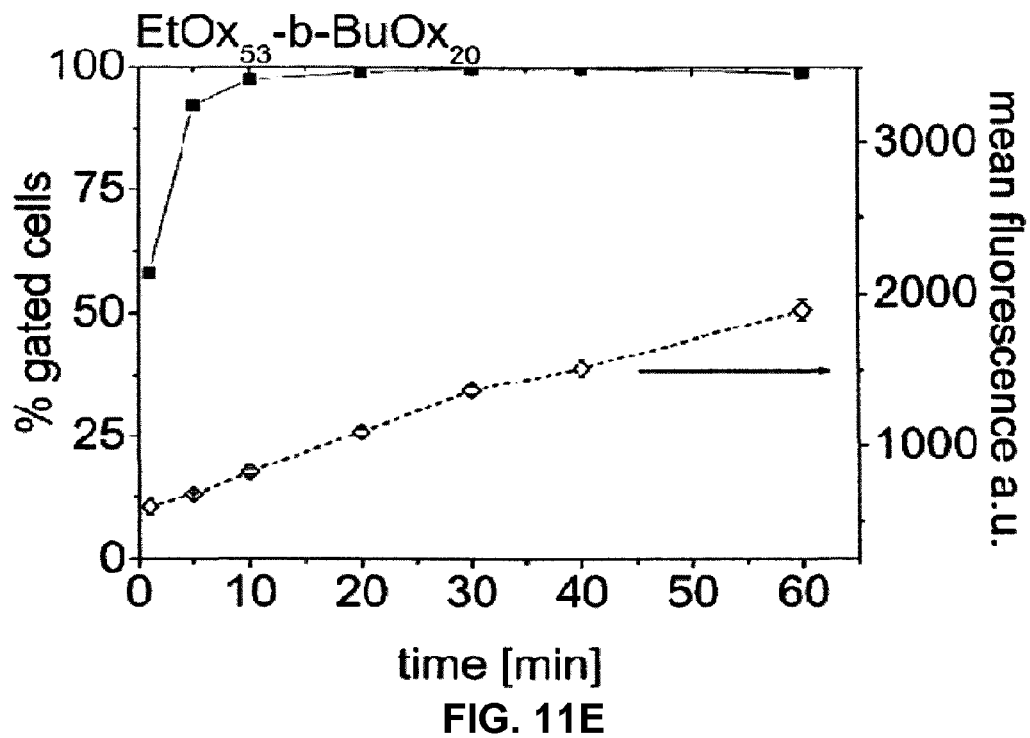
Figure 11F:
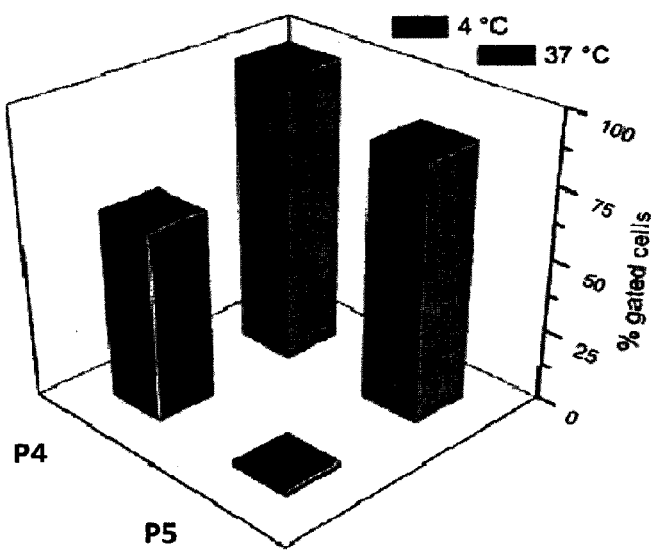

FIGS. 11A and 11B are graphs of flow cytometric analyses of MCF7/ADR cells after 60 minute incubation with Atto425-labeled P4 and P5, respectively, at 37° C. and various concentrations. FIG. 11C is a graph of a flow cytometric analysis of MCF7 cells after a 60 minute incubation with Atto425-labeled P5 at 37° C. and various concentrations. FIGS. 11D and 11E are graphs of flow cytometric analyses of MCF7/ADR cells after incubation for different time intervals with Atto425-labeled P4 and P5, respectively, at 37° C. FIG. 11F is a graph of a flow cytometric analysis of MCF7/ADR cells after incubation for 60 minutes with Atto425-labeled P4 at 37° C. and 4° C. at a concentration of 0.1 mg/mL.

Figure 12A:
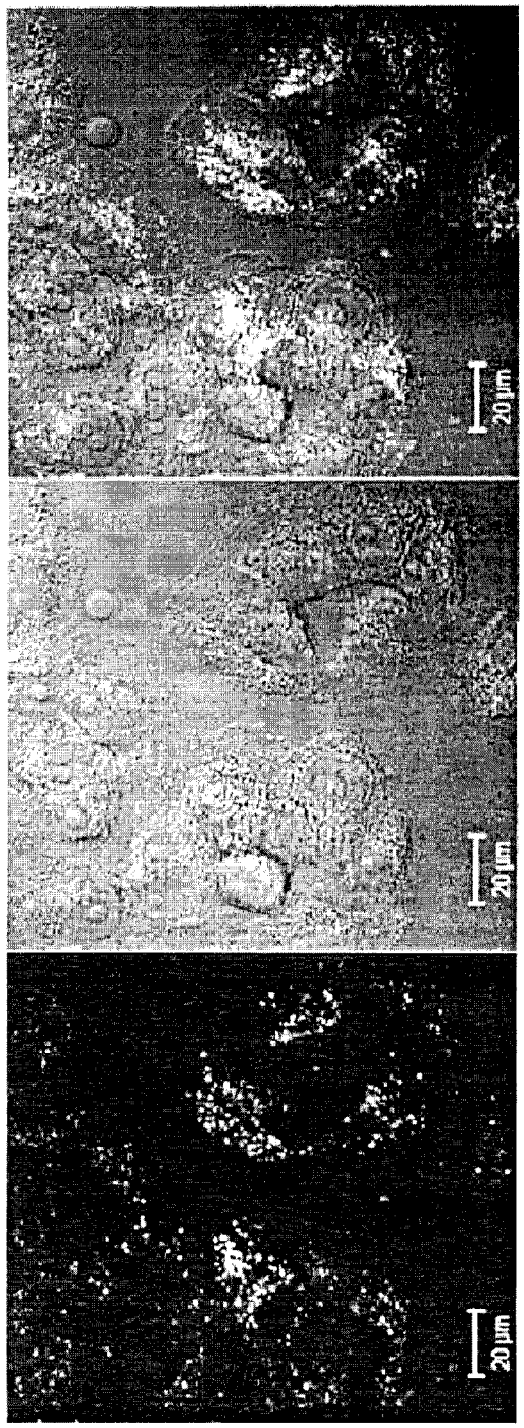
Figure 12B:
Figure 12C:
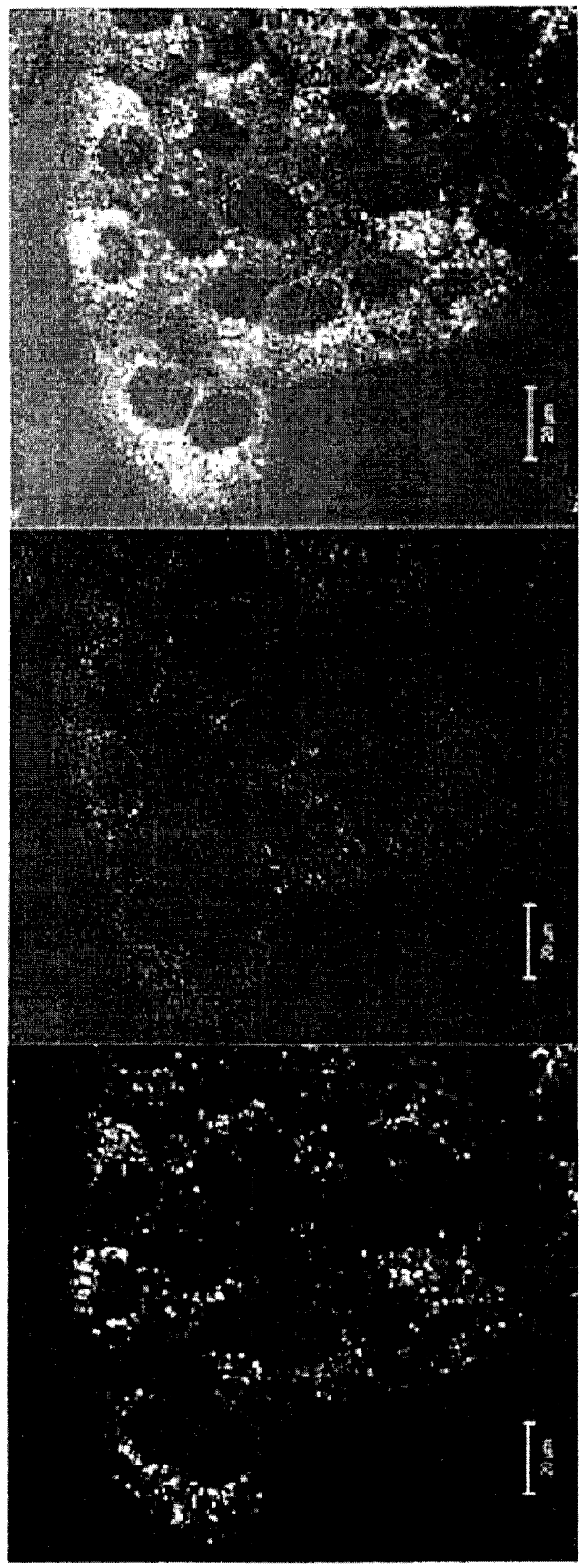
Figure 12D:
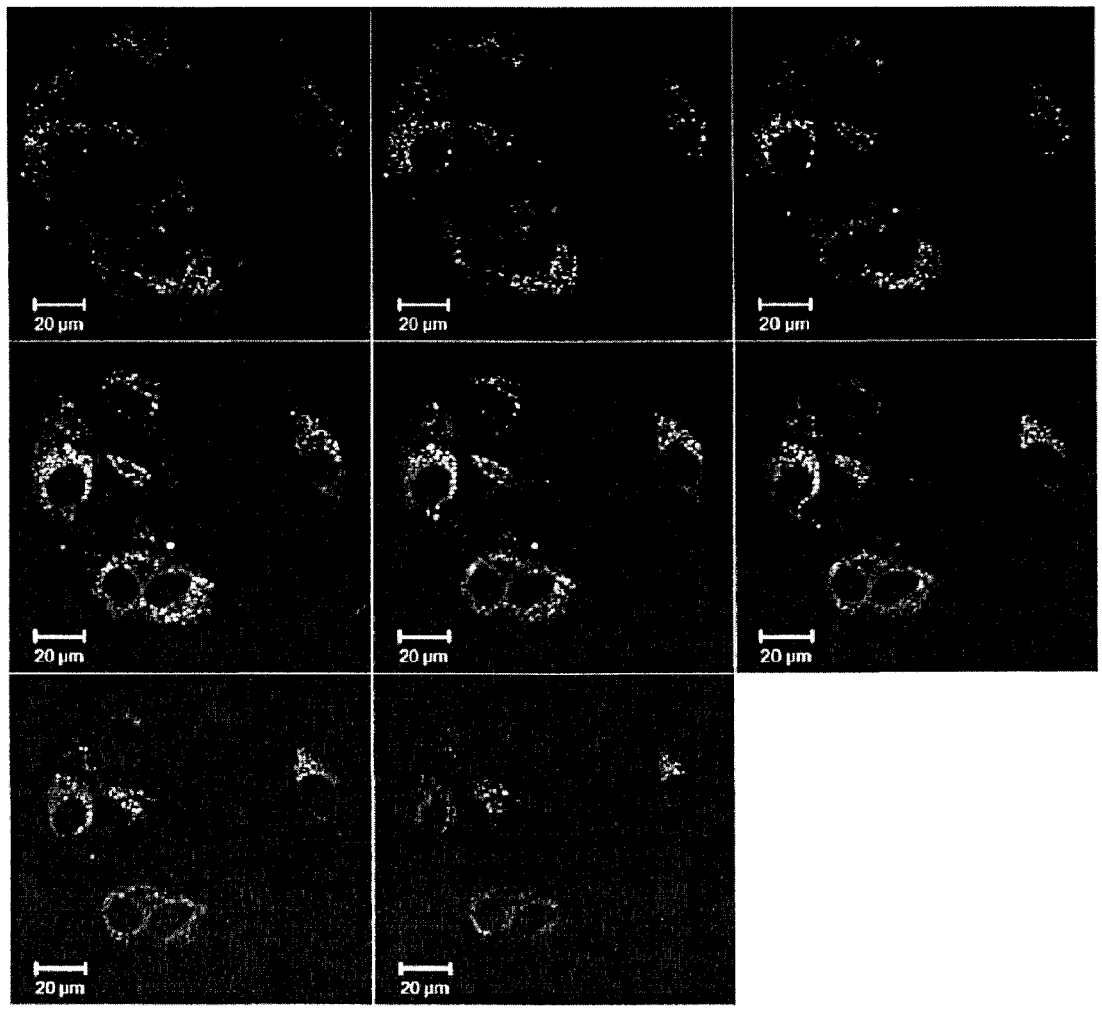
Figure 12E:
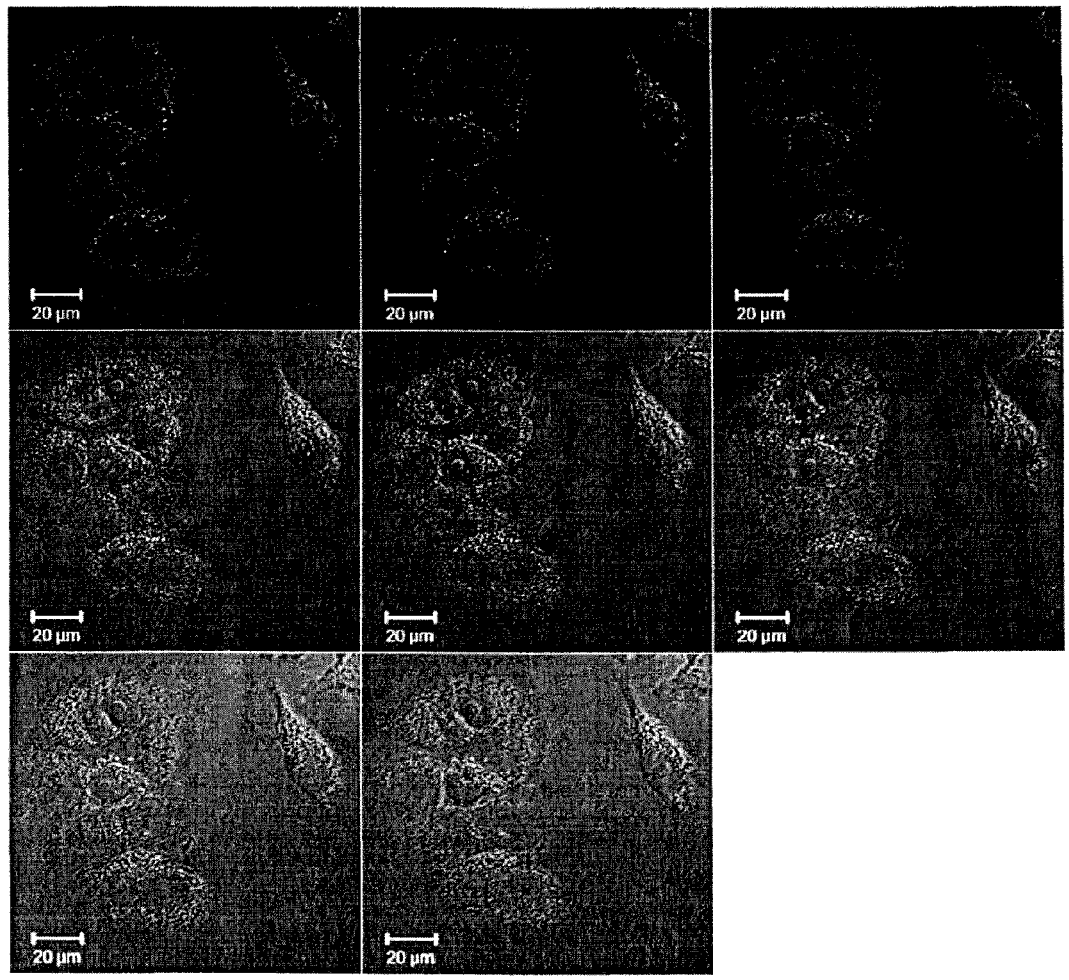
Figure 12F:
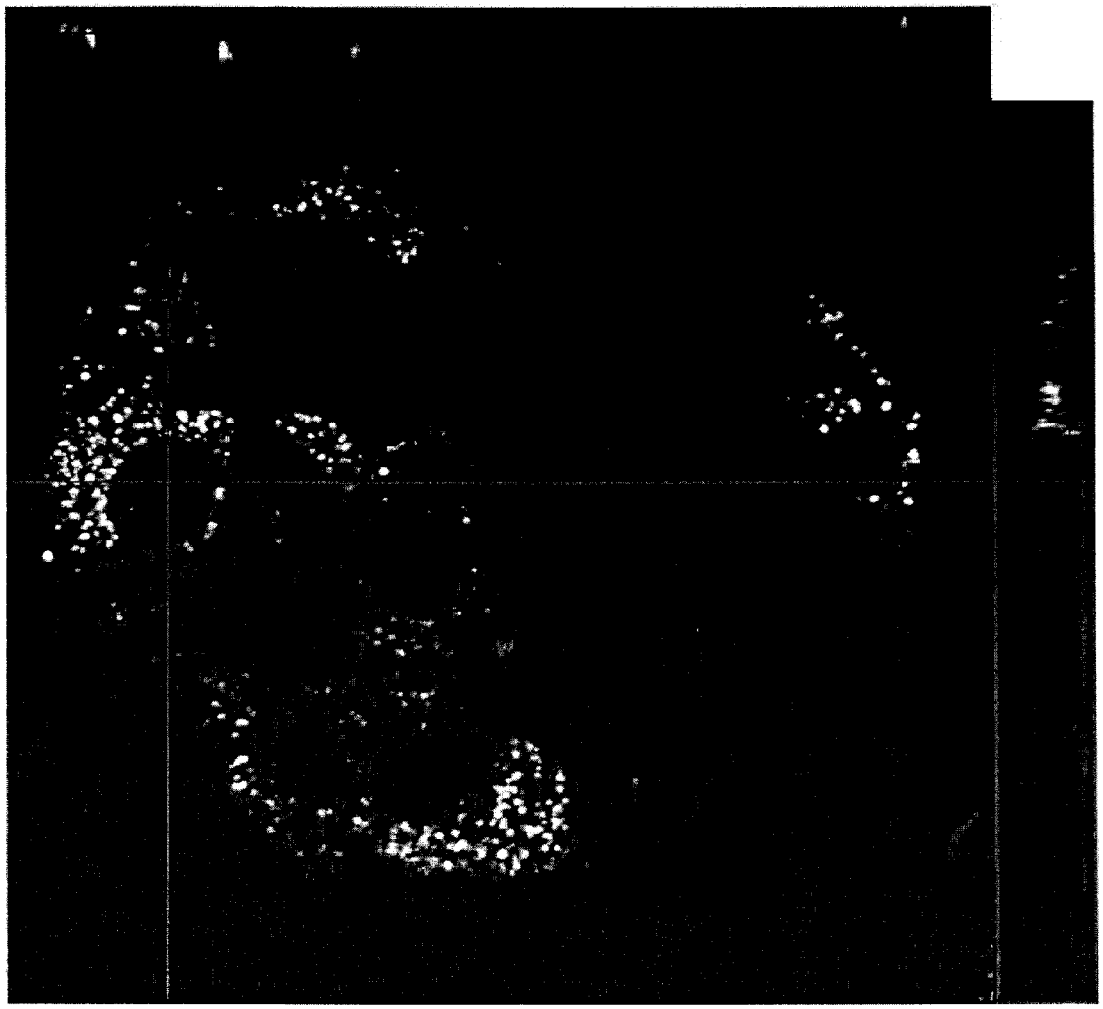

FIGS. 12A-12C are confocal micrographs of MCF7/ADR cells after a 5 minute (FIG. 12B) or 60 minute (FIGS. 12A and 12C) incubation with Atto425-labeled P4 (FIGS. 12B and 12C) or P5 (FIG. 12A) at 37° C. at a concentration of 0.2 mg/mL, $\lambda_{ex}$=405 nm, band pass filter 420/60 nm, magnification 63×. FIGS. 12D-12F provide a Z-stack obtained from confocal microscopy of MCF7/ADR cells after 5 minute incubation with Atto425-labeled P4 at 37° C. at a concentration of 0.2 mg/mL.

FIG. 12D represents blue fluorescence picture ($\lambda_{ex}$=405 nm, band pass filter 420/60 nm), FIG. 12E represents differential interference contrast (DIC), and FIG. 12F gives the orthogonal view of the same z-stack. Slices are separated by 1 μm, bars represent 20 μm, magnification 63×.

Figure 13A:
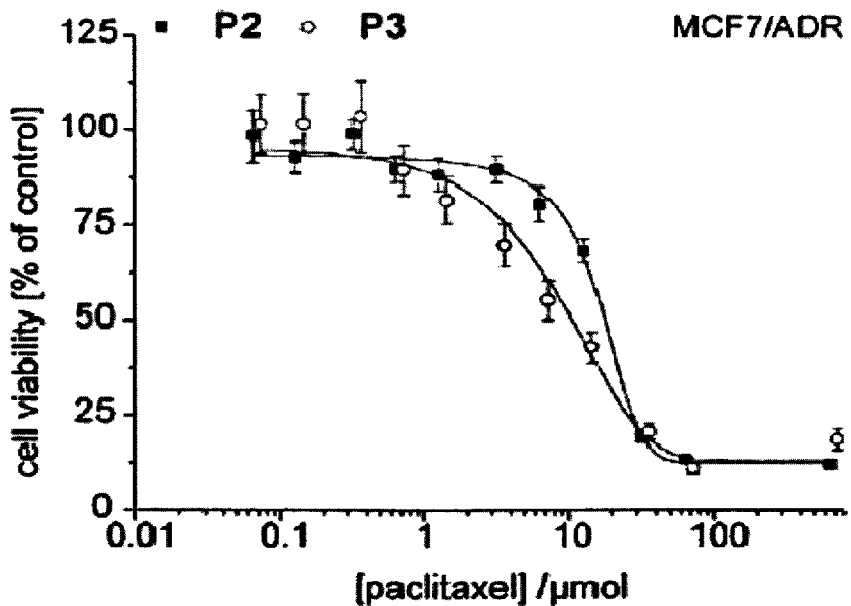
Figure 13B:
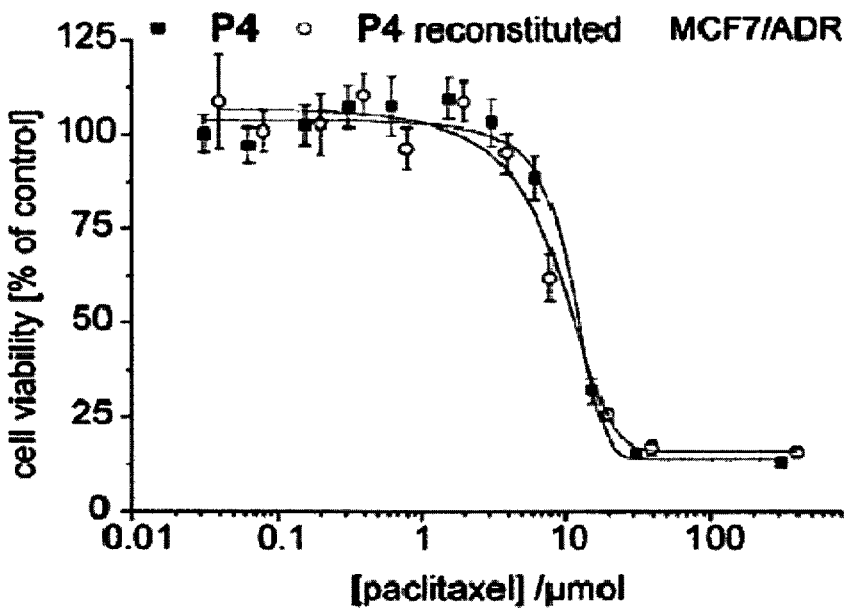

FIGS. 13A-13B demonstrate paclitaxel dose dependent viability of multi-drug resistant MCF7/ADR cells. FIG. 13A provides a comparison of P2 and P3 formulated paclitaxel. FIG. 13B demonstrates no change in paclitaxel activity is observed after freeze-drying and reconstitution in deionized water (shown here with P4). The data is presented as mean±SEM (n=3).

FIG. 14 shows relative tumor weights (FIG. 14A) and tumor inhibition (FIG. 14B) in mice comparing negative controls, treatment with compositions according to the invention, and a commercial product.

FIG. 15A provides a reaction scheme for a preparation of star-block copolymers. FIG. 15B provides a schematic of a preparation of a bi-functional initiator for the two step preparation of triblock copolymers (Witte et al. (1974) Lie-bigs Ann. Chem., 6:996; Kobayashi et al. (1987) Macromol., 20:1729).

DETAILED DESCRIPTION OF THE INVENTION

The instant invention allows for the solubilization of compounds (e.g., hydrophobic drugs) in aqueous solutions (e.g., water, blood). A number of highly potent drugs are not soluble in water and are, therefore, difficult to deliver to the human body. The instant invention utilizes highly water soluble and nontoxic polymers to incorporate these kinds of drugs (e.g., paclitaxel) into micelles formed by the polymer. The presence of the polymers increases the solubility in water and aqueous solutions by orders of magnitude. This allows for largely increased dose administration to patients and would be particularly beneficial in the treatment of various diseases such as cancer.

As stated above, a wide variety of highly active drugs suffer from very low solubility in aqueous media. This is a major limitation in their use as orally or intravenously administered drugs. Numerous polymers, in particular amphiphilic block copolymers have been studied in order to find a suitable polymer carrier system for hydrophobic drugs. In particular, solubilization of the hydrophobic macrocycle paclitaxel (solubility in water approx. 0.3 μg/ml), widely used in cancer chemotherapy has been investigated herein. ABA-type block copoly(2-oxazoline)s (also termed poly(N-acetyl-ethylenimine)s) of the instant invention consisting of hydrophilic A blocks (e.g., 2-methyl-2-oxazoline) and hydrophobic B blocks (e.g., consisting of 2-butyl-2-oxazoline or 2-nonyl-2-oxazoline) are extraordinarily well suited to solubilize high amounts of paclitaxel in aqueous media at physiologically relevant pH.

Only a quite limited number of types of polymers are widely recognized as suitable for a wide range of biomedical materials. Problems with these polymers include a lack of chemical and structural versatility and definition. Poly(2-oxazoline)s are a very valuable novel alternative for biomedical materials in general and as drug carriers in particular. The defined cationic ring opening polymerization reaction and chemical versatility of poly(2-oxazoline)s allows for very exact tuning of their solubility, their thermal responsiveness (LCST), and their aggregation behavior in aqueous solutions. Depending on the side chain, poly(2-oxazoline)s or poly(2-oxazoline) blocks can be extremely hydrophilic, amphiphilic, hydrophobic, or fluorophilic. Additionally, a wide range of side chain moieties have been introduced, including carboxylic acids, amines, aldehydes, alkynes and thiols. These allow a wide range of specific coupling reactions (chemoselective ligations) with bioactive compounds, e.g. peptides or drugs. In addition, multi-block, star-like, and star-like block copolymers may be synthesized.

The preparation of compound (e.g., paclitaxel) loaded poly (2-oxazoline) loaded micelles is facile via a thin film method. Briefly, both polymer and the drug (e.g., paclitaxel) are dissolved in acetonitrile, a common solvent for both compounds. The solvent is removed in a stream of gas (nitrogen or air). In order to remove possible residual solvent, the films are subjected to vacuum (approx. 0.2 mbar) overnight or at least three hours. Subsequently, the desired aqueous media is added (e.g., water or pH 7.4 buffer solution such as phosphate buffered saline) and the polymer drug film is solubilized by vortexing or gentle shaking. At certain drug-polymer ratios, solubilization is facilitated at 37° C. After filtration (pore size 0.22-0.45 μm) to remove eventually non-dissolved paclitaxel particles or precipitated drug-polymer aggregates, the aqueous micellar drug formulation can be analyzed to determine the final drug concentration by high performance liquid chromatography (HPLC). The HPLC analysis was performed under isocratic conditions with a solvent mixture of 45% water and 55% acetonitrile and the amount of paclitaxel was determined using a calibration curve.

It is shown herein that various poly(2-oxazoline)s, differing in molecular weight, polymer architecture, and block lengths, are excellent solubilizers for drugs such as paclitaxel at polymer concentrations ranging from 0.2 wt % to 1% wt. and paclitaxel concentrations up to 8.3 mg/ml in 1 wt. % polymer solutions (10 mg/ml) can be obtained. This value is about 28,000 times the normal solubility of paclitaxel in water and greatly exceeds any solubilization potential in comparable polymer concentrations in aqueous solutions of any compound. The final loading capacity of the micelles was thus as high as 45% (w/w). Sizes of the drug-polymer micelles vary depending on the drug loading and the polymer used, but are typically found around 20-23 nm with very narrow size distribution (PDI≤0.1). This size range is well suited for intravenous administration. The size of the formed particles was also confirmed by atomic force microscopy.

Furthermore, these formulations were investigated towards their behavior after freeze drying and reconstitution in water. It was found that this process did not alter the amount of paclitaxel found and also the size of the aggregates did not change significantly. Such characteristics are preferable for commercialization since it is desirable to supply dry powders as opposed to micellar solutions, which are much more likely to undergo aging processes. Importantly, the incorporated drug retains its toxicity towards cancer cells. This is in stark contrast to other polymers which have failed to properly release the incorporated drug and renders the incorporated drug inactive.

These results are unexpected as 2-oxazoline polymers were not designed for drug formulations and most 2-oxazoline polymers have a relatively high overall hydrophilicity. Moreover, during measurements for the critical micellar concentration (CMC) by pyrene probe assay, it was determined that the micellar core forms a relatively polar environment. It was not expected that a polar and well hydrated micellar core would incorporate significant amounts of highly hydrophobic drug.

In addition to paclitaxel, other relevant hydrophobic drugs which significantly vary in their chemical nature have been successfully incorporated in these micelles. For example, cyclosporine A (a cyclic peptide and powerful immunosuppressant) and amphotercin B (a polyene polyole macrolactone (an antifungal agent which can be used against systemic fungal infections in immunocompromised patients)) have been incorporated into the polymers of the instant invention.

The described invention utilizes less material to solubilize the same amount of bioactive substance, e.g., paclitaxel. While a 10% solution (v/v) of Cremophor EL®/EtOH is needed to solubilize 600 μg/mL paclitaxel in aqueous solution, this is possible to achieve with only a 0.2% solution (w/w) of the described polymers. This significantly reduces the additional load of substances given to patients and is expected to minimize eventual side effects. Additionally, reduced side effects will occur because the polymers described in this invention are not known to be toxic or hazardous in any way in a relevant concentration range. Furthermore, the described paclitaxel-poly(2-oxazoline) formulations are easy to prepare and can be freeze-dried and easily reconstituted by addition of the desired parenteral administration solution (e.g., saline for i.v. injection). Storage as a solid also typically enhances shelf-life of bioactive components.

Highly water soluble, well-defined poly(2-methyl-2-oxazoline) and poly(2-ethyl-2-oxazoline) polymers have been shown to not undergo unspecific accumulation in a host and the polymers are very rapidly excreted via the kidneys in the mouse. Furthermore, no cytotoxicity in various cell types of human, canine, and murine origin has been generally observed, even at very high concentrations of up to 20 mg/mL. Concentration, time and temperature dependent studies of cellular uptake reveal that, depending on then polymer structure, the cellular uptake can occur extremely fast and very efficiently, even at very low concentrations. Furthermore, the cellular uptake of poly(2-oxazoline)s is typically energy dependent, as at 4° C. no cellular uptake was observed for most polymer structures. In conclusion, the structural and chemical versatility of poly(2-oxazoline)s, together with their excellent biocompatibility, make this class of polymer ideal for delivering drugs and biomaterials.

Surprisingly, it has been demonstrated herein that biocompatible, water soluble polymers comprising at least one hydrophobic block of poly(2-oxazoline)s with hydrophobic side chains form compositions with large amounts of highly hydrophobic drugs (40% w/w), even at polymer concentrations as low as 0.2% (w/v).

I. DEFINITIONS

The following definitions are provided to facilitate an understanding of the present invention:

As used herein, the term "lipophilic" refers to the ability to dissolve in lipids. "Hydrophobic" designates a preference for apolar environments (e.g., a hydrophobic substance or moiety is more readily dissolved in or wetted by non-polar solvents, such as hydrocarbons, than by water).

"Hydrophilic" designates a preference of a substance or moiety for aqueous environments, i.e. a hydrophilic substance or moiety is more readily dissolved in or wetted by water than by non-polar solvents, such as hydrocarbons. In preferred embodiments, the term "hydrophilic" may mean the ability to dissolve in water.

As used herein, the term "amphiphilic" means the ability to dissolve in both water and lipids/apolar environments. Typically, an amphiphilic compound comprises a hydrophilic portion and a lipophilic (hydrophobic) portion. In other words, the term "amphiphilic" denotes the simultaneous presence of hydrophilic and less hydrophilic or more hydrophobic moieties in a compound, as frequently encountered in surfactants. To that extent, the copolymers used in the context of the invention are also referred to herein as amphiphilic copolymers since they comprise hydrophilic moieties and moieties which are less hydrophilic/more hydrophobic, respectively.

As used herein, the term "biocompatible" refers to a substance which produces no significant untoward effects when applied to, or administered to, a given organism.

As used herein, aqueous environments, aqueous media, aqueous solutions or the like refer to solvent systems wherein 50% (v/v) or more, preferably 70% or more, more preferably 90% or more and in particular substantially 100% of the total volume of solvent(s) is water.

As used herein, the term "polymer" denotes molecules formed from the chemical union of two or more repeating units or monomers.

The term "block copolymer" most simply refers to conjugates of at least two different polymer segments, wherein each polymer segment comprises two or more adjacent units of the same kind. In other words, the term "block copolymer" is used herein in accordance with its established meaning in the art to refer to copolymers wherein repeating units of a defined type are organized in blocks, i.e. repeating units of the same type are polymerized sequentially adjacent to each other as opposed to, for example, sequences of randomly alternating repeating units of different types. In other words, the blocks of a block copolymer, such as blocks A and B to be further discussed below, represent polymeric entities themselves, obtained by the polymerization of monomers which are identical or which have certain common characteristics.

The expression "drug load" means the ratio of the weight of the bioactive agent to the sum of the weights of the bioactive agent and the block copolymer×100 expressed as a percentage.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

"Polypeptide" and "protein" are sometimes used interchangeably herein and indicate a molecular chain of amino acids. The term polypeptide encompasses peptides, oligopeptides, and proteins. The terms also include post-expression modifications of the polypeptide, for example, glycosylations, acetylations, phosphorylations and the like. In addition, protein fragments, analogs, mutated or variant proteins, fusion proteins and the like are included within the meaning of polypeptide.

The term "isolated" may refer to protein, nucleic acid, compound, or cell that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), antioxidant (e.g., ascorbic acid, sodium metabisulfite), solubilizer (e.g., Tween 80, Polysorbate 80), emulsifier, buffer (e.g., Tris HCl, acetate, phosphate), bulking substance (e.g., lactose, mannitol), excipient, auxiliary agent, filler, disintegrant, lubricating agent, binder, stabilizer, preservative or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. The compositions can be incorporated into particulate preparations of polymeric compounds such as polylactic acid, polyglycolic acid, etc., or into liposomes or micelles. Such compositions may influence the physical state, stability, rate of in vivo release, and rate of in vivo clearance of components of a pharmaceutical composition of the present invention. The pharmaceutical composition of the present invention can be prepared, for example, in liquid form, or can be in dried powder form (e.g., lyophilized). Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, 20th Edition, (Lippincott, Williams and Wilkins), 2000; Liberman, et al., Eds., Pharmaceutical Dosage Forms, Marcel Decker, New York, N.Y., 1980; and Kibbe, et al., Eds., Handbook of Pharmaceutical Excipients (3rd Ed.), American Pharmaceutical Association, Washington, 1999.

The term "alkyl," as employed herein, includes both straight and branched chain hydrocarbons containing about 1 to about 50 carbons, about 1 to about 20, about 1 to about 15, or about 1 to about 10 carbons in the main chain. The hydrocarbon chain may be saturated or unsaturated (i.e., comprise double and/or triple bonds). The hydrocarbon chain may also be cyclic or comprise a portion which is cyclic. The hydrocarbon chain of the alkyl groups may be interrupted with heteroatoms such as oxygen, nitrogen, or sulfur atoms. Each alkyl group may optionally be substituted with substituents which include, for example, alkyl, halo (such as F, Cl, Br, I), haloalkyl (e.g., $CCl_3$ or $CF_3$), alkoxyl, alkylthio, hydroxy, methoxy, carboxyl, oxo, epoxy, alkyloxycarbonyl, alkylcarbonyloxy, amino, carbamoyl (e.g., $NH_2C(=O)$— or $NHRC(=O)$—, wherein R is an alkyl), urea (—$NHCONH_2$), alkylurea, aryl, ether, ester, thioester, nitrile, nitro, amide, carbonyl, carboxylate and thiol. Examples of simple alkyls include, without limitation, propyl, butyl, pentyl, hexyl, heptyl, octyl and nonyl.

The term "aryl," as employed herein, refers to monocyclic and bicyclic aromatic groups containing 6 to 10 carbons in the ring portion. Aryl groups may be optionally substituted through available carbon atoms. The aromatic ring system may include heteroatoms such as sulfur, oxygen, or nitrogen.

The term "patient" as used herein refers to human or animal subjects.

The term "cancer", in accordance with the present invention refers to a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system).

The term "neurodegenerative disease", in accordance with the present invention refers to a class of diseases or disorders wherein neurons deteriorate and due to the inability of the body to regenerate neurons (except a small number neural stem cells) the cells for example of the brain or spinal chord cannot be adequately regenerated. Symptoms encompass ataxia as well as dementia in affected individuals.

The term "gastrointestinal and hepato-biliary disease", in accordance with the present invention relates to diseases or disorders affecting the liver, gall bladder and bile ducts. Such diseases and disorders include, for example, cirrhosis, hepatitis, virally induced hepatitis, liver tumors, fatty liver, polycystic liver, Morbus Crohn, Colitis ulcerosa and cholangiocarcinoma.

The term "cardiovascular disease", in accordance with the present invention relates to a class of diseases or disorders involving the heart an/or blood vessels.

The term "pulmonary diseases", as used in accordance with the present invention relates to diseases affecting the respiratory system and can be classified into obstructive, i.e. impeding the rate of low into and out of the lungs, and restrictive, i.e. reduction in the functional volume of the lungs, conditions. Such diseases include, for example, asthma, bronchitis, asbestosis, fibrosis, sarcoidosis, lung cancer, pneumonia, pulmonary edema and pulmonary hypertension.

II. POLYMER

In a preferred embodiment of the instant invention, the synthetic polymers of the complexes are block copolymers. More specifically, the synthetic polymers are block copolymers which comprise at least one hydrophilic polymer segment and at least one hydrophobic (lipophilic) polymer segment. Block copolymers are most simply defined as conjugates of at least two different polymer segments (Tirrel, M. In: Interactions of Surfactants with Polymers and Proteins. Goddard E. D. and Ananthapadmanabhan, K. P. (eds.), CRC Press, Boca Raton, Ann Arbor, London, Tokyo, pp. 59-122, 1992). The simplest block copolymer architecture contains two segments joined at their termini to give an A-B type diblock. Consequent conjugation of more than two segments by their termini yields A-B-A type triblock, A-B-A-B-type multiblock, or even multisegment A-B-C-architectures. If a main chain in the block copolymer can be defined in which one or several repeating units are linked to different polymer segments, then the copolymer has a graft architecture of, e.g., an $A(B)_n$ type. More complex architectures include for example $(AB)_n$ (wherein m is about 1 to about 100) or $A_nB_m$, starblocks which have more than two polymer segments linked to a single center. An exemplary block copolymer of the instant invention has the formula A-B or B-A, wherein A is a hydrophilic polymer segment and B is a hydrophobic polymer segment. Another exemplary block copolymer has the formula A-B-A. Block copolymers structures include, without limitation, linear copolymers, star-like block copolymers, graft block copolymers, dendrimer based copolymers, and hyperbranched (e.g., at least two points of branching) block copolymers. The segments of the block copolymer may have from about 2 to about 1000, about 2 to about 300, or about 2 to about 100 repeating units or monomers.

Well-defined poly(2-oxazoline) block copolymers of the instant invention may be synthesized by the living cationic ring-opening polymerization of 2-oxazolines. The synthetic versatility of poly(2-oxazoline)s allows for a precise control over polymer termini and hydrophilic-lipophilic balance (HLB). Block length, structure, charge, and charge distribution of poly(2-oxazoline)s may be varied. For example, the size of the hydrophilic and/hydrophobic blocks may be altered, triblock polymers may be synthesized, star-like block copolymers may be used, polymer termini may be altered, and ionic side chains and/or ionic termini may also be incorporated. Ionic side chains (e.g., comprising —R—$NH_2$ or R—COOH, wherein R is an alkyl) may be incorporated into the hydrophilic (preferably) or hydrophobic block.

Poly(2-oxazoline)s (also known as 2-substituted 4,5-dihydro oxazoles) are polysoaps and depending on the residue at the 2-position of the monomer can be hydrophilic (e.g., methyl, ethyl) or hydrophobic (e.g. propyl, pentyl, nonyl, phenyl, and the like) polymers. Moreover, numerous monomers introducing pending functional groups are available (Taubmann et al. (2005) Macromol. Biosci., 5:603; Cesana et al. (2006) Macromol. Chem. Phys., 207:183; Lux-enhofer et al. (2006) Macromol., 39:3509; Cesana et al. (2007) Macromol. Rapid Comm., 28:608). Poly(2-oxazoline)s can be obtained by living cationic ring-opening polymerization (CROP), resulting in well-defined block copolymers and telechelic polymers of narrow polydispersities (Nuyken, et al. (1996) Macromol. Chem. Phys., 197:83; Persigehl et al. (2000) Macromol., 33:6977; Kotre et al. (2002) Macromol. Rapid Comm., 23:871; Fustin et al. (2007) Soft Matter, 3:79; Hoogenboom et al. (2007) Macromol., 40:2837). Several reports suggest that hydrophilic poly(2-oxazoline)s are essentially non-toxic and biocompatible (Goddard et al. (1989) J. Control. Release, 10:5; Woodle et al. (1994) Bioconjugate Chem., 5:493; Zalipsky et al. (1996) J. Pharm. Sci., 85:133; Lee et al. (2003) J. Control. Release, 89:437; Gaertner et al. (2007) J. Control. Release, 119:291). Using lipid triflates or pluritriflates, lipopolymers (Nuyken, et al. (1996) Macromol. Chem. Phys., 197:83; Persigehl et al. (2000) Macromol., 33:6977; Kotre et al. (2002) Macromol. Rapid Comm., 23:871; Fustin et al. (2007) Soft Matter, 3:79; Hoogenboom et al. (2007) Macromol., 40:2837; Punucker et al. (2007) Soft Matter, 3:333; Garg et al. (2007) Biophys. J., 92:1263; Punucker et al. (2007) Phys. Rev. Lett., 98:078102/1; Luedtke et al. (2005) Macromol. Biosci., 5:384; Purmcker et al. (2005) J. Am. Chem. Soc., 127:1258) or star-like poly(2-oxazoline)s (FIG. 15A) are readily accessible. Additionally, various poly(2-oxazoline)s with terminal quaternary amine groups have been reported, which interact strongly with bacterial cell membranes (Waschinski et al. (2005) Macromol. Biosci., 5:149; Waschinski et al. (2005) Biomacromol., 6:235).

In a particular embodiment, the biocompatible, water soluble copolymer of the instant invention comprises at least one hydrophilic block A and at least one hydrophobic block B. The at least one hydrophilic block A and at least one hydrophobic block B are attached through linkages which are stable or labile (e.g., biodegeradable under physiological conditions (e.g., by the action of biologically formed entities which can be enzymes or other products of the organism)). Although the hydrophilic block of the polymer preferably comprises at least one poly(2-oxazoline), the hydrophilic block may also comprise at least one polyethyleneoxide, polyester, or polyamino acid (e.g. poly(glutamic acid) or poly(aspartic acid)) or block thereof. The hydrophobic block may comprise a hydrophobic poly(2-oxazoline). Examples of hydrophilic poly(2-oxazoline)s include, without limitation, 2-methyl-2-oxazoline, 2-ethyl-2-oxazoline, and mixtures thereof. The degree of polymerization may vary between 5 and 500. Examples of the hydrophobic polymer block include poly(2-oxazoline)s with hydrophobic substituents at the 2-position of the oxazoline ring. In a particular embodiment, the hydrophobic substituent is an alkyl or an aryl. In another embodiment, the hydrophobic substituent comprises 3 to about 50 carbon atoms, 3 to about 20 carbon atoms, 3 to about 12 carbon atoms, particularly 3 to about 6 carbon atoms, or 4 to about 6 carbons. In a particular embodiment, the hydrophobic block copolymer is 2-butyl-2-oxazoline, 2-propyl-2-oxazoline, or mixtures thereof. The hydrophobic block may consist of 1-300 monomer units. In a particular embodiment, the ratio of repeating hydrophilic units to repeating hydrophobic units (in terms of the numbers of repeating units) typically ranges from about 20:1 to 1:2, preferably from about 10:1 to 1:1, and more preferably from about 7:1 to 3:1.

In a preferred embodiment of this invention, the copolymer comprises: at least one copolymer comprising repeating units of formula (I)

(I)

wherein $R^A$ is a hydrocarbon group, optionally substituted with —OH, —SH, —COOH, —$NR'_2$, —COOR', —CONR', —CHO, with R' representing H or $C_{1-3}$ alkyl, and with $R^A$ being selected such that the repeating unit of formula (I) is hydrophilic, and repeating units of the formula (II),

(II)

wherein $R^B$ is a hydrocarbon group optionally substituted with halogen, —OH, —SH, —COOH, —$NR''_2$, —COOR'', —CONR'', —CHO, with R'' representing H, alkyl or alkenyl, and with $R^B$ being selected such that the repeating unit of formula (II) is more hydrophobic than the repeating unit of formula (I).

Preferably, $R^A$ is selected from a $C_{1-8}$ hydrocarbon group, preferably a $C_{1-6}$ hydrocarbon group, more preferably a $C_{1-3}$ and in particular a $C_{1-2}$ hydrocarbon group, all of which may be optionally substituted. Preferred as hydrocarbon groups are alkyl groups.

As will be understood, the hydrophilic property of the unit of formula (I) as defined above will depend on the size of the hydrocarbon group in $R^A$. If a small hydrocarbon group is selected, such as methyl or ethyl, the resulting group $R^A$, unsubstituted or substituted with the above substituents, will always be hydrophilic. If a larger hydrocarbon group is selected, the presence of substituents may be advantageous to introduce additional polarity to the unit of formula (I). Thus, preferably, $R^A$ is selected, independently for each occurrence, from methyl and ethyl optionally substituted with halogen, —OH, —SH, —COOH, —NR'$_2$, —COOR', —CONR', —CHO, with R' representing H or $C_{1-3}$ alkyl, and particularly preferably $R^A$ is selected from methyl or ethyl.

In the units of formula (II), $R^B$ is a hydrocarbon group optionally substituted with halogen, —OH, —SH, —COOH, —NR"$_2$, —COOR", —CONR", —CHO, with R" representing H, alkyl or alkenyl, and with $R^B$ selected such that the repeating unit of formula (II) is more hydrophobic than the repeating unit of formula (I). If R" is alkyl or aryl, preferred are $C_{1-8}$ alkyl or aryl groups. Halogen substituents, if present, are preferably selected from Cl and F.

Preferably, $R^B$ is selected from a $C_{3-20}$ hydrocarbon group, preferably a $C_{3-12}$ hydrocarbon group, more preferably a $C_{3-6}$ and in particular a $C_{4-6}$ hydrocarbon group, all of which may be optionally substituted. However, it is further preferred that the hydrocarbon group does not carry a substituent.

Preferred as hydrocarbon groups are aliphatic or aromatic groups, such as alkyl groups, aryl groups or alkaryl groups. More preferred are alkyl groups, such as propyl, butyl, pentyl, hexyl, heptyl, octyl or nonyl, even more preferred are $C_{4-6}$ alkyl groups, i.e. butyl, pentyl, hexyl and specifically preferred are butyl groups, particularly n-butyl.

If necessary, i.e. if it is not readily apparent from the chemical structure of $R^A$ and $R^B$ that a specific unit of formula (II) is more hydrophobic than a given unit of formula (I), this can be verified, e.g., by preparing comparable homopolymers of the respective units and determining their log P value under the same conditions. The log P value, as commonly known, is the logarithm of the partition coefficient observed for a species A between water and n-octanol. In particular, the partition coefficient P of a species A is defined as the ratio $P=[A]_{n\text{-}octanol}/[A]_{water}$, wherein [A] indicates the concentration of A in the respective phase. The more hydrophilic substance will have higher concentrations in water. Typically, the volumes of water and octanol are the same for the measurement.

In a preferred embodiment, the correct selection of $R^B$ to provide units of formula (II) which are more hydrophobic than those of formula (I) can be verified by determining the critical micelle concentration (CMC) of a copolymer containing these units according to the procedure disclosed in detail below. If a CMC can be observed, the requirement regarding the hydrophilic nature of the units of formula (I) and the more hydrophobic/less hydrophilic nature of the units of formula (II) is reliably fulfilled.

The requirement that the units of formula (I) are hydrophilic and the units of formula (II) are more hydrophobic than those of formula (I) will also be reliably fulfilled for any possible combination of the following preferred embodiments of $R^A$ and $R^B$, as will be apparent from the structures thereof. Namely, $R^A$ is preferably selected from methyl and ethyl optionally substituted with —OH, —SH, —COOH, —NR'$_2$, —COOR', —CONR', —CHO, with R' representing H or $C_{1-3}$ alkyl, and particularly preferably $R^A$ is selected from methyl or ethyl; and $R^B$ is selected from an unsubstituted $C_{3-20}$ hydrocarbon group, preferably a $C_{3-12}$ hydrocarbon group, more preferably a $C_{3-6}$ and in particular a $C_{4-6}$ hydrocarbon group, wherein preferred hydrocarbon groups are aliphatic or aromatic groups, such as alkyl groups, aryl groups or alkaryl groups. More preferred are alkyl groups, such as propyl, butyl, pentyl, hexyl, heptyl, octyl or nonyl, even more preferred are $C_{4-6}$ alkyl groups, i.e. butyl, pentyl, hexyl and specifically preferred is a butyl, particularly n-butyl.

A copolymer comprising repeating units of formula (I) and (II) above can be conveniently prepared via ring opening polymerization of 2-substituted 2-oxazolines (or 2-substituted 4,5-dihydro oxazoles according to IUPAC nomenclature). Therefore, the polymers used in the context of the invention are also referred to as poly(2-oxazoline)s.

The copolymer according to the invention can comprise other repeating units in addition to repeating units (I) and (II) above. However, it is preferred that the major portion of all repeating units, i.e. more than 50%, more preferably more than 75%, further preferably more than 90% and particularly preferably 100%, based on the total number of repeating units, are repeating units of formula (I) or (II) as defined above. It will be understood that all repeating unit of formula (II) contained in the copolymer will be more hydrophobic than any of the repeating units of formula (I) contained in the copolymer.

The ratio of repeating units (I) to repeating units (II), in terms of the numbers of repeating units, typically ranges from 20:1 to 1:2, preferably from 10:1 to 1:1, and more preferably from 7:1 to 3:1.

With respect to the arrangement of the repeating units (I) and (II) above, the copolymers according to the invention can be random copolymers, copolymers containing segments of polymerized units of the same type (i.e. segments of units of formula (I) and/or segments of units of formula (II)), gradient copolymers or block copolymers. Block copolymers are specifically preferred.

Preferably, at least one block A of the block copolymer, more preferably all blocks A in the case of multiple occurrences, is (are) represented by formula (II):

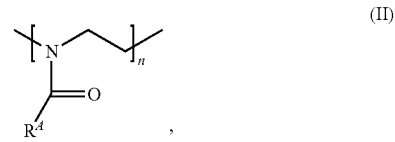

wherein $R^A$ represents a methyl or ethyl group, preferably a methyl group, and n indicates the number of repeating units within the block A. It represents preferably an integer of 5 or more, more preferably 10 or more, and particularly 20 or more. It is generally below 300, preferably 200 or less, more preferably 100 or less and in particular 50 or less.

Preferably, at least one block B of the block copolymer, more preferably all blocks B in the case of multiple occurrences, is (are) represented by formula (III):

wherein $R^B$ is a $C_{3-20}$ hydrocarbon group, preferably a $C_{3-12}$ hydrocarbon group, more preferably a $C_{3-6}$ and in particular a $C_{4-6}$ hydrocarbon group. Preferred as hydrocarbon groups are aliphatic or aromatic groups, such as alkyl groups, aryl groups or alkaryl groups. More preferred are alkyl groups such as propyl, butyl, pentyl, hexyl, heptyl, octyl or nonyl, even more $C_{4-6}$ alkyl groups, i.e. butyl, pentyl, hexyl and specifically preferred are butyl groups, particularly n-butyl. The variable n preferably represents an integer of 5 or more, more preferably of 10 or more. It is generally below 300, preferably 200 or less or 100 or less, and more preferably 50 or less.

The block copolymer used as a drug delivery system in the context of the invention contains at least one block A and at least one block B as defined above. It may contain one or more additional blocks which are different from A or B. However, it is preferred that the block copolymer contains exclusively blocks falling under the definitions and preferred definitions of A and B above. More preferably, all repeating units of the block copolymer are repeating units of formula (I) or (II) above.

As for the arrangement of blocks A and B in the copolymer used in the context of the invention, preferred structures of the copolymer can be indicated as $(AB)_m$ or $(BA)_m$ with m being 1, 2 or 3, as ABA, or as BAB. It is more preferred that the block copolymer is an AB or BA diblock copolymer or an ABA triblock copolymer.

Thus, in a particularly preferred embodiment of the invention, the polymeric entities of the block copolymer consist of (an) A block(s) consisting of polymerized 2-methyl-2-oxazoline or 2-ethyl-2-oxazoline (also referred to herein as "poly(2-methyl-2-oxazoline) block" or "poly(2-ethyl-2-oxazoline) block") and (a) B block(s) consisting of polymerized 2-($C_{4-6}$ alkyl)-2-oxazoline. Even more preferred is such copolymer with (an) A block(s) consisting of polymerized 2-methyl-2-oxazoline or 2-ethyl-2-oxazoline and (a) B block(s) consisting of polymerized 2-butyl-2-oxazoline (also referred to as "poly(2-butyl-2-oxazoline) block"). Further preferred is an AB or ABA di- or triblock-copolymer of the above constitution.

It will be understood that compositions comprising combinations, e.g. mixtures or blends of two or more different copolymers are also encompassed by the invention, e.g. combinations of copolymers containing different groups $R^A$ and or $R^B$, or combinations of copolymers showing different arrangements of their repeating units, e.g. combinations of a random polymer and a block copolymer.

In a particular embodiment of the instant invention, the copolymer of the instant invention is represented by the formula:

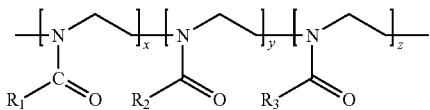

wherein x and y are independently selected between 1 and about 300, particularly about 5 to about 150, and more particularly about 10 to about 100; z is either 0 or from between 1 and about 300, particularly about 5 to about 150, and more particularly about 10 to about 100; Rx and $R_3$ are independently selected from the group consisting of —H, —OH, —$NH_2$, —SH, $CH_3$, —$CH_2CH_3$, and an alkyl comprising 1 or 2 carbon atoms; and $R_2$ is selected from the group consisting of an alkyl or an aryl. In a particular embodiment, x, y, and z are independently 5 or more, 10 or more, or 20 or more, and preferably less than 300, less than 200, less than 100, or less than 50. In a particular embodiment, R: and $R_3$ are independently selected from the group consisting of —$CH_3$ and —$CH_2CH_3$. In a particular embodiment, $R_2$ is the formula $(CH_2)_n R_4$, wherein $R_4$ is —OH, —COOH, —CHCH$_2$, —SH, —$NH_2$, —CCH, —$CH_3$, or —CHO and wherein n is about 2 to about 50, about 2 to about 20, about 2 to about 12, or about 3 to 6. In a particular embodiment, $R_2$ comprises 3 to about 50 carbon atoms, 3 to about 20 carbon atoms, 3 to about 12 carbon atoms, or 3 to about 6 carbon atoms. In yet another embodiment, $R_2$ is butyl (including isopropyl, sec-butyl, or tert-butyl) or propyl (including isopropyl). In yet another embodiment, $R_2$ is —$CH_2$—$CH_2$—$CH_2$—$CH_3$ or —$CH_2$—$CH_2$—$CH_3$.

The copolymers used in the context of the invention can be prepared by polymerization methods known in the art. For example, poly(2-oxazoline)s can be prepared by living cationic ring opening polymerization. The preparation of random copolymers, gradient copolymers and block copolymers, is described in detail, e.g., by R. Luxenhofer and R. Jordan, Macromolecules 39, 3509-3516 (2006), T. Bonne et al., Colloid. Polym. Sci., 282, 833-843 (2004) or T. Bonne et al. Macromol. Chem. Phys. 2008, 1402-1408, (2007).

Amphiphilic block copolymers can be obtained from hydrophilic 2-methyl-2-oxazoline (MeOx) and hydrophobic 2-nonyl-2-oxazoline (NonOx) (Bonne et al. (2004) Colloid Polym. Sci, 282:833; Bonne et al. (2007) Coll. Polym. Sci., 285:491). Various amphiphilic block copolymers (also additionally bearing carboxylic acid side chains for micellar catalysis (Zarka et al. (2003) Chem-Eur. J., 9:3228; Bortenschlager et al. (2005) J. Organomet. Chem., 690:6233; Rossbach et al. (2006) Angew. Chem. Int. Ed, 45:1309)) and lipopolymers have been reported and their aggregation behavior in aqueous solution was studied (Bonne et al. (2004) Colloid Polym. Sci, 282:833; Bonne et al. (2007) Coll. Polym. Sci, 285:491). CROP allows for an exact tuning of the hydrophilic-lipophilic balance (HLB) and initiation with a bi-functional initiator allows two step synthesis of triblock copolymers (FIG. 15B) in contrast to the three step synthesis necessary when, e.g., methyltriflate is used as an initiator. This approach has the additional benefit that both polymer termini can be easily functionalized with the same moiety.

The initiators used to generate the copolymers of the instant invention can be any initiator used in the art. Additionally, the termini of the copolymers of the instant invention can be any terminus known in the art. The polymers can be prepared from mono-, bi- or multifunctional initiators (such as multifunctional triflates or multifunctional oxazolines) such as, but not restricted to, methyltriflate, 1,2-bis(N-methyloxazolinium triflate) ethane or pentaerithritol tetrakistriflate. Examples of polymer termini include, for example, —OH, —$OCH_3$,

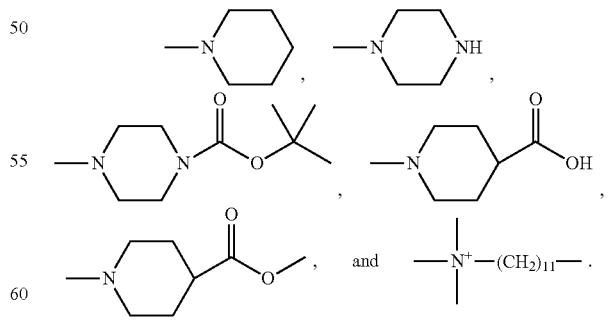

Amphiphilic copolymers of the instant invention (e.g., piperazine terminated copolymers) may be additionally labeled with a fluorescent dye (e.g., fluorescein isothiocyanate, FITC) to allow evaluation of the localization (e.g. in plasma membrane compartments such as lipid rafts, caveolae, clathrin coated pits) of these polymers by confocal microscopy (Batrakova et al. (2001) J. Pharmacol. Exp. Ther, 299:483; Bonne et al. (2004) Colloid Polym. Sci, 282:833; Bonne et al. (2007) Coll. Polym. Sci, 285:491).

The preferred size of the aggregates (also referred to herein as "complexes") is between about 5 nm and about 500 nm, between about 5 and about 200 nm, between 5 and 100 nm, between about 10 and about 150 nm, between about 10 nm and about 100 nm, or about 10 nm and about 50 nm. The aggregates (i.e., complexes) remain within the preferred size range for at least 1 hour after dispersion in the aqueous solution at the physiological pH and ionic strength, for example in phosphate buffered saline, pH 7.4. The sizes may be measured as effective diameters by dynamic light scattering (see, e.g., Batrakova et al. (2007) Bioconjugate Chem, 18:1498-1506). It is preferred that, after dispersion in aqueous solution, the aggregates (i.e., complexes) remain stable and/or do not precipitate for at least 2 hours, preferably for 12 hours, still more preferably for 24 hours (e.g., at room temperature, preferably at elevated temperatures (e.g., 37° C. or 40° C.).

In a particular embodiment, the copolymers may have a number average molecular weight (Mn) (e.g., as determined by gel permeation chromatography) ranging from about 3 to about 30, from about 4 to about 25, or from about 6 to about 20 kg/mol. In yet another embodiment, the polydispersities (PDI) is below 1.3, below 1.25, below 1.1, or can be as low as 1.001. In still another embodiment of the instant invention, the aggregates (micelles) formed by the polymers of the instant invention have a critical micelle concentration (cmc) which are less than 250 mg/L, particularly from about 5 mg/L to about 150 mg/mL or from about 5 to about 100 mg/L.

The instant invention also encompasses compositions comprising the polymer of the instant invention and at least one pharmaceutically acceptable carrier. The composition may further comprise at least one active agent, which is preferably at least one bioactive agent (e.g. therapeutic agent and/or diagnostic agent) as set forth below.

III. HYDROPHOBIC COMPOUNDS AND/OR AGENTS

The polymers of the instant invention may be used to deliver any agent(s) or compound(s), particularly active agents (or active compounds) and/or hydrophobic compounds.

The active agent (or active compound) for use in the context of the present invention is preferably a bioactive agent (or bioactive compound), including, but not limited to, agents for use in therapy (i.e. a drug) or in diagnosis, fungicides, pesticides, insecticides or herbicides, any further compounds suitable in the field of plant or crop protection such as phytohormones, or active agents for veterinary use. In one embodiment, fungicides, pesticides, insecticides, herbicides, any further compounds suitable in the field of plant or crop protection such as phytohormones, may be delivered with the polymers of the instant invention. The polymers of the instant invention may be used to deliver bioactive agents or bioactive compounds (e.g., therapeutic agent or diagnostic agent) to a subject (including non-human animals).

As used herein, the terms "active agent" and "bioactive agent" also include compounds to be screened as potential leads in the development of drugs or plant protecting agents. Indeed, the instant invention encompasses methods for the detection of active compounds which interact with a target of interest in a screening test comprising incorporating an active compound into a composition of the instant invention and subjecting the composition to the screening test.

The bioactive agent, particularly therapeutic agents, of the instant invention include, without limitation, polypeptides, peptides, glycoproteins, nucleic acids, synthetic and natural drugs, peptoides, polyenes, macrocyles, glycosides, terpenes, terpenoids, aliphatic and aromatic compounds, and their derivatives. In a preferred embodiment, the therapeutic agent is a chemical compound such as a synthetic and natural drug. In another preferred embodiment, the therapeutic agent effects amelioration and/or cure of a disease, disorder, pathology, and/or the symptoms associated therewith. The polymers of the instant invention may encapsulate one or more therapeutic agents.

Suitable drugs include, without limitation, those presented in Goodman and Oilman's The Pharmacological Basis of Therapeutics (9th Ed.) or The Merck Index (12th Ed.). Genera of drugs include, without limitation, drugs acting at synaptic and neuroeffector junctional sites, drugs acting on the central nervous system, drugs that influence inflammatory responses, drugs that affect the composition of body fluids, drugs affecting renal function and electrolyte metabolism, cardiovascular drugs, drugs affecting gastrointestinal function, drugs affecting uterine motility, chemotherapeutic agents (e.g., for hyperproliferative diseases, particularly cancer, for parasitic infections, and for microbial diseases), antineoplastic agents, immunosuppressive agents, drugs affecting the blood and blood-forming organs, hormones and hormone antagonists, dermatological agents, heavy metal antagonists, vitamins and nutrients, vaccines, oligonucleotides and gene therapies. Examples of drugs suitable for use in the present invention include, without limitation, testosterone, testosterone enanthate, testosterone cypionate, methyltestosterone, amphotericin B, nifedipine, griseofulvin, taxanes (including, without limitation, paclitaxel, docetaxel, larotaxel, ortataxel, tesetaxel and the like), doxorubicin, daunomycin, indomethacin, ibuprofen, etoposide, cyclosporin A, and vitamin E. In a particular embodiment, the drug is nifedipine, griseofulvin, a taxane, amphotericin B, etoposide or cyclosporin A.

It will be understood that compositions comprising combinations, e.g. mixtures or blends of two or more active agents, such as two drugs, are also encompassed by the invention.

Preferably, the therapeutic agent is hydrophobic. Therapeutic agents that may be solubilized or dispersed by the polymers of the present invention can be any bioactive agent and particularly those having limited solubility or dispersibility in an aqueous or hydrophilic environment, or any bioactive agent that requires enhanced solubility or dispersibility. In a particular embodiment, the polymers of the instant invention may be utilized to solubilize highly hydrophobic bioactive substances having a solubility of <1 mg/mL, <0.1 mg/mL, <50 μg/ml, or <10 μg/mL in water or aqueous media in a pH range of 0-14, preferably between pH 4 and 10, particularly at 20° C. It is preferred that active agents are comprised which have a solubility in water, e.g. ion-exchanged water, at 20° C., of less than 1 mg/mL, preferably less than 0.1 mg/mL or even less than 0.01 mg/mL, and in particular with a solubility of less than 0.001 mg/mL. Preferably, this limited solubility is shown in water over the pH range of 4 to 10.

The polymers of the instant invention may be utilized to solubilize highly hydrophobic bioactive substances of a solubility of <1 mg/mL, preferably <0.1 mg/mL or <0.01 mg/mL in water or aqueous media in a pH range of 0-14, preferably between pH 4 and 10. The preparation of the solutions of polymer and hydrophobic drug may be performed as follows: The amphiphilic block copolymer may be dissolved together with the hydrophobic compound in a common solvent, e.g. acetonitrile or dimethylsulfoxide. After removal of the solvent (e.g. by a stream of inert gas, gentle heating and/or application of reduced pressure) the films formed by the polymer and the hydrophobic compound can be easily dissolved in water or the desired aqueous solution and are tempered at elevated temperatures.

It is generally preferred that the copolymer forms aggregates in the compositions according to the invention, and it is further preferred that the aggregates are formed such that the copolymer aggregates incorporate the active agent. A particularly preferred form of such an aggregate is a micelle. A micelle, as referred to herein, is generally an aggregate of amphiphilic copolymers presenting a hydrophilic corona formed by the hydrophilic parts of the copolymer and sequestering the hydrophobic parts of said amphiphilic copolymers in the interior of the micelle. Particularly suitable copolymers for the formation of micelles are the block copolymers discussed above as a preferred embodiment of the copolymers. Micelles according to the invention are three-dimensional entities. Generally, micelles are formed when the concentration of the constituent amphiphilic molecules in an aqueous solution, exceeds a certain value. This, value is referred to as critical micelle concentration (CMC) which may be determined by using a fluorescent probe, such as pyrene, which partitions into the hydrophobic core of the micelles formed above the CMC value. More specifically, micelles according to the invention form, for example, by self-aggregation of the amphiphilic block copolymers in hydrophilic, preferably aqueous solutions. Upon formation of the micelles, the hydrophilic regions of said amphiphilic copolymers are in contact with the surrounding solvent, whereas the hydrophobic regions are facing towards the centre of the micelle. In the context of the invention, the centre of a micelle typically incorporates the hydrophobic active agent. A micelle may also be referred to as a "polymeric nanoparticle" because of its size in the nanometer range and its constituents being of polymeric nature.

The aggregates (micelles) formed by the polymers or, in particular, the copolymers, especially the block copolymers of the instant invention, preferably have CMCs which are less than 250 mg/L, particularly in the range from about 5 to about 150 or from about 5 to about 100 mg/L.

Aggregates, particularly micelles of variable size may be formed by the pharmaceutical compositions according to the invention, depending on factors such as the molecular weight of the copolymer used, or the drug load. Generally preferred are aggregates or micelles within a size range of 5-500 nm, more preferably between 5 and 100 nm. However, it is possible to advantageously form aggregates or micelles with sizes ranging from 5 to 100 or 10 to 50 nm or even from 10 to 30 nm, as determined by dynamic light scattering, which are particularly suitable for intravenous administration. Advantageously, the micelles typically have narrow particle size distributions (PDI≤0.2 or even ≤0.1).

Typically, the aggregates, particularly micelles, form in water or aqueous media. Thus, the aggregates, particularly micelles, of a composition according to the invention, may be formed, e.g., by the thin film dissolution method. In this method, the copolymer and the active agent are dissolved in a common solvent, such as acetonitrile or dimethylsulfoxide. After removal of the solvent (e.g. by a stream of inert gas, gentle heating and/or application of reduced pressure), films formed by the polymer and the active agent can be easily dissolved in water or aqueous solutions and may be tempered at increased temperatures. When the films are dissolved, the aggregates, preferably micelles, form. The stability of the aggregates allows the resulting solutions to be dried to form a powder. For example, they can freeze-dried, generally without the need for a cryoprotectant, and reconstituted in water or aqueous solutions without compromising loading capacities, particle integrity or particle sizes.

As a result of the use of the copolymers described above, the compositions according to the invention typically form aggregates soluble in water or aqueous solutions where they are stable at least 12 h at room temperature and at elevated temperatures, especially at temperatures below 40° C., that allow for the parenteral administration of said compositions in animal in general and human in particular.

In a particular embodiment, the weight ratio of the active agent (e.g., the hydrophobic therapeutic agent) to the copolymer(s), in particular the amphiphilic block copolymer(s), of the instant invention may be 1:20 or higher (e.g., 1:10). The weight ratio may be at least 1:9, at least 2:8, at least 3:7, or at least 4:6. Typically the weight ratio is less than 4:5 or 1:1.

The polymers of the instant invention increase the solubility of hydrophobic drugs by a number of orders of magnitude using as little as 1% (w/w, i.e. 10 mg/mL) of amphiphilic block copolymers in water or aqueous solutions. Extremely high loading capacities (loading capacity=(mass of hydrophobic compound)/(mass of polymer compound plus hydrophobic compound)*100%)) such as >40% (w/w), can be achieved. The high loading capacities at relatively low polymer concentration allow, in contrast to other commercialized systems, the preparation of formulations of low viscosity but high drug content. At the same time, there is a significant reduction in the amount of solubilizer subjects receive upon parenteral administration, thereby reducing the risk of adverse health effects.

In another embodiment, the polymer has a drug load of 10% or more, 25% or more, 30% or more, 35% or more, or 40% or more. It was particularly surprising that a sufficient water solubility could be eventually be achieved for compositions according to the invention having such high drug loads even with active agents with a solubility of less than 10 µg/mL or even less than 5 µg/mL, such as paclitaxel. Thus, for example, the compositions according to the invention allow for a solubilisation of paclitaxel of more than 7 mg/mL of paclitaxel, particularly 8 mg/mL or more, in water and aqueous solutions.

The high capacity even for hydrophobic active agents coincides with unusual values obtained from pyrene fluorescence spectroscopy of the pharmaceutical compositions according to the invention. The ratio of $I_1$ and $I_3$ bands in the fluorescence emission spectrum of pyrene is a measure of the polarity (K. Kalyanasundaram, J. K. Thomas, J. Am. Chem. Soc. 1977, 99, 2039-2044) of the environment of the pyrene probe. In an aqueous or similarly polar environment this ratio is typically found between 1.6 and 1.9 (K. W. Street, Jr., W. W. Acree, Jr. Analyst 1986, 111, 1197-1201). In the presence of polymer micelles, a less polar environment is available for pyrene and the $I_1/I_3$ ratio usually decreases concomitantly with an increasing overall fluorescence intensity. Quite surprisingly, with the copolymers and especially the block copolymers described herein, the opposite can be observed as the $I_1/I_3$ ratio increases to values above 2.0, preferably above 2.1 or even above 2.2, e.g. up to 2.35.

Furthermore, the instant polymers exhibit a loading efficiency (i.e. (amount of solubilized hydrophobic compound/amount of initially charged hydrophobic compound)*100%) that can reach 100% and are generally found to be very high (>80%). This is a significant finding as high loading efficiencies are of importance for commercial applications for the reduction of production costs.

Due to the high solubilising efficiency observed for the copolymers and particularly the block copolymers described above, it is generally sufficient for compositions, in particular pharmaceutical compositions in accordance with the invention in the form of aqueous solutions if the content of the copolymer ranges from concentrations as low as 1 mg/mL, preferably 2 mg/mL, to concentrations of 100 mg/mL, preferably to 50 mg/mL or 20 mg/mL. Since the copolymers are biocompatible, i.e. non-toxic, and undergo rapid renal clearance, high concentrations are not critical, but are generally not required. Compared to formulations of hydrophobic drugs currently on the market, this allows a significant reduction of the amount of solubilizer subjects receive upon parenteral administration of the drug, thus reducing the risk of adverse health effects.

As a matter of fact, the block copolymer described herein can reduce the amount of excipient needed to solubilize the same amount of paclitaxel by approx. 100 and 9 times, as compared to Cremophor EL/ethanol (CrEL) and Abraxane™, respectively.

As explained above, the copolymers according to the invention can be used to increase the solubility of active agents which are sparingly water soluble, preferably hydrophobic active agents or non-water soluble active agents, in water or aqueous solutions, i.e. they can act as a solubilizer for these compounds.

As a result, in one preferred embodiment, the compositions according to the invention further contain water to form an aqueous solution, emulsion or suspension, and particularly preferably they are aqueous solutions of the active agent and the copolymer. It will be understood that the term "solution" comprises, in this specific context, colloidal solutions as they may be formed by micelles in water. However, since the copolymers used in the context of the invention allow the compositions to be lyophilized without compromising the activity and the stability of the active agent and without the need for a cryoprotectant, powders, especially lyophilized powders, form another preferred embodiment of the compositions according to the invention. These powders may be conveniently reconstituted in water or aqueous solutions.

Thus, the polymers described herein can serve, e.g., as a versatile high capacity drug delivery system even for hydrophobic and structurally diverse drugs such as paclitaxel, cyclosporin A and amphotericin B.

Other preferred embodiments of the present invention are summarized in the following items:

1. Pharmaceutical composition comprising:
   (a) at least one biocompatible water soluble amphiphilic block copolymer comprising of at least one block A and at least one block B, wherein A is a hydrophilic polymer selected from hydrophilic poly(2-oxazoline)s and B is selected from amphiphilic or hydrophobic poly(2-oxazoline)s and
   (b) a hydrophobic bioactive compound,
   that form soluble aggregates in water or aqueous solutions that are stable at least 12 h at room temperature and at elevated temperatures, especially at temperatures below 40° C., that allow for the parenteral administration of said compositions in animal in general and human in particular.
2. Pharmaceutical compositions of item 1, wherein B is represented by the following structure of formula (III):

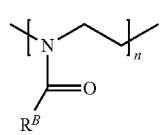

(III)

wherein $R^B$ is a hydrophobic side chain (comprising a saturated aliphatic chain, an unsaturated aliphatic chain, a saturated aliphatic ring or an unsaturated aliphatic ring or mixtures thereof) and n is selected between 1 and 300.

3. Pharmaceutical composition according to item 1 or 2, wherein hydrophobic bioactive compound comprises peptides, peptoides, polyenes, macrocyles, glycosides, terpenes, terpenoids, aliphatic and aromatic compounds and their derivatives and other compounds of a solubility in water or aqueous media at a pH range of 4-10 lower than 1 mg/mL, preferably lower 100 µg/mL, even more preferably lower than 50 µg/mL. and most preferably lower than 10 µg/mL.
4. Pharmaceutical compositions according to any of items 1 to 3, wherein the hydrophobic bioactive compound is selected from amphotericin B, nifedipine, griseofolvin, paclitaxel, docorubicin, daunomycin, indomethacain, ibuprofen, etoposide and cyclosporine A.
5. Pharmaceutical compositions according to any of items 1 to 3, wherein the hydrophobic bioactive compound is paclitaxel.
6. Pharmaceutical compositions according to any of items 1 to 5, wherein the AB block copolymers are attached through stable or labile linkages to form compounds that can be depicted as $(AB)_m$, with m ranging from 2-100, forming, for example, linear or star-like block copolymers, graft block copolymers, dendrimer based or hyperbranched blockcopolymers.
7. Pharmaceutical compositions according to any of items 2 to 6, wherein the hydrophobic side chain R comprises 3-6 carbon atoms.
8. Pharmaceutical compositions according to any of items 1 to 7, wherein the amphiphilic block copolymer comprises a block that consists in part or completely of repeating units derived from 2-butyl-2-oxazoline.
9. Pharmaceutical compositions according to any of items 1 to 8, wherein the hydrophilic polyoxazoline is selected from poly(2-methyl-2-oxazoline) or poly(2-ethyl-2-oxazoline).
10. Pharmaceutical compositions according to any of items 1 to 9, wherein the soluble aggregates in aqueous media are in the size range of 5-200 nm, preferably 10-100 nm.
11. Pharmaceutical compositions according to any of items 1 to 10, comprising the hydrophobic bioactive compound and amphiphilic block copolymer in a weight ratio of at least 1:9, preferable 2:8, more preferable 3:7 and most preferable 4:6.

IV. ADMINISTRATION

Due to the inherent versatility of the pharmaceutical compositions forming a preferred embodiment according to the invention as regards bioactive agents/compounds to be incorporated, it will be understood that the compositions are suitable for the treatment or prevention of a wide variety of diseases or disorders such as cancer, neurodegenerative diseases, hepato-biliary diseases, cardiovascular diseases or pulmonary diseases. The invention also encompasses the use of the block copolymers as defined above for the preparation of a pharmaceutical composition for the treatment or prevention of any of these diseases. Moreover, diagnostic applications of the compositions according to the inventions are also envisaged.

The polymer-therapeutic agent complexes described herein will generally be administered to a patient as a pharmaceutical preparation. These polymer-therapeutic agent complexes may be employed therapeutically, under the guidance of a physician. While the therapeutic agents are exemplified herein, any bioactive agent may be administered to a patient, e.g., a diagnostic agent.

The compositions comprising the polymer-therapeutic agent complex of the instant invention may be conveniently formulated for administration with any pharmaceutically acceptable carrier(s). For example, the complexes may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the polymer-therapeutic agent complexes in the chosen medium may be varied and the medium may be chosen based on the desired route of administration of the pharmaceutical preparation. Except insofar as any conventional media or agent is incompatible with the polymer-therapeutic agent complexes to be administered, its use in the pharmaceutical preparation is contemplated.

The pharmaceutical compositions according to the invention may optionally be formulated together with one or more further pharmaceutically acceptable excipients, such as carriers, diluents, fillers, disintegrants, lubricating agents, binders, colorants, pigments, stabilizers, preservatives, and/or antioxidants.

The pharmaceutical compositions can be formulated by techniques known to the person skilled in the art, such as the techniques published in Remington's Pharmaceutical Sciences, 20th Edition. The pharmaceutical compositions can be formulated as dosage forms for oral, parenteral, such as intramuscular, intravenous, subcutaneous, intradermal, intraarterial, rectal, topical, pulmonary or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for pulmonary administration/pulmonary delivery can be administered via inhalation and insufflation, for example by a metered dose inhaler. Dosage forms for topical administration include creams, gels, ointments, salves, patches and transdermal delivery systems.

The dose and dosage regimen of polymer-therapeutic agent complexes according to the invention that are suitable for administration to a particular patient may be determined by a physician considering the patient's age, sex, weight, general medical condition, and the specific condition for which the polymer-therapeutic agent complex is being administered and the severity thereof. The physician may also take into account the route of administration, the pharmaceutical carrier, and the polymer-therapeutic agent complex's biological activity.

Selection of a suitable pharmaceutical preparation will also depend upon the mode of administration chosen. For example, the polymer-therapeutic agent complex of the invention may be administered by direct injection to a desired site. In this instance, a pharmaceutical preparation comprises the polymer-therapeutic agent complex dispersed in a medium that is compatible with the site of injection.

Polymer-therapeutic agent complexes of the instant invention may be administered by any method. For example, the polymer-therapeutic agent complex of the instant invention can be administered, without limitation parenterally, subcutaneously, orally, topically, pulmonarily, rectally, vaginally, intravenously, intraperitoneally, intrathecally, intracerebrally, epidurally, intramuscularly, intradermally, or intracarotidly. In a particular embodiment, the complexes are administered intravenously or intraperitoneally. Pharmaceutical preparations for injection are known in the art. If injection is selected as a method for administering the polymer-therapeutic agent complex, steps must be taken to ensure that sufficient amounts of the molecules or cells reach their target cells to exert a biological effect. Dosage forms for oral administration include, without limitation, tablets (e.g., coated and uncoated, chewable), gelatin capsules (e.g., soft or hard), lozenges, troches, solutions, emulsions, suspensions, syrups, elixirs, powders/granules (e.g., reconstitutable or dispersible) gums, and effervescent tablets. Dosage forms for parenteral administration include, without limitation, solutions, emulsions, suspensions, dispersions and powders/granules for reconstitution. Dosage forms for topical administration include, without limitation, creams, gels, ointments, salves, patches and transdermal delivery systems.

For example, the pharmaceutical compositions according to the invention may be administered to a subject by any convenient route of administration, whether systemically/peripherally or at the site of desired action, including but not limited to one or more of: oral (e.g. as a tablet, capsule, or as an ingestible solution), topical (e.g., transdermal, intranasal, ocular, buccal, and sublingual), parenteral (e.g., using injection techniques or infusion techniques, and including, for example, by injection, e.g. subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g. through mouth or nose), gastrointestinal, intrauterine, intraocular, subcutaneous, ophthalmic (including intravitreal or intracameral), rectal, and vaginal. Oral and parenteral, especially intravenous administration is generally preferred since the compositions according to the invention provide a sufficient solubility and bioavailability for these routes even when hydrophobic active agents are used.

If the pharmaceutical compositions are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

The pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Alternatively, the pharmaceutical compositions can be administered in the form of a suppository or pessary, or it may be applied topically in the form of a gel, hydrogel, lotion, solution, cream, ointment or dusting powder. The compositions of the present invention may also be dermally or transdermally administered, for example, by the use of a skin patch.

The pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For topical application to the skin, pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

In view of the advantageous solubilising effects provided by the compositions according to the invention, it will be understood that they are preferably administered in forms and/or according to modes of administration which require solubility of the bioactive ingredient in water.

Pharmaceutical compositions containing a polymer-therapeutic agent complex of the present invention as the active ingredient in intimate admixture with a pharmaceutically acceptable carrier can be prepared according to conventional pharmaceutical compounding techniques. The carrier may take a wide variety of forms depending on the form of preparation desired for administration, e.g., intravenous, oral, direct injection, intracranial, and intravitreal.

Typically, a physician will determine the actual dosage of the pharmaceutical compositions which will be most suitable for an individual subject. The specific dose level and frequency of dosage for any particular individual subject may be varied and will depend upon a variety of factors including the disorder or disease to be treated or prevented, the specific bioactive compound employed, the metabolic stability and length of action of that compound, the age, body weight, general health, sex, diet, mode and time of administration, rate of excretion, drug combination, the severity of the particular condition, and the individual subject undergoing therapy.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of polymer-therapeutic agent complexes may be determined by evaluating the toxicity of the molecules or cells in animal models. Various concentrations of polymer-therapeutic agent complexes in pharmaceutical preparations may be administered to mice, and the minimal and maximal dosages may be determined based on the beneficial results and side effects observed as a result of the treatment. Appropriate dosage unit may also be determined by assessing the efficacy of the polymer-therapeutic agent complex treatment in combination with other standard drugs. The dosage units of polymer-therapeutic agent complex may be determined individually or in combination with each treatment according to the effect detected.

The pharmaceutical preparation comprising the polymer-therapeutic agent complexes may be administered at appropriate intervals, for example, at least twice a day or more until the pathological symptoms are reduced or alleviated, after which the dosage may be reduced to a maintenance level. The appropriate interval in a particular case would normally depend on the condition of the patient.

A proposed, yet non-limiting dose of the compositions according to the invention for administration to a human (of approximately 70 kg body weight) may be 0.1 μg to 10 g, preferably 0.1 mg to 0.5 g, based on the weight of the active agent (i.e. the drug) per unit dose. The unit dose may be administered, for example, 1 to 4 times per day. The dose will depend on the route of administration. It will be appreciated that it may be necessary to make routine variations to the dosage depending on the age and weight of the patient/subject as well as the severity of the condition to be treated. The precise dose and route of administration will ultimately be at the discretion of the attendant physician or veterinarian.

In a particular embodiment, the polymer-therapeutic agent is administered to a cell of the body in an isotonic solution at physiological pH 7.4. However, the complexes can be prepared before administration at a pH below or above pH 7.4.

The instant invention encompasses methods of treating or diagnosing a disease/disorder comprising administering to a subject in need thereof a composition comprising a polymer-bioactive agent complex of the instant invention and, preferably, at least one pharmaceutically acceptable carrier. In a particular embodiment, the disease is cancer and the polymer comprises at least one chemotherapeutic agent (particularly a taxane (e.g., paclitaxel). Other methods of treating the disease or disorder may be combined with the methods of the instant invention (e.g., other chemotherapeutic agents or therapy (e.g., radiation) may be co-administered with the compositions of the instant invention.

The subject or patient, such as the subject in need of treatment or prevention, to which the compositions according to the invention are administered, is generally a mammal. In the context of this invention, it is particularly envisaged that mammals are to be treated, besides humans, which are economically or agronomically important. Non-limiting examples of agronomically important animals are sheep, cattle and pig, while, for example, cats and dogs may be considered as economically important animals. Preferably, the subject/patient is a human.

The term "treatment of a disorder or disease" as used herein is well known in the art. "Treatment of a disorder or disease" implies that a disorder or disease has been diagnosed in a patient/subject. A patient/subject suspected of suffering from a disorder or disease typically shows specific clinical and/or pathological symptoms which a skilled person can easily attribute to a specific pathological condition (i.e. diagnose a disorder or disease).

"Treatment of a disorder or disease" may, for example, lead to a halt in the progression of the disorder or disease (e.g. no deterioration of symptoms) or a delay in the progression of the disorder or disease (in case the halt in progression is of a transient nature only). "Treatment of a disorder or disease" may also lead to a partial response (e.g. amelioration of symptoms) or complete response (e.g. disappearance of symptoms) of the subject/patient suffering from the disorder or disease. "Amelioration" of a disorder or disease may, for example, lead to a halt in the progression of the disorder or disease or a delay in the progression of the disorder or disease. Such a partial or complete response may be followed by a relapse. It is to be understood that a subject/patient may experience a broad range of responses to a treatment (e.g. the exemplary responses as described herein above). Treatment of a disorder or disease may, inter alia, comprise curative treatment (preferably leading to a complete response and eventually to healing of the disorder or disease) and palliative treatment (including symptomatic relief).

Also the term "prevention of a disorder or disease" as used herein is well known in the art. For example, a patient/subject suspected of being prone to suffer from a disorder or disease as defined herein may, in particular, benefit from a prevention of the disorder or disease. Said subject/patient may have a susceptibility or predisposition for a disorder or disease, including but not limited to hereditary predisposition. Such a predisposition can be determined by standard assays, using, for example, genetic markers or phenotypic indicators. It is to be understood that a disorder or disease to be prevented in accordance with the present invention has not been diagnosed or cannot be diagnosed in said patient/subject (for example, said patient/subject does not show any clinical or pathological symptoms). Thus, the term "prevention" comprises the use of compounds of the present invention before any clinical and/or pathological symptoms are diagnosed or determined or can be diagnosed or determined by the attending physician.

The following examples provide illustrative methods of practicing the instant invention, and are not intended to limit the scope of the invention in any way.

1. General Materials and Methods

All substances for the preparation of the polymers were purchased from Aldrich (Steinheim, Germany) and Acros (Geel, Belgium) and were used as received unless otherwise stated. 2-Butyl-2-oxazoline (BuOx) was prepare as recently described (Huber, S, and Jordan, R., Colloid Polym. Sci. 286, 395-402 (2008)). Methyl trifluoromethylsulfonate (methyl triflate, abbreviated herein as "MeOTf"), 2-methyl-2-oxazoline (abbreviated herein as "MeOx"), 2-ethyl-2-oxazoline (abbreviated herein as "EtOx"), acetonitrile (abbreviated herein as "ACN") and other solvents for polymer preparation were dried by refluxing over $CaH_2$ under dry nitrogen atmosphere and subsequent distillation prior to use. NMR spectra were recorded on a Bruker Avance III 400, Bruker ARX 300 or a Bruker AC 250 at room temperature. The spectra were calibrated using the solvent signals ($CDCl_3$ 7.26 ppm, $D_2O$ 4.67 ppm). Gel permeation chromatography (GPC) was performed on a Waters system (pump mod. 510, RI-detector mod. 410, pre-column PLgel™ (PLgel™ is a highly cross-linked spherical polystyrene/divinylbenzene matrix for non-interactive GPC/SEC polymers) and two PL ResiPore™ columns (300×7.5 mm columns containing 3 μm highly cross-linked polystyrene/divinylbenzene (PS/DVB) beads) (PLgel™ and PL ResiPore™ liquid chromatography columns are available from Polymer Laboratories, a Varian, Inc., subsidiary) with N,N-dimethyl acetamide (abbreviated herein as "DMAc") (75 mmol/L LiBr, 80° C., 1 mL/min) as eluent and calibrated against poly(methylmethacrylate) (abbreviated herein as "PMMA") standards. Dynamic light scattering was performed using a Zetasizer Nano-ZS (Malvern Instruments Inc., Southborough, Mass.) at room temperature.

The polymerizations and work-up procedures were carried out according to the procedure described previously (Luxenhofer, R. and Jordan, R., Macromolecules 39, 3509-3516 (2006); Bonné, T. B., et al., Colloid Polym. Sci. 282, 833-843 (2004))

EXAMPLE 1

Preparation of Methyl-P [$MeOx_{26}$-b-$BuOx_{20}$-b-$MeOx_{28}$]-piperidine (LXRB20)

Methyltriflate (24.7 mg, 0.150 mmol, 1 eq) and 334 mg 2-methyl-2-oxazoline (3.9 mmol, 26 eq) were dissolved in 3.14 mL (2.45 g) acetonitrile. The mixture was heated to 130° C. for 20 minutes using a microwave. After cooling to room temperature, 136 mg (5% w/w) of the reaction mixture was removed for analysis of the first block with nuclear magnetic resonance (NMR) and gel permeation chromatography (GPC). After addition of 364.4 mg 2-butyl-2-oxazoline (2.87 mmol, 20 eq), the mixture was again heated to 130° C. for 20 minutes. Once more, after removal of an aliquot (306.9 mg, 10% w/w) was removed, 306.9 mg MeOx (3.6 mmol, 28 eq) was added and the mixture was heated to 130° C. for 20 minutes. After cooling to room temperature (RT), 80 μL of piperidine was added and the mixture was stirred overnight. After exchange of the solvent with chloroform, a spatula's tip of $K_2CO_3$ was added and the mixture was left stirring for 4 hours at room temperature. After filtration, the product methyl-P[$MeOx_{26}$-b-$BuOx_{20}$-b-$MeOx_{28}$]-piperidine (598 mg, 0.083 mmol, 65% yield) was obtained as a colorless solid after precipitating the chloroform solution twice from cold diethylether.

EXAMPLE 2

Preparation of Methyl-P [$MeOx_{27}$-b-$BuOx_{15}$-b-$MeOx_{27}$]-piperidine (LXRB15)

Using 24 mg MeOTf (0.146 mmol, 1 eq) as an initiator, MeOx (332.8 mg first block (3.91 mmol, 27 eq), 333.2 third block (3.91 mmol, 27 eq)) and 286.3 mg BuOx (2.25 mmol, 15 eq) and 80 μL of piperidine as terminating reagent, methyl-P[$MeOx_{27}$-b-$BuOx_{15}$-b-$MeOx_{27}$]-piperidine was prepared according to the general procedure described in Example 1.

EXAMPLE 3

Paclitaxel 2 mg/mL

The enhanced solubilization of 2-butyl-2-oxazoline derived polymers is illustrated in this example. The polymers (400 μg) and paclitaxel (20, 100 and 200 μgram, dissolved in acetonitrile, stock solution 5 mg/mL) were dissolved in 200

μL acetonitrile. The solvent was removed in a stream of air (or nitrogen or any other non-reactive gas) and the film was subjected to 0.2 mbar for at least 3 hours to remove residual solvent. Subsequently, 200 μL of buffer (aqueous solution, containing 122 mM NaCl, 25 mM $Na_2CO_3$, 10 mM HEPES, 10 mM glucose, 3 mM KCl, 1.4 mM $CaCl_2$ and 0.4 mM $K_2HPO_4$, pH=7.4) were added to obtain a final polymer concentration of 0.2 mg/mL (=2% (w/w)). The solution was filtered through syringe filters (0.45 micron pore size) and subjected to high performance liquid chromatography (HPLC) analysis. HPLC analysis was carried out under isocratic conditions using a Shimadzu system comprising a SCL-10A system controller, SIL-10A autoinjector, SPD-10AV UV detector and two LC-10 AT pumps. A Nucleosil® C18-5μ column (250 mm×4 mm) was used as the stationary phase and an acetonitrile/water mixture (55/45, v/v) was used as the mobile phase. Detection was performed at 220 nm. The amount of paclitaxel in the polymer solution was calculated using a calibration curve obtained using known amounts of paclitaxel dissolved in acetonitrile and analyzed accordingly. The results are shown in FIG. 1.

Figure 1A:
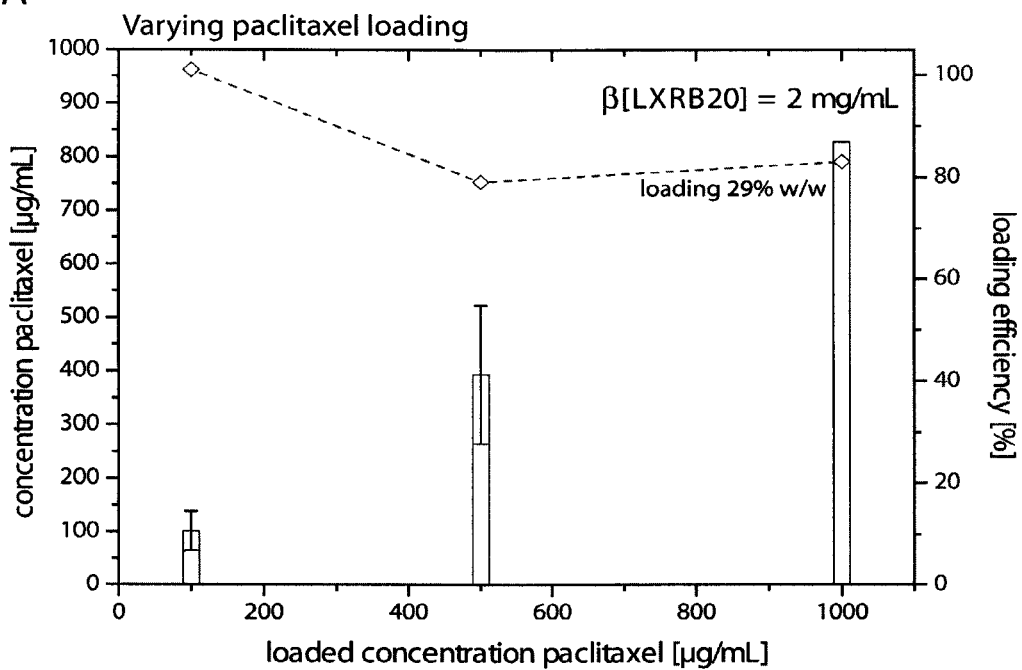
Figure 1B:
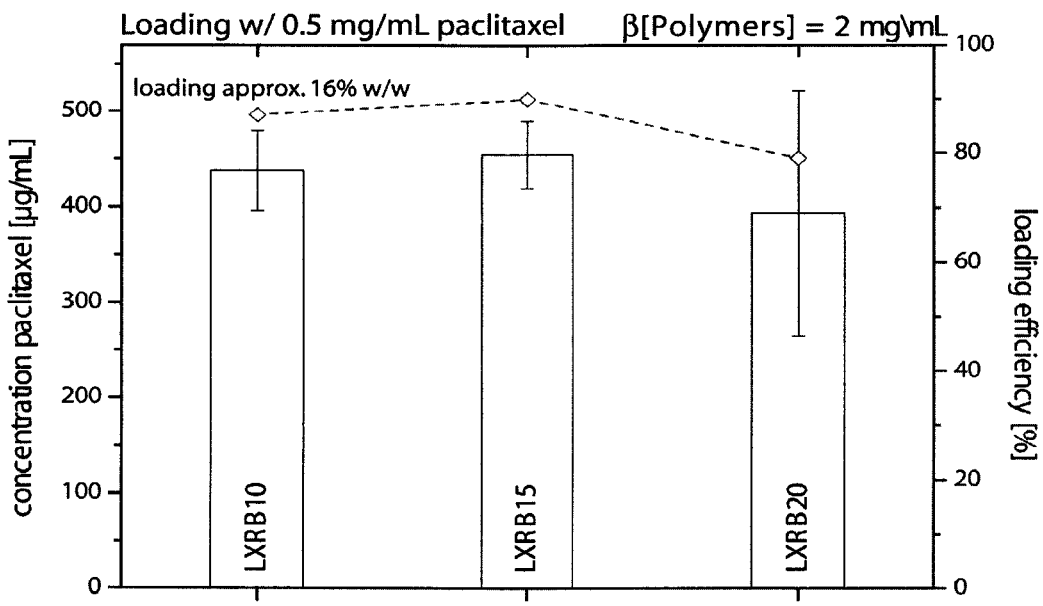

As seen in FIG. 1, the compositions were capable of solubilizing increasing amounts of paclitaxel. Even at a low polymer concentrations of 2 mg/mL, more than 0.8 mg/mL paclitaxel could be solubilized in aqueous solutions with these compositions, giving a loading capacity of approximately 30% (w/w). Surprisingly, the length of the hydrophobic block appears to have a limited effect (FIG. 1B). Decreasing the length of the hydrophobic block from 20 to 10 monomer units does not significantly diminish the drug loading capacity of the respective compositions.

EXAMPLE 4

Paclitaxel 10 mg/mL Polymer

Following the procedure of Example 3, aqueous solutions of pharmaceutical composition comprising LXRB 15 (10 mg/mL, 1% w/v) and various amounts of paclitaxel were prepared and analyzed subsequently. The results are presented in FIG. 2.

Figure 2:
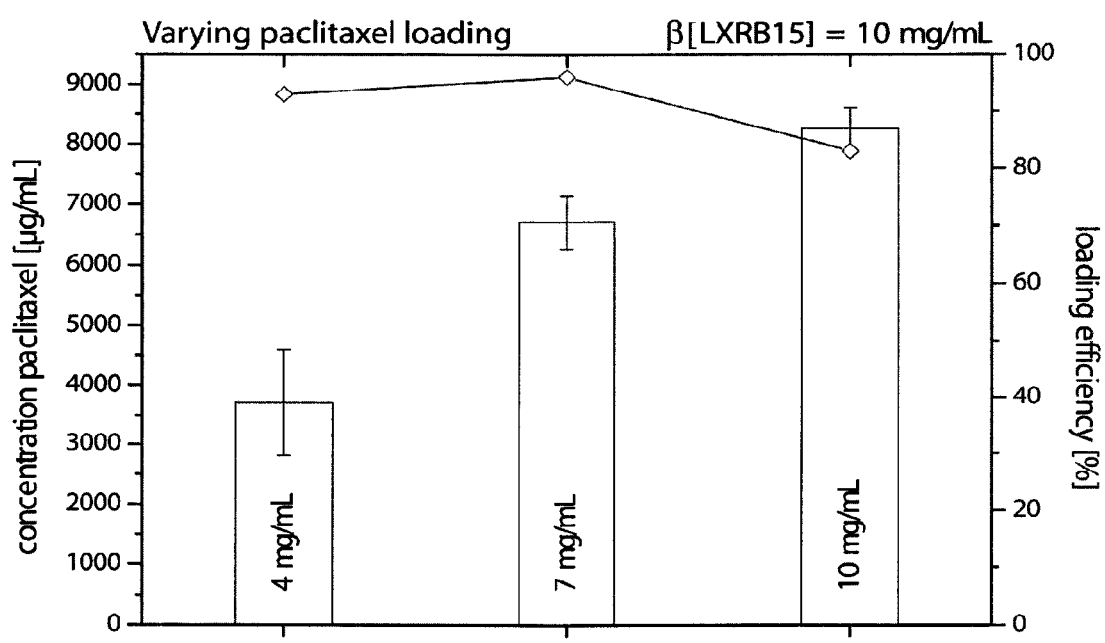
FIG. 2 is a graph depicting the amount of paclitaxel loaded with increasing amounts of LXRB15 and the loading efficiency.

FIG. 2 shows the amount of paclitaxel solubilized in aqueous solutions within paclitaxel-LXRB15 compositions. Depending on the attempted drug loading, up to 8.3 mg/mL paclitaxel was found in aqueous solutions of compositions comprising 10 mg/mL LXRB15. This corresponds to a final drug loading of 45% (w/w) and a loading efficiency of 83%.

The size of the aggregates was determined using dynamic light scattering. For example, the Z-average size of the aggregates formed by the composition comprising 10 mg/mL LXRB15 and 3.7 mg/mL paclitaxel was found to be 20.7 nm with a very narrow size distribution (PDI=0.043). Similar values, ranging from 20-30 nm in diameter have been found for other compositions with also typically very narrow size distributions.

EXAMPLE 5

Paclitaxel Freeze Drying

Polymer amphiphile solutions with solubilized paclitaxel were frozen to −80° C. and subsequently freeze dried. After taking the dry, colorless powders up with water to give clear solutions without any visible solid particles, they were subjected to centrifugation at 16,000×g for 15 minutes to sediment eventually present solids. Finally the solutions where subjected to HPLC analysis as described in Example 3. The results are presented in Table 1.

TABLE 1

| Composition | Conc. Polymer | Conc. Paclitaxel | Paclitaxel Loading | Loading Efficiency |
|---|---|---|---|---|
| LXRB 15 + paclitaxel | 10 mg/mL | 7.46 mg/mL | 43% | 75% |
| LXRB 15 + paclitaxel | 10 mg/mL | 6.62 mg/mL | 40% | 88% |

This example shows clearly that the compositions of the present invention can be freeze dried, allowing prolonged storage as dry powders and easy reconstitution (e.g., by untrained personnel in a hospital setting), while retaining extraordinarily high drug loading.

EXAMPLE 6

Cyclosporin A

To demonstrate the feasibility of cyclosporin A (CsA) containing compositions, 1 mg of LXRB15 was dissolved in 100 μL of acetonitrile. 50 μL of a 5 mg/mL cyclosporin A solution in ACN was added. Processing of the formulations was performed according to the procedure outlined above, using 200 μL of aqueous buffer. Isocratic HPLC analysis was performed at 70° C. using a mobile phase of 90% aqueous acetonitrile. The aqueous solution of the compositions was found to comprise 1.03 mg/mL CsA. Thus, drug loading was 17% (w/w) and loading efficiency was 82%. Under the same conditions, 8 μg/mL CsA was found to be solubilized in the aqueous buffer without amphiphilic block copolymer. Thus, compositions of the present invention can increase the solubility of cyclosporin A in a 0.5% (w/w) aqueous solution of the amphiphilic block copolymer LXRB15 at least 130 times.

The drug content of the composition was again analyzed after 3 days. While no change for the block copolymer cyclosporin A composition was found, the aqueous solution of cyclosporin A contained no detectable CsA. This shows that the compositions are of considerable stability and can be stored in aqueous solution for at least 3 days.

EXAMPLE 7

Further Studies of Polymers

Table 2 provides the polymers used for the solubilization of paclitaxel, in accordance with the methods described hereinabove.

TABLE 2

| Sample Name | Polymer Composition* | Molar mass* [kg/mol] |
|---|---|---|
| LXRB10 | M[MeOx$_{26}$-b-BuOx$_{10}$-b-MeOx$_{26}$]Pid | 5.8 |
| LXRB15 | M[MeOx$_{26}$-b-BuOx$_{15}$-b-MeOx$_{26}$]Pid | 6.4 |
| LXRB20 | M[MeOx$_{26}$-b-BuOx$_{20}$-b-MeOx$_{26}$]Pid | 7.0 |
| LXR426 | B[BuOx$_{25}$-b-MeOx$_{53}$]BPip | 8.3 |
| LXR429 | T[BuOx$_{20}$-b-MeOx$_{100}$]BPip | 9.7 |
| LXR430T4 | B[MeOx$_{26}$-b-BuOx$_{15}$-b-MeOx$_{26}$]Pid | 6.8 |

TABLE 2-continued

| Sample Name | Polymer Composition* | Molar mass* [kg/mol] |
|---|---|---|
| LXR434 | T[NonOx$_8$-b-MeOx$_{52}$]Pid | 5.0 |
| LXR438 | B[BuOx$_{15}$-b-MeOx$_{52}$]Pip | 6.8 |

Figure 3A:
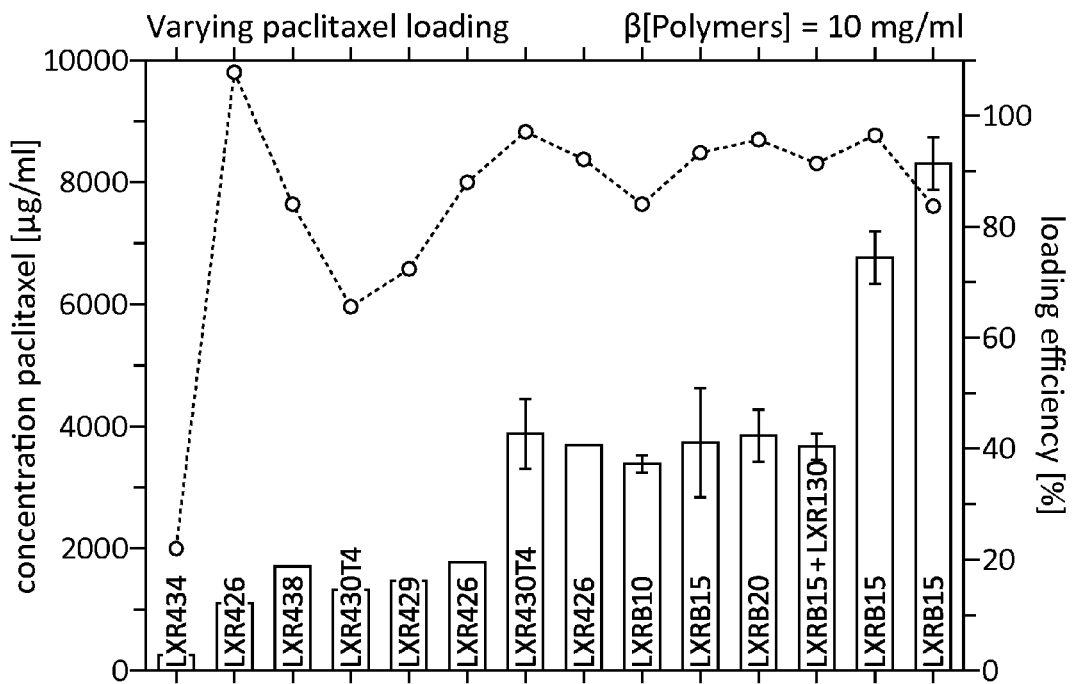
FIGS. 3A-3C are graphs depicting the amount of paclitaxel loaded and the loading efficiency with various polymers.
Figure 3B:
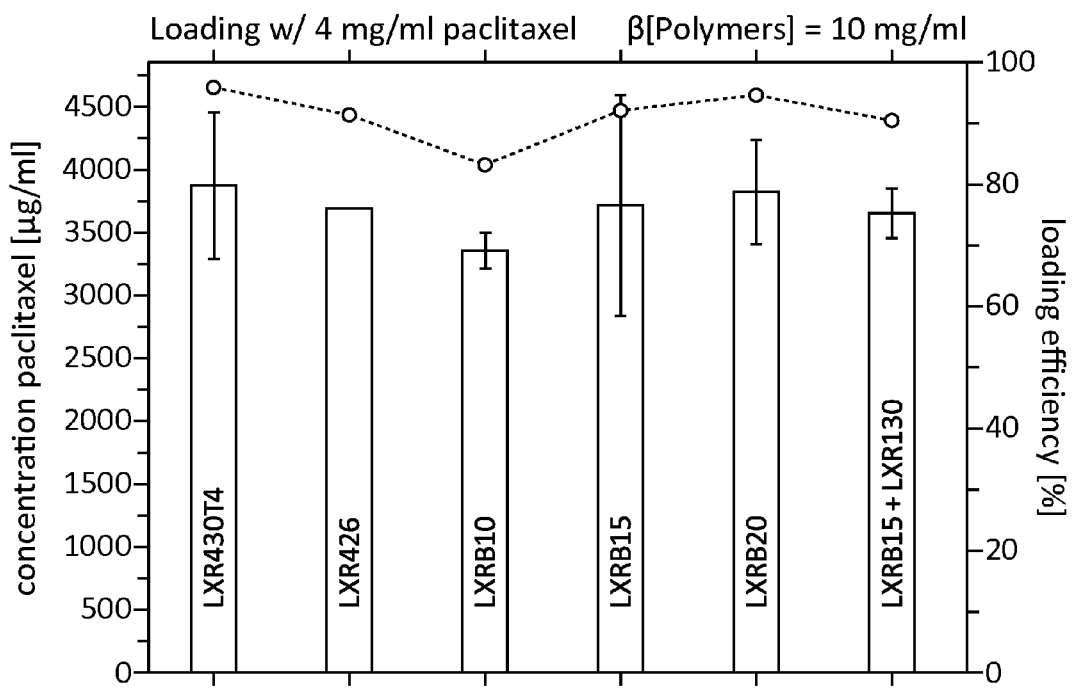
Figure 3C:
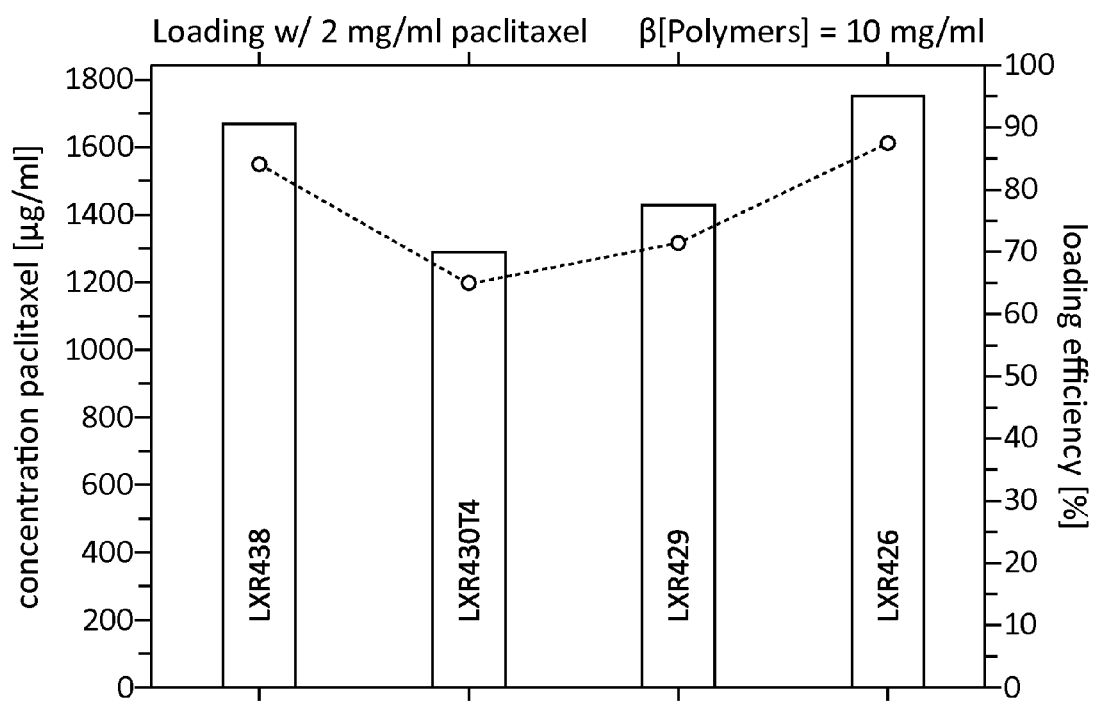

*as determined by [M]$_0$/[I]$_0$;
M = methyltriflate initiated polymer;
B = 1,2-(N-methylbisoxazolinyliumtri£late) ethane initiated polymer;
T = tetrakistriflate pentaerithritol initiated polymer;
MeOx = 2-methyl-2-oxazoline;
BuOx = 2-butyl-2-oxazoline;
NonOx = 2-nonyl-2-oxazoline;
Pid = piperidine terminated polymer;
Pip = piperazine terminated polymer;
Bpip = N-Boc-piperazine terminated polymer FIG. 3 demonstrates the solubilization of paclitaxel in micelles of various amphiphilic poly(2-oxazoline)s. The columns show the paclitaxel concentration in aqueous micelle solution as determined by HPLC. The line graph represents the loading efficiency ([paclitaxel]$_{det}$/[paclitaxel]$_0$×100%). The polymer concentration in FIGS. 3A-3C is 10 mg/ml. FIG. 3 A provides an overview of the solubilization power of various polymers at various paclitaxel loading concentrations. The first entry, which shows a very low loading efficiency, is a polymer which contains 2-nonyl-2-oxazoline instead of 2-butyl-2-oxazoline as the hydrophobic monomer. FIGS. 3B and 3C show the solubilization of paclitaxel and loading efficiencies for various different polymers at loading concentrations of 4 and 2 mg/mL, respectively.

EXAMPLE 8

Comparison to Cremophor EL®

To demonstrate the benefit of the present invention, the solubilization of compositions of the present invention was compared with the most commonly used, commercially available dispersant for paclitaxel, namely, a 50/50 (v/v) mixture of Cremophor EL® and dehydrated ethanol. In order to obtain a paclitaxel content of 4 mg/mL (a concentration needed to allow single bolus i.v. injection (100 μL) of a 20 mg/kg dose in mice), an aqueous solution containing 66% (v/v) of the commercially available paclitaxel/Cremophor EL® formulations would have to be prepared, containing 613 mg excipient per mL of solution. Using compositions of the present invention, a 4 mg/mL paclitaxel content can be achieved using as little as 5 mg/mL amphiphilic block copolymer or less, thereby decreasing the amount of excipient needed approximately 120 times.

Figure 4A:
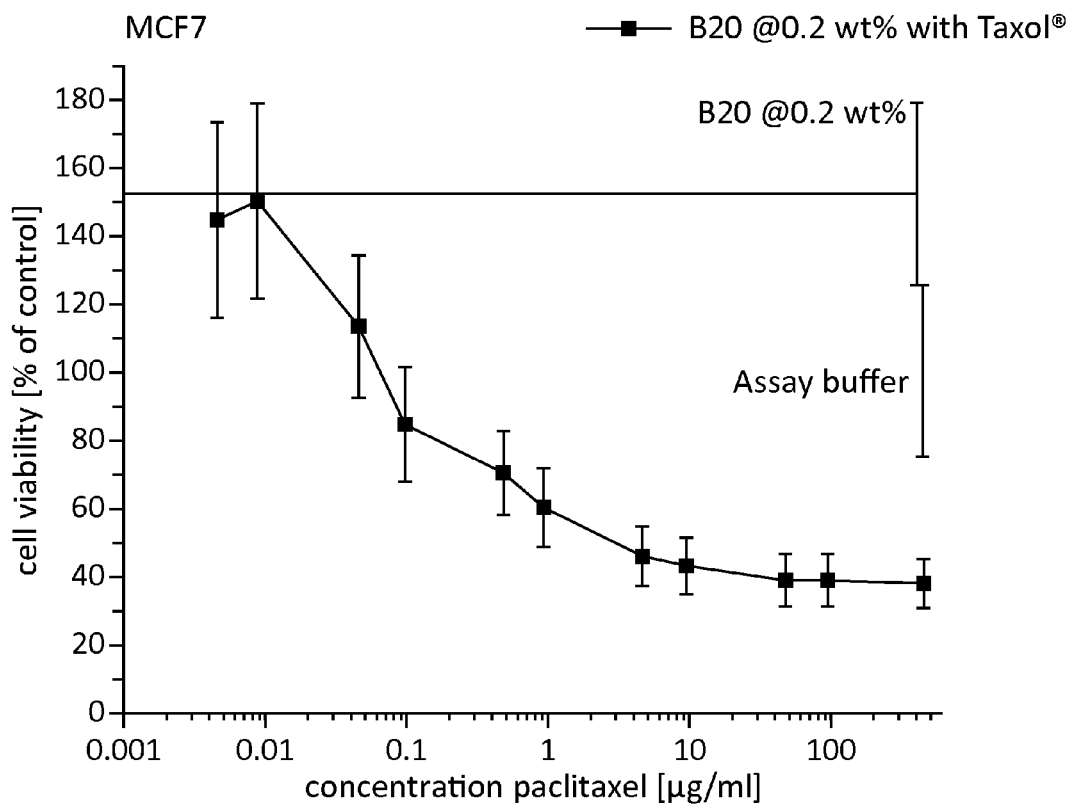
FIGS. 4A and 4B are graphs depicting the toxicity of paclitaxel (Taxol®) solubilized in LXRB20 of paclitaxel solubilized in Cremophor EL®.
Figure 4B:
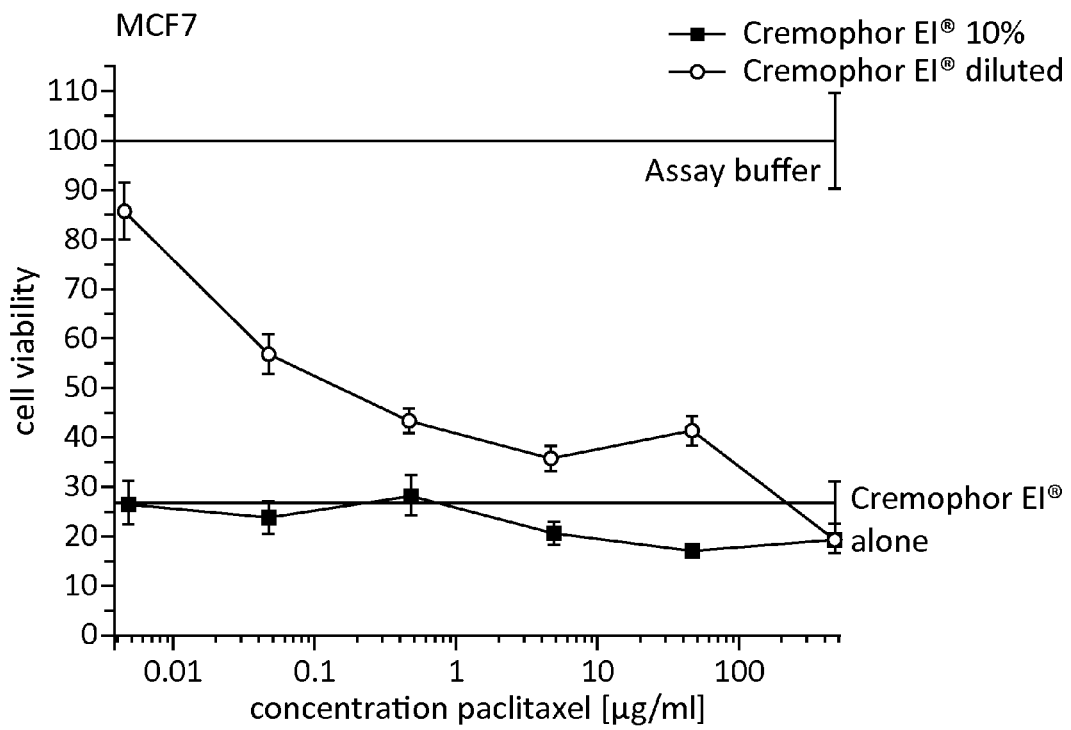
Figure 4C:
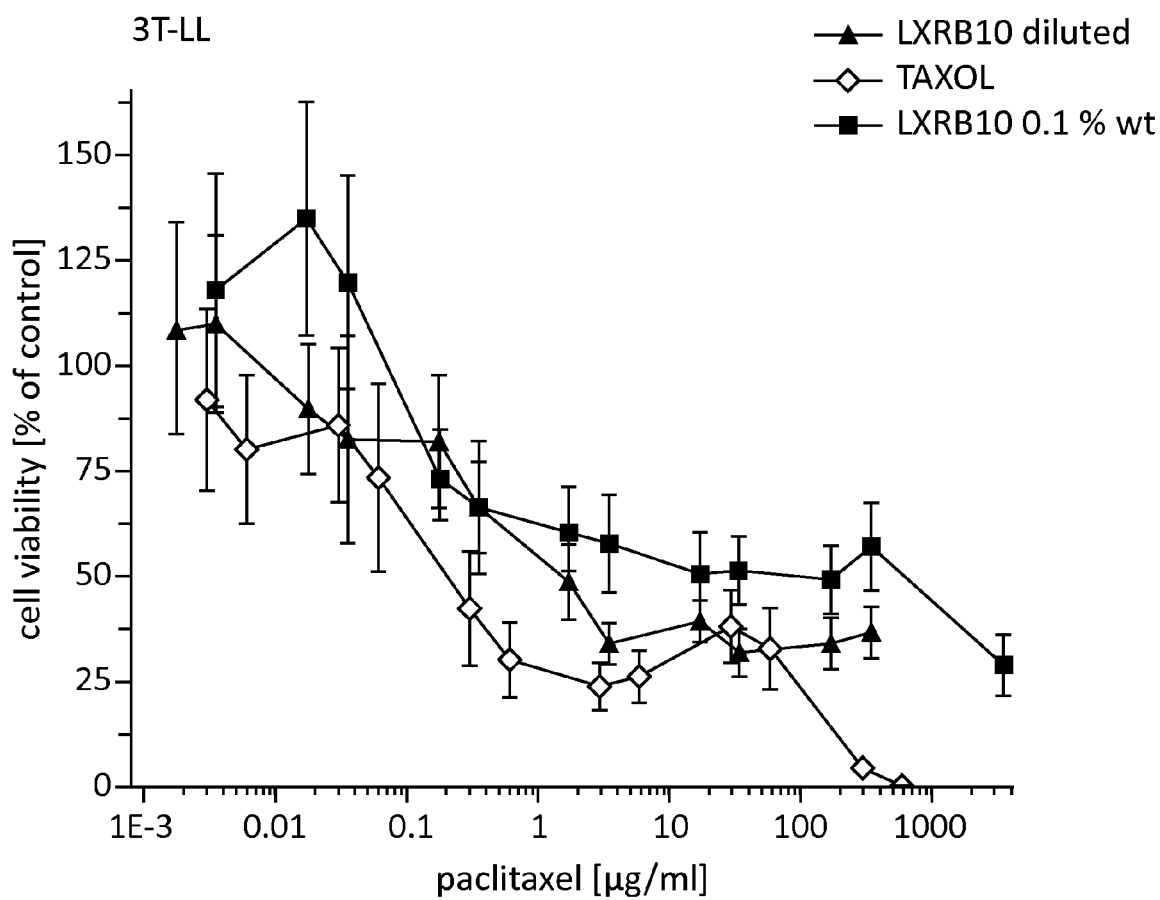
FIG. 4C is a graph demonstrating the toxicity of paclitaxel (Taxol®) alone, paclitaxel (Taxol®) solubilized in LXRB10 (0.1% wt), or paclitaxel (Taxol®) solubilized in LXRB10 diluted.
Figure 5A:
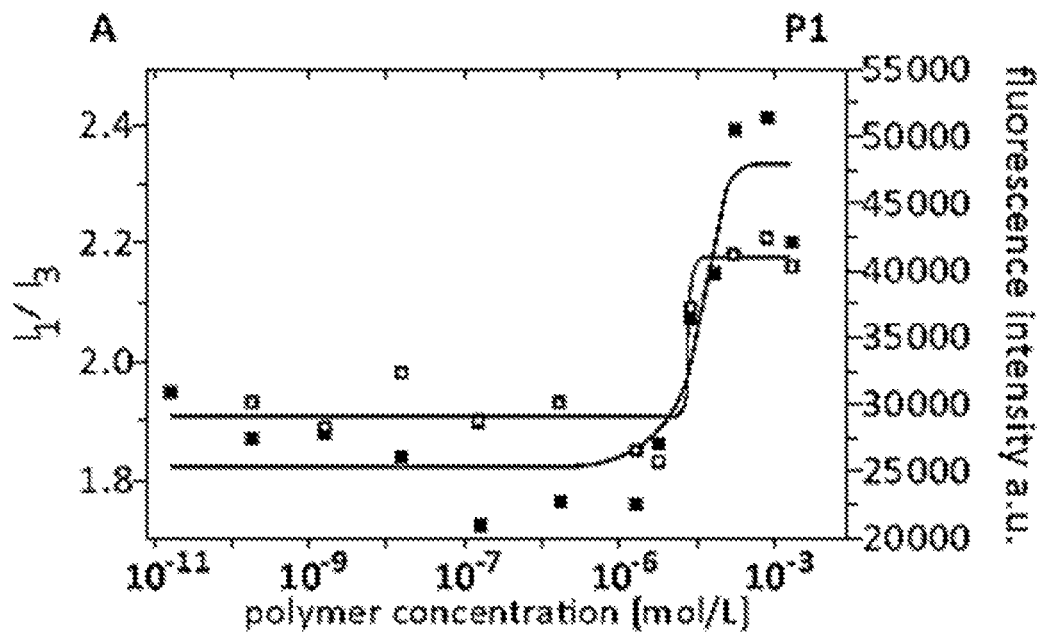
Figure 5B:
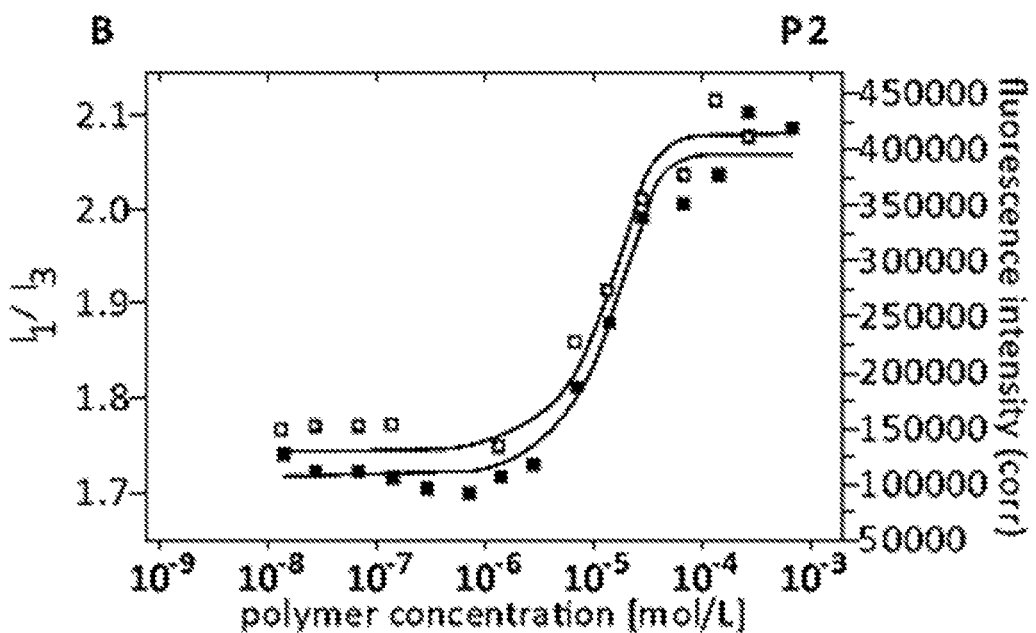
Figure 5C:
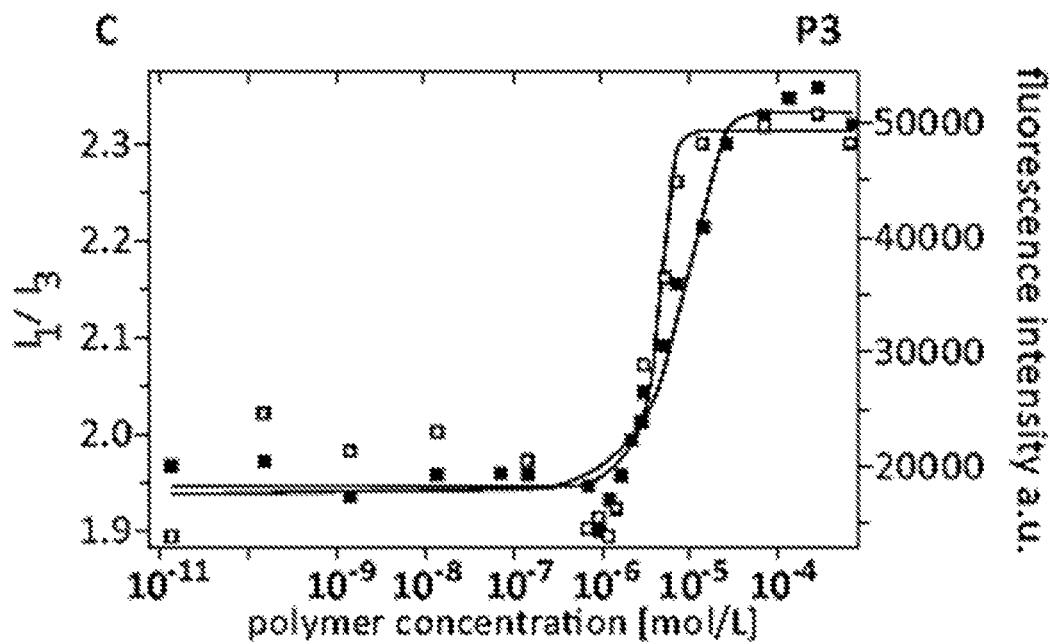
Figure 5D:
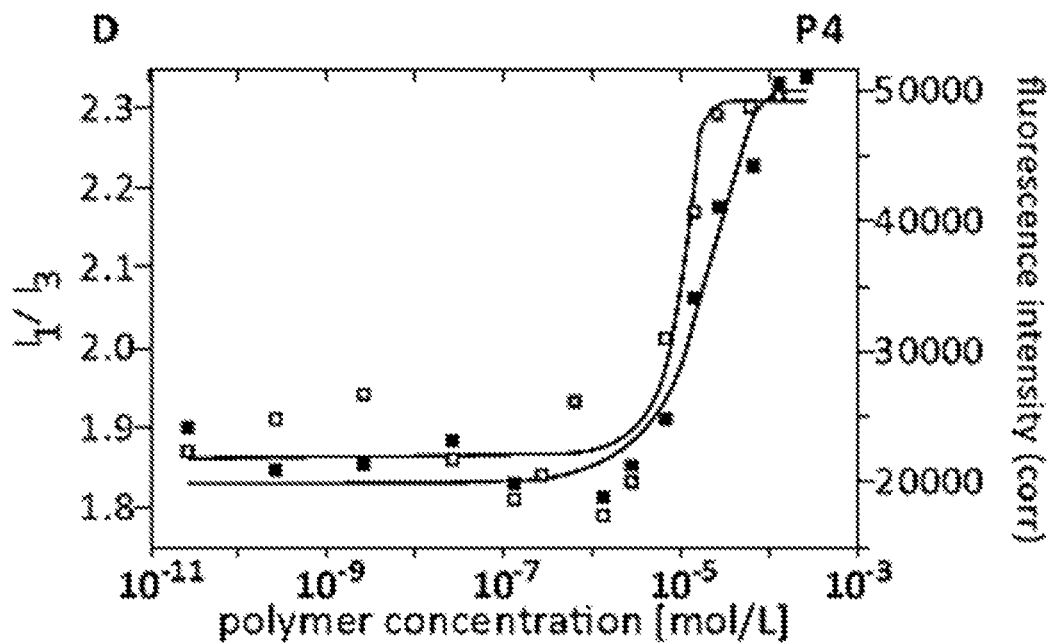

The toxicity of paclitaxel solubilized in LXRB20 was also compared to the toxicity of Cremophor EL®. As seen in FIGS. 4A and 4B, paclitaxel solubilized in LXRB20 has a toxicity comparable to paclitaxel solubilized in Cremophor EL® on the MCF-7 human breast cancer cell line. FIG. 4C demonstrates that paclitaxel solubilized in LXRB 10, even when diluted, has a comparable IC$_{50}$ (approx. 0.1 μg/ml/1 nM) to paclitaxel alone.

EXAMPLE 9

As stated herein, a majority of most potent drugs against serious diseases share a common flaw, which is a lack of water solubility. Thus, such drugs need to be formulated for parenteral administration. One prominent example in cancer chemotherapy is paclitaxel (PTX), a natural product of the bark of the pacific yew taxus brevifolia. It has a reported solubility in water of only 0.3 μg to 1 μg/mL, albeit depending on its crystallization state (Liggins et al. (1997) J. Pharm. Sci, 86:1458-1463; Lee et al. (2003) Pharm. Res, 20:1022-1030). Currently, two modi operandi of paclitaxel formulation are approved for human use. Typically, a mixture of Cremophor EL® (polyoxyethylated castor oil) and dehydrated ethanol is used to solubilize 6 mg/mL paclitaxel. However, serious formulation-evoked side effects have been reported (Pradis et al. (1998) Anticancer Res, 18:2711-2716; Gelderblom et al. (2001) Eur. J. Cancer, 37:1590-1598; Hennenfent et al. (2006) Ann. Oncol, 11:135-74), which make extensive premedication necessary. ABI-007 (Abraxane™, Abraxis Bioscience, Los Angeles, Calif.), a nanoparticulate (size approx. 130 nm) albumin-paclitaxel formulation can overcome some of the problems encountered with Taxol® and is currently approved for treatment of relapsed breast cancer. It allows injections of paclitaxel at a concentration of 5 mg/mL. However, it still contains 90% wt. of carrier and only 10% wt. of drug. Herein, novel nanoformulations are reported which have unprecedentedly high loading capacity and contain at least 40% wt. of paclitaxel incorporated in non-toxic, small (20 nm diameter) poly(2-oxazoline)-based polymeric micelles. The formulations are very simple to prepare, stable, and can be lyophilized and readily re-dispersed without cryoprotectants. They are shown to deliver at least 8 mg/mL of drug in the active form to treat cancer.

Poly(2-oxazoline)s have recently attracted increasing attention for biomedical applications. Of particular interest are hydrophilic poly(2-methyl-2-oxazoline) (PMeOx) and poly(2-ethyl-2-oxazoline) (PEtOx) as they exhibit stealth (Zalipsky et al. (1996) J. Pharm. Sci, 85:133-137; Woodle et al. (1994) Bioconjugate Chem, 5:494-496) and protein repellent (Komadi et al. (2008) Langmuir 24:613-616) effects similar to polyethylene glycol, arguably the most commonly used polymer for injectable drug delivery systems. In contrast to polyalkylene glycols the poly(2-oxazoline)s hydrophobicity can be gradually fine-tuned in a very broad range.

Materials and Methods Preparation of Polymer Amphiphiles

The polymerizations and work-up procedures were carried out according to the procedure described previously (Luxenhofer et al. (2006) Macromolecules, 39:3509-3516). The preceding "General Materials and Methods" section provides further details regarding the materials and methods which follow.

Preparation of methyl-P [MeOx$_{27}$-b-BuOx$_{12}$-b-MeOx$_{27}$]-piperidine (P1)

As an example, the preparation of methyl-P [MeOx$_{27}$-b-BuOx$_{12}$-b-MeOx$_{27}$]-piperidine (P1) was performed as follows. Under dry and inert conditions 32.2 mg (0.2 mmol, 1 eq) of methyl trifluoromethylsulfonate (methyl triflate, MeOTf) and 440 mg (5.17 mmol, 26 eq) of 2-methyl-2-oxazoline (MeOx) were dissolved in 3 mL dry acetonitrile at room temperature. The mixture was subjected to microwave irradiation (150 W maximum, 130° C.) for 15 minutes. After cooling to room temperature, the monomer for the second block, 2-butyl-2-oxazoline (256 mg, 2.01 mmol, 10 eq) was added and the mixture was irradiated the same way as for the first block. The procedure was repeated for the third block with 442 mg (5.19 mmol, 26 eq). Finally, P1 was terminated by addition of 0.1 mL piperidine (1.01 mmol, 5 eq) at room temperature. After stirring overnight, an excess of K$_2$CO$_3$ was added and the mixture was allowed to stir for several hours. The mixture was concentrated after filtration and added to 3 mL of chloroform. After precipitation from cold diethyl ether (approx. 10 times the amount of polymer solution) the product was obtained by centrifugation. The precipitation was performed in triplicate and the polymer was obtained as a colorless powder (792 mg, 67%, $M_{th}$ =5.8 kg/mol) after lyophilization from water.

GPC (DMAc): $M_n$=8.5 kg/mol (PDI $1.2_1$); $^1$H-NMR (CDCl$_3$, 298 K); δ=3.45 (br, 255H, (N—CH$_2$CH$_2$)); 3.04/2.95 (m, 3H, N—CH$_3^{Ini}$); 2.43-1.86 (m, 212H, CO—CH$_3$, CO—CH$_2$, CH$_2^{Pid}$); 1.56 (br, 29H, CH$_2$—CH$_2$—CH$_2$—); 1.32 (br, 28H, —CH$_2$—CH$_3$); 0.91 ppm (br, 37H, —CH$_3^{butyl}$), $M_n$=6.2 kg/mol (MeOx$_{27}$-b-BuOx$_{12}$-b-MeOx$_{27}$).

Preparation of Methyl-P[MeOx$_{37}$-b-BuOx$_{23}$-b-MeOx$_{37}$]-piperidine (P2)

P2 was obtained in a similar manner using 24 mg MeOTf (0.146 mmol, 1 eq), 333 mg MeOx (3.91 mmol, 27 eq, 1$^{st}$ block), 286 mg BuOx (2.25 mmol, 15 eq, 2$^{nd}$ block) and 333 mg MeOx (3.91 mmol, 27 eq, 3$^{rd}$ block) and 80 μL of piperidine as terminating reagent. The product was obtained as a colorless solid (795 mg, 83%, $M_{th}$=6.6 kg/mol).

GPC (DMAc): $M_n$=10.4 kg/mol (PDI $1.1_8$); $^1$H-NMR (CDCl$_3$, 298 K): δ=3.44 (br, 360H, (N—CH$_2$CH$_2$)); 3.03/2.94 (m, 3H, N—CH$_3^{Ini}$); 2.33-1.9 (m, 279H, CO—CH$_3$, CO—CH$_2$, CH$_2^{Pid}$); 1.55 (br, 47H, CH$_2$—CH$_2$—CH$_2$—); 1.32 (br, 45H, —CH$_2$—CH$_3$); 0.91 ppm (br, 68H, —CH$_3^{butyl}$), $M_n$=9.3 kg/mol (MeOx$_{37}$-b-BuOx$_{23}$-b-MeOx$_{37}$).

Preparation of Methyl-P[MeOx$_{36}$-b-BuOx$_{30}$-b-MeOx$_{36}$]-piperidine (P3)

P3 was prepared accordingly using 24.7 mg methyltriflate (0.150 mmol, 1 eq) and 334 mg 2-methyl-2-oxazoline (3.9 mmol, 26 eq, 1$^{st}$ block). An aliquot of 136 mg (5% w/w) of the reaction mixture was removed for analysis of the first block with NMR and GPC. The same procedure was performed after the second block (364.4 mg BuOx; 2.87 mmol, 20 eq, 10% w/w analyzed). Block three (306.9 mg MeOx; 3.6 mmol, 28 eq) was added, the polymerization was terminated using 80 μL piperidine and the product was obtained as a colorless solid (598 mg, 65%, $M_{th}$=6.6 kg/mol).

GPC (DMAc): $M_n$=9.9 kg/mol (PDI $1.2_3$); $^1$H-NMR (CDCl$_3$, 298 K): δ=3.45 (br, 405H, (NCH$_2$CH$_2$)); 3.03/2.95 (m, 3H, N—CH$_3^{Ini}$); 2.43-1.86 (m, 329H, CO—CH$_3$, CO—CH$_2$, CH$_2^{Pid}$); 1.57 (br, 63H, CH$_2$—CH$_2$—CH$_2$—); 1.32 (br, 60H, —CH$_2$—CH$_3$); 0.91 ppm (br, 88H, CH$_3^{butyl}$), $M_n$=10.0 kg/mol (MeOx$_{36}$-b-BuOx$_{30}$-b-MeOx$_{36}$).

Preparation of Methyl-P[EtOx$_{50}$-b-BuOx$_{19}$]-piperazine (P4)

P4 was prepared accordingly from 10 mg MeOTf (61 μmmol, 1 eq), 321 mg 2-ethyl-2-oxazoline (3.24 mmol, 53 eq, 1$^{st}$ block) and 157 mg BuOx (1.23 mmol, 20 eq, 2$^{nd}$ block), using 150 mg piperazine as a terminating reagent. For precipitation, a solvent mixture of cyclohexane and diethyl-ether (50/50, v/v) was used. The product was obtained as a colorless solid (yield 0.36 g, 77%, $M_{th}$=7.8 kg/mol).

GPC (DMAc): $M_n$=11.5 kg/mol (PDI 1.09); $^1$H-NMR (CDCl$_3$, 298 K): δ=3.45 (br, 276H, (NCH$_2$CH$_2$)); 3.04/2.95 (m, 3H, N—CH$_3^{Ini}$); 2.5-2.2 (m, 144H, CO—CH$_2$—CH$_3$, CO—CH$_2$, CH$_2^{Pid}$); 1.58 (br, 37H, CH$_2$—CH$_2$—CH$_2$—); 1.34 (br, 41H, —CH$_2$—CH$_3$); 1.11 (br, 151H, CO—CH$_2$—CH$_3$); 0.91 ppm (br, 56H, —CH$_3^{butyl}$), $M_n$=7.5 kg/mol (EtOx$_{50}$-b-BuOx$_{19}$).

Preparation of Methyl —P[MeOx$_{42}$-b-BuOx$_{18}$-b-MeOx$_{42}$]-piperazine (P5)

P5 was prepared accordingly from 14 mg MeOTf (85 μmmol, 1 eq), 190 mg MeOx (2.2 mmol, 26 eq, 1$^{st}$ block), 236 mg BuOx (1.86 mmol, 22 eq, 2$^{nd}$ block) and 192 mg MeOx (2.3 mmol, 27 eq, 3$^{rd}$ block) using 200 mg piperazine as a terminating reagent. The product was obtained as a colorless solid (0.47 g, 69%, $M_{th}$=8.0 kg/mol)

GPC (DMAc): $M_n$=14.7 kg/mol (PDI $1.2_2$); $^1$H-NMR (CDCl$_3$, 298 K): δ=3.45 (br, 408H, (NCH$_2$CH$_2$)); 3.04/2.95 (m, 3H, N—CH$_3^{Ini}$); 2.4-2.0 (m, 307H, CO—CH$_3$, CO—CH$_2$, CH$_2^{Pid}$); 1.56 (br, 37H, CH$_2$—CH$_2$—CH$_2$—); 1.33 (br, 37H, —CH$_2$—CH$_3$); 0.91 ppm (br, 53H, —CH$_3^{butyl}$), $M_n$=9.5 kg/mol (MeOx$_{42}$-b-BuOx$_{18}$-b-MeOx$_{42}$).

TABLE 3

Analytical data and composition of amphiphilic block copolymers used

| Polymer Composition | $M_n^a$ [kg/mol] | $M_n^b$ [kg/mol] | PDI$^b$ | Yield [%] |
|---|---|---|---|---|
| P1 MeOx$_{27}$-b-BuOx$_{12}$-b-MeOx$_{27}$ | 6.2 | 8.5 | 1.21 | 67 |
| P2 MeOx$_{37}$-b-BuOx$_{23}$-b-MeOx$_{37}$ | 9.3 | 10.4 | 1.18 | 83 |
| P3 MeOx$_{36}$-b-BuOx$_{30}$-b-MeOx$_{36}$ | 10.0 | 9.9 | 1.23 | 65 |
| P4 EtOx$_{50}$-b-BuOx$_{19}$ | 7.2 | 11.5 | 1.09 | 77 |

$^a$as determined by endgroup analysis from $^1$H-NMR spectroscopy.
$^b$as determined by gel permeation chromatography.

Attachment of Fluorophore (Atto425)

Labeling of piperazine terminated polymers P4 and P5 was performed in anhydrous dimethylformamide (DMF) and diisopropylethylamine (DIPEA) with 1.2 eq of reactive dye (Atto425-NHS ester, Sigma-Aldrich, St. Louis, Mo.) per eq of polymer. Reaction was stirred for 3 days at room temperature in the dark and diluted with methanol. Remaining free dye was removed by gel filtration (Sephadex™ LH20) in methanol which was performed in triplicate.

Critical Micelle Concentration (cmc) Measurement; Pyrene Assay:

The critical micelle concentration (cmc) was determined using described method (Kabanov et al. (1995) Macromolecules, 28:2303-2314; Colombani et al. (2007) Macromolecules, 40:4338-4350). In short, a pyrene solution in acetone (2.5 mM) was added to vials and the solvent was allowed to evaporate. Polymer solutions at appropriate concentrations in assay buffer were added to the vials so that a final concentration of $5 \times 10^{-7}$ M of pyrene was obtained. The solutions were incubated at 25° C. (22 hours) and the pyrene fluorescence spectrum were recorded using a Fluorolog®3 (HORIBA-JobinYvon) λ=333 nm, $λ_{em}$=360-400 nm, slit-width(ex)=slit-width(em)=1 nm, step width 0.5 nm. Typically, five spectra of each data point were averaged (integration time 0.1 seconds, if necessary 10 spectra with 0.2 seconds integration), the cmc is assumed where a steep increase in fluorescence intensity is observed. Furthermore, the fluorescence intensity of the $I_1$ band was compared to the intensity of $I_3$ band which gives an estimate of the polarity of the environment of the pyrene probe.

Drug Solubilization Studies

Drug-polymer solutions were prepared using the thin film method. Appropriate amounts of polymer and paclitaxel (stock solution 5 mg/mL) were solubilized in minimum amounts of acetonitrile (ACN). The solvent was removed in a stream of air under mild warming and the films were subjected to 0.2 mbar for at least 3 hours to remove residual solvent. Subsequently 200 μL of assay buffer (aqueous solution, containing 122 mM NaCl, 25 mM $Na_2CO_3$, 10 mM HEPES, 10 mM glucose, 3 mM KCl, 1.4 mM $CaCl_2$, and 0.4 mM $K_2HPO_4$, pH=7.4) were added to obtain final polymer concentration as mentioned in the main text. At higher paclitaxel concentration solubilization was facilitated by incubation of the solutions for 50-60° C. for typically 5-10 minutes. The clear solutions were filtered through HPLC syringe filters (0.45 (im pore size) and subjected to HPLC analysis. In view of future application in vivo, it is also noteworthy that substitution of the relatively toxic ACN with the more benign EtOH as a common solvent before film formation did not diminish loading efficiencies.

HPLC Analysis of Drug Solubilization

HPLC analysis was carried out under isocratic conditions using a Shimadzu system comprising a SCL-10A system controller, SIL-10A autoinjector, SPD-10AV UV detector and two LC-10 AT pumps. As stationary phase a Nucleosil® C18-5µ column was used (250 mm×4 mm), as a mobile phase an acetonitrile/water mixture (55/45, v/v) was applied. Detection was performed at 220 nm. The amount of paclitaxel in the polymer solution was calculated using a calibration curve obtained with known amounts of paclitaxel dissolved in acetonitrile and analyzed accordingly.

NMR

For NMR analysis, paclitaxel containing polymer thin films were dissolved in the respective deuterated solvents (acetonitrile-$d_3$, chloroform-$d_1$ or 20% (v/v) $D_2O$ in $H_2O$).

Dynamic Light Scattering

Dynamic light scattering was performed using a Zetasizer Nano-ZS (Malvern Instruments Inc., Southborough, Mass.) at room temperature.

Cell Culture

MCF7/ADR cells (derived from human breast carcinoma cell line, MCF7 (ATCC HT-B22) by selection with Doxorubicin, was kindly presented by Y. L. Lee (William Beaumont Hospital, Royal Oak, Mich.). Cells were maintained in Dulbecco's Modified Eagle's Medium (DMEM), containing 10% heat inactivated fetal bovine serum (FBS) and 1% penicillin/streptomycin as described elsewhere. All tissue material media was obtained from Gibco Life Technologies, Inc. (Grand Island, N.Y.).

MTT Assay

MCF7/ADR were seeded in 96 well plates ($10^4$ cells per well) and were allowed to reattach for 24 hours. Treatment solutions were prepared from a 1 mg/mL polymer stock solution in assay buffer (containing 122 mM NaCl, 25 mM $NaHCO_3$, 10 mM glucose, 10 mM HEPES, 3 mM KCl, 1.2 mM $MgSO_4$, 1.4 mM $CaCl_2$, and 0.4 mM $K_2HPO_4$, pH 7.4) by appropriate dilution with media (Dulbecco's Modified Eagle's Medium (DMEM), supplemented with 10% fetal bovine serum (FBS), 25 mM HEPES and penicillin/streptomycin). The cells were incubated for 48 hours with 200 µL of treatment solution. After discarding the treatment solution, cells were washed thrice with PBS. FBS-free DMEM (100 µL/well) as well as 25 µL of a 5 mg/mL solution of 3-(4,5-dimethylthiazol-2-yl)-2,5-diphenyltetrazolium bromide (MTT, Invitrogen, Eugene, Oreg.) in PBS were added and the cells incubated at 37° C. for 2 hours. The media was discarded subsequently and replaced with 100 µL of solvent (25% v/v DMF, 20% w/v SDS in $H_2O$). The purple formazan product was allowed to dissolve overnight and the absorbance at 570 nm was obtained using a plate reader (SpectraMax® M5, Molecular Devices). Positive control were cells treated with media alone, negative control were wells without cells. Each concentration was repeated in four wells, results are expressed as mean±SEM.

Flow Cytometry

For the analysis of cellular uptake by flow cytometry, MCF7/ADR cells were plated in 24 well plates ($7.5×10^4$ per well) two days prior to the experiment. Cells were treated with 200 µL of polymer solutions in FBS free media. In the case of experiment performed at 4° C., the cells were washed 3 times with ice cold PBS and incubated with ice-cold polymer solution. Cells were incubated for 60 minutes or the indicated time at 37° C./5% $CO_2$ or 4° C., washed subsequently thrice with ice-cold PBS, trypsinized and centrifuged. The cell pellet was resuspended in 400 µL PBS with 1% bovine serum albumin, split in two aliquots and analyzed using flow cytometry. Each data point was performed in triplicate. The mean fluorescence intensity was determined using a BD Biosciences LSRII digital flow cytometer operating under FACSDiVa® software version 6.1 (San Jose, Calif.). Excitation was provided by a 25 mW Coherent VioFlame™ PLUS violet laser (405 nm), and emission collected through a 450/50 bandpass filter. Approximately 10,000 digital list mode events were collected and the data gated on forward and side scatter parameters to exclude debris and dead cells. Control cells without labeled polymers were used as the negative control for autofluorescence. Data analysis was performed using DiVa® software.

Confocal Fluorescence Microscopy

For live cell confocal microscopy (Carl Zeiss LSM 510 Meta, Peabody, Mass.) MCF7/ADR cells ($4×10^4$) were plated in Lab-Tek Chambered Cover Glasses dishes (Fischer Scientific, Waltham, Mass.) and after two days (37° C., 5% $CO_2$) were exposed for 60 minutes to Atto-425 labeled polymer solutions in FBS free media. Subsequently, cells were washed (3×PBS) and kept in complete media for imaging using the confocal microscope. Alternatively, the cells were fixed with 4% paraformaldehyde solution for 10 minutes at room temperature, the PFA was substituted with PBS and the cells were kept at 4° C. in the dark until confocal microscopy was performed.

Results

Notably, the most hydrophobic poly(2-oxazoline)s contain in each repeating unit a highly polar amide motif in the backbone, which makes these compounds nonionic polysoaps. By combining different poly(2-oxazoline)s in block copolymer structures, a special type of polymeric surfactant was produced with amphiphilicity embedded both in the block copolymer architecture and in every repeating unit of each block. Specifically, four well-defined ABA-type triblock copolymers (P1-P3) and one diblock copolymer (P4) of molar masses ca. 8 to 10 kg/mol and low polydispersities (PDI=1.09-1.23) were synthesized by living cationic ring opening polymerization. The hydrophilic blocks (A) consisted of 50 to 80 units of PMeOx (P1-P3) or PEtOx (P4), and the hydrophobic block (B) consisted of 10 to 22 units of 2-butyl-2-oxazoline (PBuOx) (Table 3). All these polymers readily dissolve in water at room temperature at concentrations of up to 15-30 wt. %.

The homologue series of poly(2-alkyl-2-oxazoline)s share a polar amide motif and display a gradually increasing hydrophobicity as the alkyl side chains increase in length. The series starts from highly hydrophilic poly(2-methyl-2-oxazoline), followed by slightly amphiphilic thermo-responsive poly(2-ethyl-2-oxazoline), then by more hydrophobic poly(2-isopropyl-2-oxazoline) and poly(2-propyl-2-oxazoline) and finally, by poly(2-butyl-2-oxazoline), which shows no marked aqueous solubility. The lower critical solution temperatures (LCST) depend on the molecular mass and the polymer structure (Huber et al. (2008) Colloid Polym. Sci, 286:395-402). LCSTs for the polymers are −70° C. for poly (2-ethyl-2-oxazoline), −40° C. for poly(2-isopropyl-2-oxazoline), and −25° C. for poly(2-propyl-2-oxazoline).

In order to prove that polymers P1-P4 self-assemble in polymeric micelles in aqueous solutions, pyrene was used as a highly hydrophobic fluorescence probe. The onset of increasing pyrene fluorescence intensity is typically observed as the polymer concentration reaches the critical micelle concentration (cmc) (Colombani et al. (2007) Macromolecules 40:4338-4350). Cmc's for polymers P1-P4 were found to be 100 mg/L (15 μmole), 20 mg/L (2.7 μmol), 1 mg/L (1 μmol), and 6 mg/L (0.7 μmol), respectively (FIG. 5A-5D). FIG. 1 shows the fluorescence intensity and $I_1/I_3$ ratios of pyrene solutions (5×10-7 M in phosphate buffered saline (PBS)) in dependence of concentration of block copolymers as used in the context of the invention at 25° C.

These very low cmc values are desirable when a parenteral application is considered, as any systemically administered polymer solution will be diluted rapidly by 100 to 1000 times. The ratio of $I_1$ and $I_3$ bands in the fluorescence emission spectrum of pyrene was used to test polarity of the environment of the pyrene probe. Indeed, the fine structure of the pyrene fluorescence spectra is known to correlate well with the permanent dipolar moment of the environment (typically solvent), while it correlates only poorly with the permittivity of the medium (Kalyanasundaram et al. (1977) J. Am. Chem. Soc, 99:2039-2044). When pyrene is in an aqueous or similarly polar environment, the $I_1/I_3$ ratio is found between 1.6 and 1.9, although it has been shown that the ratio is influenced both by environmental and instrumental conditions (Street et al. (1986) Analyst 111:1197-1201). When polymer aggregates are formed, a less polar environment is usually available for pyrene into which it is partitioned. As a result, the $I_1/I_3$ ratio usually decreases concomitantly with the increasing overall fluorescence intensity. Quite surprisingly, the opposite was observed. As the fluorescence intensity increased, the $I_1/I_3$ ratio also increased up to 2.35 (FIG. 6A). Moreover, the $I_1/I_3$ ratio increased as the size of "hydrophobic" BuOx block increased. This phenomenon is unique for polymeric micelles, or for any other media. It indicates that, as aggregates of P1-P4 form, the pyrene probe is translocated into an amphipolar environment, which is sufficiently hydrophobic to solubilize pyrene yet, more polar than water. Based on the $I_1/I_3$ ratio this environment is similar to a polar solvent, dimethylsulfoxide, or ionic liquid, 1-butyl-2,3-dimethylimidazolium chloride (FIG. 6B), rather than nonopolar solvent, hexane, or regular polymeric micelles of Pluronic® P85 (FIG. 6A). Such an environment is probably heterogeneous on the very small scale and is formed due to intrinsic amphiphilicity in every repeating unit of BuOx blocks of poly(2-oxazoline)s. Therefore, pyrene entraps in the hydrophobic domains formed by butyl moieties yet still comes in contact with the polar amide motifs. Consequently, replacement of butyl for 2-nonyl-2-oxazoline (NOx) in the core forming block of $NOx_{10}$-b-$MeOx_{32}$ completely reverses the $I_1/I_3$ ratio (FIG. 6A), presumably because now pyrene can be completely immersed in a hydrophobic domain formed by the bulky nonyl moieties. In contrast, while the butyl side chains lead to hydrophobic compartments, the polymer backbone remains hydrated due to the presence of the polar amide motif in every repeating unit, creating unique amphipolar environment for the solubilized molecules.

As stated above, observed $I_1/I_3$ ratios of pyrene fluorescence signals vary based on solvents and polymeric micelles. By way of example, hexanes yield an $I_1/I_3$ ratios of about 0.6. For polymeric micelles, values varying between 0.8 up to 1.5 are typically observed (e.g., Pluronic® block copolymers from about 1.2-1.5). Only few solvents yield ratios that are around or slightly above water (about 1.6-1.9), including dimethylsulfoxide (about 1.9-2.05), acetonitrile and in some cases, ionic liquids (about 1.8-2.1). 2-butyl-2-oxazoline based polymer amphiphiles were found to give much higher ratios than observed in water, indicating an amphipolar environment present in the micelle. 2-nonyl-2-oxazoline based polymer amphiphiles exhibited a ratio from about 1.2-1.4.

One should expect that the P1-P4 aggregates are highly hydrated due to the presence of the polar amide motif in the repeating units of poly(2-oxazoline)s. This was corroborated by the results of an $^1$H-NMR study (FIG. 7). Clearly, when spectra of polymers are obtained under conditions when aggregates are present, the signals of the butyl side chains are markedly attenuated (signals 1-4 vs. 1'-4; FIGS. 7A and 7B) compared to the corresponding signals of the hydrophilic blocks (signal 6/7 vs. 6'/7'). The signal originating from the polymer main chain (signal 5 and 5', present in both hydrophilic and hydrophobic blocks), however, appears to be subject to less pronounced attenuation. These results indicate that the side chains of BuOx blocks segregate in domains with restricted solvent access. However, the fact that the signals remain well observable suggests that the "hydrophobic" part of the micelle is in fact well hydrated.

Surprisingly, these aggregates exhibited remarkable capability for solubilization of paclitaxel. To prepare drug loaded polymeric micelles a thin-film dissolution method was used. Poly(2-oxazoline)s are readily soluble in a wide range of organic solvents, including ethanol, dimethylsulfoxide, chloroform, acetonitrile and others, which greatly facilitates their formulation with water-insoluble drugs. Solutions of polymers and paclitaxel were simply combined in acetonitrile or ethanol and then the solvent was removed under a stream of air and vacuum. Upon addition of water the polymer-drug film dissolved rapidly and completely, if the concentration of paclitaxel did not exceed 4 mg/mL. At higher concentrations mild heating (<60° C.) was used to facilitate the process for P1-P3. For P5, an LCST-like behavior was observed around 50° C.

Initially, it was attempted to solubilize 4, 7 and 10 mg/mL paclitaxel with 10 mg/mL P2. Up to concentrations of 7 mg/mL paclitaxel, clear solutions were obtained after mild heating for a short time. Under these conditions the solubilization of paclitaxel was complete as confirmed by high performance liquid chromatography (HPLC) (FIG. 8A). Only at 10 mg/mL paclitaxel some clear crystals remained undissolved even after 30 minutes heating at 60° C. However, an extraordinary solubilization of paclitaxel of 8.2 mg/mL was still obtained, indicating that the resulting formulation consists of at least 40% wt. paclitaxel. Similar results were obtained with the other polymers including PI, having only 12 units in the BuOx block (FIG. 8B). Even at polymer concentrations as low as 2 mg/mL, excellent loading efficiencies and total drug loading of almost 30% wt. were obtained (FIGS. 8C and 8D). Notably, upon dilution of the drug-polymer solutions with acetonitrile (ACN) for subsequent HPLC analysis, the dissolved paclitaxel instantaneously precipitated at concentrations exceeding 1 mg/mL. This is a simple but convincing proof that the paclitaxel is indeed dissolved in polymer micelles which disintegrate upon addition of small amounts of ACN. However, upon appropriate dilution with water, the solutions remained clear and where analyzed after passing through HPLC-syringe filters. As compared to Cremophor EL® and Abraxane™, the poly(2-oxazoline) block copolymers can reduce the amount of excipient needed to solubilize paclitaxel by approx. 100 and 9 times, respectively.

These drug loaded micelles are very small in size (approx 20-50 nm) and show a narrow size distribution (PD≈0.04-

0.12) as determined by the dynamic light scattering (FIGS. 9A-9D). Such materials are excellently suited for biomedical applications, and in particular systemic administration. P1-P4 alone were not cytotoxic at concentrations of up to 20 mg/mL and 24 hours incubation with different cell lines: MCF7/ADR (human, multidrug resistant) and MCF7 (non-resistant human adenocarcinoma), MDCK (Madin-Darby canine kidney) (FIG. 10) and 3TLL (murine). A fluorescently labeled sample was also prepared. It was as shown that the micelles were readily and rapidly (minutes) taken up into the cells (FIG. 11). For P4 and P5 the cellular uptake was observed even at nanomolar concentrations and followed a typical dose dependent manner. Moreover, the uptake was very fast (within minutes) and temperature dependent, albeit complete inhibition of cellular uptake of P4 was not observed at 4° C.

Confocal microscopy confirmed that polymers are internalized. They were found predominantly in small, primarily perinuclear vesicles, although in some cases, e.g. P4, a marked diffuse staining was also observed in the cytosol suggesting that the polymer was not restricted to vesicles (FIG. 12).

In stark contrast to the plain polymers, the paclitaxel-loaded micelles displayed a pronounced, concentration-dependent toxicity with respect to drug-resistant cells, MCF7/ADR and sensitive cells, MCF7 and 3T-LL. For example, after 24 hour incubation with paclitaxel-loaded P2, P3 and P4, $IC_{50}$ values in the low μmolar range were observed. Commercially available Taxol® was used as a control and a comparable $IC_{50}$ was observed. However, in contrast to the poly(2-oxazoline) block copolymers, a Cremophor® EL/ethanol mixture (1/1; v/v) contained in the Taxol® formulation alone (no paclitaxel) has shown considerable toxicity. The paclitaxel-loaded micelles were lyophilized without the need for cryoprotectants and simply be re-dispersed in water or saline without compromising drug loading, particle size, or in vivo drug efficacy (FIG. 13). The antitumor effect of paclitaxel-loaded micelles was examined in C57B1/6 mice with subcutaneous Lewis Lung carcinoma tumors. Both the poly(2-oxazoline)-based formulation and the regular Taxol® formulation induced significant tumor inhibition on day 15.

The molar masses of these polymers are well below the renal threshold (approx. 65 kDa for globular proteins, 4 nm absolute size) and their polydispersity is reasonably low. Thus, it can be expected that the unimers are readily cleared via the kidney and the drug delivery vehicle can be disposed of appropriately by the organism after it served its purpose.
Solubilization of Cyclosporin A Solubilization of Cyclosporin A (Alexis Corporation San Diego, Calif., order number 380-002-G001) was performed accordingly using the film method. Using P2 and Cyclosporin A clear and stable solutions were obtained.

HPLC analysis of Cyclosporin A solutions obtained using the protocol described above were performed using as a mobile phase an acetonitrile/water mixture (90/10, v/v) at 70° C. With 5 mg/mL of P2, 1.03 mg/mL of Cyclosporin A could be solubilized. This corresponded to an 82% loading efficiency and 17% loading (w/w). Thus, an approx. 120 fold increase of Cyclosporin A solubility was achieved using P2.
Solubilization of Amphotericin B Solubilization of amphotericin B with P2 was carried out using solvent exchange by dialysis. P2 (10.2 mg) and amphotericin B trihydrate (2.1 mg, Riedel-de Haën, Seelze, Germany, order number 46006) were dissolved in 250 μL dimethylsulfoxide (DMSO) to yield a clear, yellow solution. A total of 750 μL of deionized water was added, after 1004 the mixture became turbid. The resulting mixture was transferred into a dialysis bag (MWCO 3500 g/mol). The solution was dialyzed against 2 L deionized water (water exchanged at 2 h, 4 h and 22 h). After a total of 50 h, the suspension (4 mL) was recovered from the bag. An aliquot of 500 μL was filtered (0.45 μm) to remove particles and the clear, yellow solution was freeze dried to yield 1 mg of yellow foam-like solid. The residue was dissolved in 200 μL DMSO and the amphotericin B was quantified spectrophotometrically using the absorbance at 410 nm. The dialyzed solution contained 366 μg Amphotericin B (18% (w/w) with respect to P2).

Another aliquot of 1 mL was freeze-dried (2.2 mg yellow foam) and dissolved subsequently in 100 μL deionized water. The polymer-drug foam dissolved rapidly and completely to give an intense yellow solution of low viscosity. Thus, without the need for cryoprotectants, 3.7 mg/mL of Amphotericin B could be solubilized using only 18.3 mg/mL P2. Using the same protocol, water solubility of Amphotericin B was determined to be approx. 0.4 μg/mL.

EXAMPLE 10

Animal Studies

All experiments were performed using female C57/B1/6 mice 11-12 weeks of age (Taconic Laboratories, Germantown, N.Y.). The animals were kept five per cage with an air filter cover under light (12-hour light/dark cycle) and temperature-controlled (22F1 8C) environment. All manipulations with the animals were performed under a sterilized laminar hood. Food and water were given ad libitum. The animals were treated in accordance to the Principles of Animal Care outlined by National Institutes of Health, and protocols were approved by the Institutional Animal Care and Use Committee of the University of Nebraska Medical Center. Lewis lung carcinoma cells (LLC 3T) were grown in T75 flasks and collected with HBSS. Cell suspensions ($1\times10^6$ per animal) were injected subcutaneously in a volume of 50 μL on the right flank. After tumors appeared, tumor sizes where recorded (day 1) and treatment solutions were injected at a doses of 10 mg/kg PTX in a volume of 100 μL on day 1, 4 and 7.

The in vivo anti-tumor effect of PTX-loaded micelles was examined in C57/B1/6 mice with subcutaneous Lewis Lung carcinoma tumors (FIG. 14). Both commercial (CrEl) and (P2-PTX) formulation significantly (p<0.05) decreased tumor burden after only one injection (day 4, tumor inhibition=72% and 63%, respectively). The tumors in the P2-PTX treated animals remained significantly smaller (p<0.05) than in the animals treated with the commercial product between days 11 and 25. It was found that the tumor inhibition by P2-PTX in this period to be approximately 70% as compared to 50-60% in the CrEl group. After 28 days, however, a sharp increase in the tumor burden of the animals in the P2-PTX regimen was observed and the same tumor inhibition in both treated groups was found.

FIG. 14A shows relative tumor weights of subcutaneous Lewis Lung carcinoma tumors in C57/B1/6 mice comparing negative controls (saline, P2 alone), treatment with POx solubilized PTX (P2-PTX) and commercial product (CrEl) at the same PTX doses (10 mg/kg). Arrows indicate times of injection. FIG. 14B shows the calculated tumor inhibition in treatment groups of P2, P2-PTX and CrEl at different points of time. Data represented as means±SEM (n=5).

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A composition comprising:
   a) at least one copolymer comprising at least one hydrophilic segment and at least one hydrophobic segment, wherein said hydrophilic segment is a hydrophilic poly(2-oxazoline), and wherein said hydrophobic segment is a hydrophobic poly(2-oxazoline) and
   b) at least one hydrophobic compound and/or active agent, wherein said hydrophobic compound has a solubility of less than 1 mg/mL in water at a pH range between 4 and 10 at 20° C.,
wherein
said hydrophilic segment is represented by the following structure of formula (I):

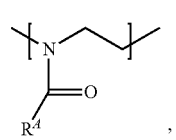

wherein $R^A$ is a hydrocarbon group, optionally substituted with —OH, —SH, —COOH, —NR'$_2$, —COOR', —CONR', —CHO, with R' representing H or $C_{1-3}$ alkyl, with $R^A$ being selected such that the repeating unit of formula (I) is hydrophilic and
said hydrophobic segment is represented by the following structure of formula (II):

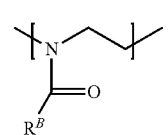

wherein $R^B$ is a hydrocarbon group selected such that the repeating unit of formula (II) is more hydrophobic than the repeating unit of formula (I), wherein the hydrocarbon group $R^B$ is selected from the group consisting of butyl, pentyl, hexyl, and heptyl and n represents an integer of 5 or more.

2. The composition of claim 1 further comprising at least one pharmaceutically acceptable carrier.

3. The composition of claim 1, wherein $R^A$ is selected, independently for each occurrence, from methyl and ethyl optionally substituted with —OH, —SH, —COOH, —NR'$_2$, —COOR', —CONR', —CHO, with R' representing H or $C_{1-3}$ alkyl.

4. The composition of claim 1, wherein $R^A$ is selected, independently for each occurrence, from methyl and ethyl and $R^B$ is selected from $C_{4-6}$ alkyl.

5. The composition of claim 1, wherein the copolymer is a block copolymer comprising at least 5 poly(2-oxazoline) block A units consisting of repeating units of formula (I) and at least 5 poly(2-oxazoline) block B units consisting of repeating units of formula (II).

6. The composition according to claim 5, wherein at least one block A is a poly(2-methyl-2-oxazoline) or a poly(2-ethyl-2-oxazoline) block and at least one block B is a poly(2-butyl-2-oxazoline) block.

7. The composition according to claim 5, wherein the block copolymer is an ABA triblock copolymer.

8. The composition of claim 1, wherein the at least one hydrophobic compound and/or active agent b) has a solubility of less than 50 μg/mL in water at a pH range between 4 and 10 at 20° C.

9. The composition of claim 8, wherein the at least one polymer forms micelles incorporating the active agent.

10. The composition of claim 9, wherein the micelles have a size of 5 to 500 nm.

11. The composition of claim 8, wherein the weight ratio of hydrophobic compound and/or active agent(s) to copolymer(s) is at least 3:7.

12. The composition of claim 1, wherein the active load, expressed as the ratio of the weight of the active agent to the sum of the weights of the active agent and the block copolymer×100, is 10% or more.

13. The composition of claim 1 which is a pharmaceutical or diagnostic composition containing a drug as an active agent.

14. The composition of claim 1, wherein said active agent is a therapeutic agent selected from the group consisting of peptides, peptoides, polyenes, macrocyles, glycosides, terpenes, terpenoids, aliphatic compounds, and aromatic compounds.

15. The composition of claim 1, wherein the active agent is a plant protection agent or compound.

16. The composition of claim 1, wherein said hydrophobic compound and/or active agent has a solubility of less than 10 μg/mL in water or aqueous media at a pH range between 4 and 10 at 20° C.

17. The composition of claim 1, wherein said copolymer is an amphiphilic block copolymer selected from the group consisting of a linear block copolymer, a star-like block copolymer, a graft block copolymers, a dendrimer block copolymer, and a hyperbranched block copolymer.

18. The composition of claim 11, wherein said copolymer is a triblock copolymer consisting of two hydrophilic segments and one hydrophobic segment.

19. The composition of claim 8, wherein said copolymer is an amphiphilic block copolymer and said hydrophobic compound and/or active agent form a soluble aggregate in aqueous media and wherein said aggregate has a size from about 5 nm to about 200 nm.

20. The composition of claim 19, wherein said aggregate has a size from about 10 nm to about 50 nm.

21. The composition of claim 1, wherein said hydrophobic compound and/or active agent and said copolymer are in a weight ratio of at least 3:7.

22. The composition of claim 1, wherein said hydrophobic compound and said copolymer are in a weight ratio of at least 4:6.

23. A composition comprising:
   a) at least one copolymer comprising at least one hydrophilic segment and at least one hydrophobic segment, wherein said hydrophilic segment is a hydrophilic poly(2-oxazoline), and wherein said hydrophobic segment is a hydrophobic poly(2-oxazoline); and b) at least one hydrophobic compound and/or active agent, wherein said hydrophobic compound has a solubility of less than 1 mg/mL in water at a pH range between 4 and 10 at 20° C., wherein said copolymer comprises the formula:

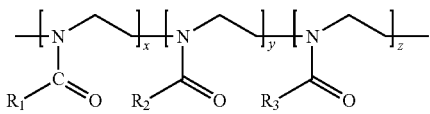

wherein x and y are independently selected between 5 and about 150; z is selected from between 5 and about 150; $R_1$ and $R_3$ are independently selected from the group consisting of —H, —OH, —NH$_2$, —SH, —CH$_3$, —CH$_2$CH$_3$, and an alkyl comprising 1 or 2 carbon atoms; and $R_2$ is a butyl group.

24. The composition of claim 23, wherein z is selected from between 10 and 100.

25. The composition of claim 23, wherein $R_1$ and $R_3$ are independently selected from the group consisting of —CH$_3$ and —CH$_2$CH$_3$.

26. The composition of claim 1, wherein the hydrophobic compound is a taxane.

27. The composition of claim 1, wherein the hydrophobic compound is a hydrophobic bioactive compound and the composition is suitable for parenteral administration for the treatment of a mammal in need of treatment or prevention of a disorder or disease.

28. A method for solubilizing at least one hydrophobic compound and/or active agent having a solubility of less than 1 mg/mL in water at a pH range between 4 and 10 at 20° C. comprising admixing the hydrophobic compound and/or active agent with at least one copolymer comprising at least one hydrophilic segment and at least one hydrophobic segment, wherein said hydrophilic segment is a hydrophilic poly(2-oxazoline), and wherein said hydrophobic segment is a hydrophobic poly(2-oxazoline), wherein said hydrophilic segment is represented by the following structure of formula (I):

wherein $R^A$ is a hydrocarbon group, optionally substituted with —OH, —SH, —COOH, —NR'$_2$, —COOR', —CONR', —CHO, with R' representing H or $C_{1-3}$ alkyl, and with $R^A$ being selected such that the repeating unit of formula (I) is hydrophilic and said hydrophobic segment has units of the formula (II):

wherein $R^B$ is a hydrocarbon group selected such that the repeating unit of formula (II) is more hydrophobic than the repeating unit of formula (I), wherein the hydrocarbon group $R^B$ is selected from the group consisting of butyl, pentyl, hexyl, and heptyl.

29. A method for delivering at least one hydrophobic compound and/or active agent to a subject, said method comprising administering the composition of claim 13 to said patient.

30. A method of treating a disorder or disease in a patient in need thereof, said method comprising the administration of the composition of claim 13 to said patient.

31. The method of claim 30, wherein said disorder or disease is cancer and the therapeutic agent is a chemotherapeutic agent.

32. The method of claim 31, wherein said chemotherapeutic agent is a taxane.

33. A method for treating plants comprising applying the composition of claim 15 to plants, wherein the active agent is a fungicide, pesticide, insecticide, herbicide or phytohormone.

* * * * *